US011491261B2

(12) United States Patent
Jongpaiboonkit et al.

(10) Patent No.: US 11,491,261 B2
(45) Date of Patent: Nov. 8, 2022

(54) COATING SCAFFOLDS

(71) Applicant: TRS Holdings LLC, Ann Arbor, MI (US)

(72) Inventors: Leenaporn Jongpaiboonkit, Madison, WI (US); William L. Murphy, Madison, WI (US); Sharon Virginia Schulzki, Rancho Santa Fe, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/060,547

(22) Filed: Mar. 3, 2016

(65) Prior Publication Data

US 2016/0271296 A1 Sep. 22, 2016

Related U.S. Application Data

(60) Provisional application No. 62/197,212, filed on Jul. 27, 2015, provisional application No. 62/127,762, filed on Mar. 3, 2015.

(51) Int. Cl.
| | | |
|---|---|---|
| *A61L 27/32* | (2006.01) | |
| *A61L 27/58* | (2006.01) | |
| *A61L 27/56* | (2006.01) | |
| *A61L 27/54* | (2006.01) | |
| *A61L 27/36* | (2006.01) | |
| *A61L 27/34* | (2006.01) | |

(52) U.S. Cl.
CPC .............. *A61L 27/32* (2013.01); *A61L 27/34* (2013.01); *A61L 27/3608* (2013.01); *A61L 27/54* (2013.01); *A61L 27/56* (2013.01); *A61L 27/58* (2013.01); *A61L 2300/104* (2013.01); *A61L 2300/404* (2013.01); *A61L 2400/18* (2013.01); *A61L 2420/06* (2013.01); *A61L 2430/02* (2013.01)

(58) Field of Classification Search
CPC ...... A61L 27/32; A61L 27/43; A61L 27/3608; A61L 27/54; A61L 27/56; A61L 27/58; A61L 2300/104; A61L 2300/404; A61L 2400/18; A61L 2420/06; A61L 2430/02
See application file for complete search history.

(56) References Cited

U.S. PATENT DOCUMENTS

| | | | |
|---|---|---|---|
| 6,471,993 | B1 | 10/2002 | Shastri et al. |
| 6,541,022 | B1 | 4/2003 | Murphy et al. |
| 6,743,779 | B1 | 6/2004 | Unger et al. |
| 6,767,928 | B1 | 7/2004 | Murphy et al. |
| 2002/0155144 | A1 | 10/2002 | Troczynski et al. |
| 2004/0023852 | A1 | 2/2004 | Roberts et al. |
| 2004/0052865 | A1 | 3/2004 | Gower et al. |
| 2004/0131652 | A1 | 7/2004 | Shindo |
| 2005/0249697 | A1 | 11/2005 | Uhrich et al. |
| 2007/0059437 | A1 | 3/2007 | Murphy et al. |
| 2007/0255422 | A1 | 11/2007 | Wei et al. |
| 2008/0090760 | A2 | 4/2008 | Hembrough et al. |
| 2008/0095817 | A1 | 4/2008 | Murphy |
| 2008/0095820 | A1 | 4/2008 | Kumta et al. |
| 2011/0022085 | A1 | 1/2011 | Murphy et al. |
| 2014/0161886 | A1 | 6/2014 | Murphy et al. |
| 2014/0350692 | A1* | 11/2014 | Jabbari ............... D01D 5/003 623/23.58 |

FOREIGN PATENT DOCUMENTS

| | | |
|---|---|---|
| JP | 2004-141630 A | 5/2004 |
| JP | 2004530675 | 10/2004 |
| JP | 2010-508125 A | 3/2010 |
| JP | 2012-503673 A | 2/2012 |
| JP | 2012-523853 A | 10/2012 |
| WO | WO2002085330 | 10/2002 |
| WO | WO2004085998 | 10/2004 |
| WO | WO2008070355 | 6/2008 |
| WO | WO2008082766 | 7/2008 |
| WO | 2009/129316 | 10/2009 |
| WO | 2010/036919 | 4/2010 |
| WO | WO-2010036919 A1 * | 4/2010 ............. A61K 9/501 |

OTHER PUBLICATIONS

Sadiasa et al., Poly(lactide-co-glycolide acid)/biphasic calcium phosphate composite coating on a porous scaffold to deliver simvastin for bone tissue engineering, Jul. 1, 2013, Journal of Drug Targeting, vol. 21 iss. 8, pp. 719-729.*
Smith et al., Increased Osteoblast cell density on nanostructured PLGA-coated nanostructured titanium for orthopedic applications, 2007, International Journal of Nanomedicine, vol. 2 iss. 3, pp. 493-499.*
Cho et al. Hydrophilized polycaprolactone nanofiber mesh-embedded poly(glycolic-co-lactic acid) membrane for effective guided bone regeneration, Nov. 3, 2008, Journal of Biomedical Materials Research Part A. (Year: 2008).*
Lee et al., Modulation of Protein Delivery from Modular Polymer Scaffolds, 2007, Biomaterials, vol. 28, pp. 1862-1870. (Year: 2007).*
Ciobanu et al., Hydroxyapatite-silver nanoparticles coatings on porous polyurethane scaffold, Feb. 1, 2014, Materials Science and Engineering: C, col. 35, pp. 36-42. (Year: 2014).*
Akhtar et al., Antisense oligonucleotide delivery to cultured macrophages is improved by incorporation into sustained-release biodegradable polymer microspheres, 1997, International Journal of Pharmaceuticals, vol. 151, pp. 57-67.

(Continued)

*Primary Examiner* — Ali Soroush

(74) *Attorney, Agent, or Firm* — Sorell, Lenna & Schmidt LLP; William D. Schmidt, Esq.

(57) ABSTRACT

Provided are compositions and methods for a scaffold coated with a primer coating and a mineral coating. Also provided is a composition for a scaffold having a mineral coating similar to bone. Also provided is a method for mineral coating a scaffold so as to promote mineral coating of the scaffold with a plate-like nanostructure and a carbonate-substituted, calcium-deficient hydroxyapatite phase.

13 Claims, 19 Drawing Sheets

(56) References Cited

OTHER PUBLICATIONS

Bajpai et al., Study of biomineralization of poly(vinyl alcohol)-based scaffolds using an alternate soaking approach, 2007, Polymer International, vol. 56, No. 4, pp. 557-568, vol. 56, No. 4.

Baron, Molecular Mechanisms of Bone Resorption by the Osteoclast, 1989, The Anatomical Record, vol. 224, pp. 317-324.

Barrere et al., Nano-scale study of the nucleation and growth of calcium phosphate coating on titanium implants, 2004, Biomaterials, vol. 25, No. 14, pp. 2901-2910.

Berchane et al., About mean diameter and size distributions of poly(lactide-co-glycolide)(PLG) microspheres, 2006, Journal of Microencapsulation, vol. 23, No. 5, pp. 539-552.

Boyer et al., Experimental Studies of Restricted Protein Diffusion in an Agarose Matrix, 1992, AIChE Journal, 1992, vol. 38, No. 2, pp. 259-272.

Chesko et al., An Investigation of the factors Controlling the Adsorption of Protein Antigens to Anionic PLG Microparticles, 2005, Journal of Pharmaceutical Sciences, vol. 94, No. 11, pp. 2510-2519.

Colman et al., Rapid Purification of Plasmid DNAs by Hydroxyapatite Chromatography, 1978, European Journal of Biochemistry, vol. 91, pp. 303-310.

Coombes et al., Biodegradable polymeric microparticles for drug delivery and vaccine formulation: the surface attachment of hydrophilic species using the concept of poly(ethylene glycol) anchoring segments, 1997, Biomaterials, vol. 18, No. 17, pp. 1153-1161.

Defail et al., Controlled release of bioactive doxorubicin from microspheres embedded within gelatin scaffolds, 2006, Journal of Biomedical Materials Research Part A, vol. 79A, pp. 954-962.

Driessens et al., Biological Calcium Phosphates and Their Role in the Physiology of Bone and Dental Tissues I. Composition and Solubility of Calcium Phosphates, 1978, Calcified Tissue Research vol. 26, pp. 127-137.

Ducheyne et al., Bioactive ceramics: the effect of surface reactivity on bone formation and bone cell function, 1999, Biomaterials, vol. 20, pp. 2287-2303.

Eniola et al., Characterization of biodegradable drug delivery vehicleswith the adhesive properties of leukocytes, 2002, Biomaterials, vol. 23, pp. 2167-2177.

Extended European Search Report dated Jul. 2, 2014 in corresponding Application No. EP 09816920.4, 7 pages.

Fazan et al., Dissolution behavior of plasma-sprayed hydroxyapatite coatings, 2000, Journal of Materials Science: Materials in Medicine, vol. 11, No. 12, pp. 787-792.

Fernandez-Pradas et al., Deposition of hydroxyapatite thin films by excimer laser ablation, 198, Thin Solid Films, vol. 317, pp. 393-396.

Ferreira et al., Human Embryoid Bodies Containing Nano- and Microparticulate Delivery Vehicles, 2008, Advanced Materials, vol. 20, 7 pages, and Supplementary Materials, 11 pages, total of 18 pages.

Fischer et al., One-step preparation of polyelectrolyte-coated PLGA microparticles and their functionalization with model ligands, 2006, Journal of Controlled Release, vol. 111, pp. 135-144.

Gao et al., Bioinspired Ceramic Thin Film Processing: Present Status and Future Perspectives, 2005, Crystal Growth & Design, vol. 5, No. 5, pp. 1983-2017.

Gledhill et al., In vitro dissolution behaviour of two morphologically different thermally sprayed hydroxyapatite coatings, 2001, Biomaterials, vol. 22, pp. 695-700.

Green et al., Mineralized polysaccharide capsules as biomimetic microenvironments for cell, gene, and growth factor delivery in tissue engineering, 2006, Soft Matter, vol. 2, pp. 732-737.

Habibovic et al., Osteoinduction by biomaterials—Physicochemical and structural influences, 2006, Journal of Biomedical Materials Research Part A, vol. 77A, No. 4, pp. 747-762.

He et al., Nucleation of apatite crystals in vitro by self-assembled dentin matrix protein 1, 2003, Nature Materials, vol. 2, No. 8, pp. 552-558.

He et al., Spatially and Temporally Controlled Biomineralization is Facilitated by Interaction Between Self-Assembled Dentin Matrix Protein 1 and Calcium Phosphate Nuclei in Solution, 2005, Biochemistry, vol. 44, No. 49, pp. 16140-161485.

Heinonen et al., A New and Convenient Colorimetric Determination of Inorganic Orthophosphate and Its Application to the Assay of Inorganic Pyrophosphatase, 1981, Analytical Biochemistry, vol. 113, pp. 313-317.

Hong et al., Hydroxyapatite/bacterial cellulose composites synthesized via a biomimetic route, 2006, Materials Letters, vol. 60, No. 13-14, pp. 1710-1713.

Hughes et al., Adsorption of bovine serum albumin onto hydroxyapatite, 1995, Biomaterials, vol. 16, pp. 697-702.

International Search Report and Written Opinion dated Dec. 24, 2009 in corresponding Application No. PCT/US09/58419 filed Sep. 25, 2009, 13 pages.

International Search Report and Written Opinion dated Jun. 9, 2016 in corresponding Application No. PCT/US16/20777 filed Mar. 3, 2016, 7 pages.

Jabbarzadeh et al., Apatite nano-crystalline surface modification of poly(lactide-co-glycolide) sintered microsphere scaffolds for bone tissue engineering: implications for protein adsorption, 2007, Journal of Biomaterials Science Polymer Edition, vol. 18, No. 9, pp. 1141-1152.

Jang et al., Controllable delivery of non-viral DNA from porous scaffolds, 2003, Journal of Controlled Release, vol. 86, pp. 157-168.

Japan Office Action dated Nov. 27, 2013 in corresponding Application No. 2011-529272, English translation, 4 pages.

Jiang et al., Stabilization of a Model Formalinized Protein Antigen Encapsulated in Poly(lactide-co-glycolide)-Based Mierusphere, 2001, Journal of Pharmaceutical Sciences, vol. 90, No. 10, pp. 1558-1569.

Jongpaiboonkit et al., Mineral-Coated Polymer Microspheres for Controlled Protein Binding and Release, 2009, Advanced Materials,vol. 21, pp. 1960-1963.

JP 2004-530675 published Oct. 7, 2004, abstract only in English, downloaded from espacenet.com, 2 pages.

Kawachi et al., Protein Adsorption Properties of Hydrothermally Prepared Hydroxyapatite, 2008, Key Engineering Materials, vols. 361-363, pp. 71-74.

Kokubo et al., Ca, P-rich layer formed on high-strength bioactive glass-ceramic A-W, 1990, Journal of Biomedical Materials Research, vol. 24, No. 3, pp. 331-343.

Kurumada et al., Formation of uniform hydroxyapatite nanocoating triggered by nucleation at carboxylic groups embedded in ethylene/acrylic acid copolymer microspheres, 2008, Colloids and Surfaces A: Physiochem. Eng. Aspects, vol. 322, pp. 34-39.

Legeros, Properties of Osteoconductive Biomaterials: Calcium Phosphates, 2002, Clinical Orthopaedics and Related Research, 2002, No. 395, pp. 81-98.

Leveque et al., Promotion of Fluorapatite Crystallization by Soluble-Matrix Proteins from Lingula Anatina Shells, 2004, Angewandte Chemie International Edition, vol. 43, No. 7, pp. 885-888.

Li et al., Apatite Formation Induced by Silica Gel in a Simulated Body Fluid, 1992, Journal of the American Ceramic Society, vol. 75, No. 8, pp. 2094-2097.

Lin et al., Surface reaction of stoichiometric and calcium-deficient hydroxyapatite in simulated body fluid, 2001, Journal of Materials Science—Materials in Medicine, vol. 12, No. 8, pp. 731-741.

Lu et al., Fabrication and Bioactivity of Porous Titanium Implant, 2007, Key Engineering Materials, vols. 342-343, pp. 613-616.

Luong et al., Spatial control of protein within biomimetically nucleated mineral, 2006, Biomaterials, vol. 27, No. 7, pp. 1175-1186.

Matsumoto et al., Hydroxyapatite particles as a controlled release carrier of protein, 2004, Biomaterials, vol. 25, pp. 3807-3812.

Meng et al., W/O/W double emulsion technique using ethyl acetate as organic solvent: effects of its diffusion rate on the characteristics of microparticles, 2003, Journal of Controlled Release, vol. 91, pp. 407-416.

Miyaji et al., Bonelike apatite coating on organic polymers, Novel nucleation process using sodium silicate solution, 1999, Biomaterials, vol. 20, pp. 913-919.

Moror et al., Solvent-induced collapse of-synuclein and acid-denatured cytochrome c, 2001, Protein Science, vol. 10, pp. 2195-2199.

(56) References Cited

OTHER PUBLICATIONS

Mu et al., Fabrication, characterization and in vitro release of paclitaxel (Taxol) loaded poly (lactic-co-glycolic acid) microspheres prepared by spray drying technique with lipid/cholesterol emulsifiers ,2001, Journal of Controlled Release, vol. 76, pp. 239-254.
Murphy et al., Growth of continuous bonelike mineral within porous poly(lactide-co-glycolide) scaffolds in vitro, 2000, Journal of Biomedical Materials Research, vol. 50, pp. 50-58.
Murphy et al., Compartmental control of mineral formation: adaptation of a biomineralization strategy for biomedical use, 2000, Polyhedron, vol. 19, pp. 357-363.
Murphy et al., Bioinspired Growth of Crystalline Carbonate Apatite on Biodegradable Polymer Substrata, 2002, Journal of the American Chemical Society, vol. 124, No. 9, pp. 1910-1917.
Murphy et al., Synthesis and in Vitro Hydroxyapatite Binding of Peptides Conjugated to Calcium-Binding Moieties, 2007, Biomaciomolecules, vol. 8, pp. 2237-2243.
Newman et al., Poly(D,L lactic-co-glycolic acid) microspheres as biodegradable microcarriers for pluripotent stem cells, 2004, Biomaterials, vol. 25, pp. 5763-5771.
O'Donnell et al., Preparation of microspheres by the solvent evaporation technique, 1997, Advanced Drug Delivery Reviews, vol. 28, pp. 25-42.
Oyane et al., Preparation and assessment of revised simulated body fluids, 2003, Journal of Biomedical Materials Research Part A, vol. 65A, pp. 188-195.
Pandey et al., Nanoparticle-Based Oral Drug Delivery System for an Injectable Antibiotic—Streptomycin, 2007, Chemotherapy, vol. 53, pp. 437-441.
Pedraza et al., Osteopontin functions as an opsonin and facilitates phagocytosis by macrophages of hydroxyapatite-coated microspheres: Implications for bone wound healing, 2008, Bone, vol. 43, No. 4, pp. 708-716.
Pena et al., New method to obtain chitosan/apatite materials at room temperature, 2006, Solid State Sciences, vol. 8, No. 5, pp. 513-519.
Porjazoska et al., Poly(lactide-co-glycolide) microparticles as systems for controlled release of proteins—Preparation and characterization, 2004, Acta Pharm., vol. 54, pp. 215-229.
Qui et al., New bioactive, degradable composite microspheres as tissue engineering substrates, 2000, Journal of Biomedical Materials Research Part A, vol. 2, No. 1, pp. 66-76.
Raman et al., Modeling small-molecule release from PLG microspheres: effects of polymer degradation and nonuniform drug distribution, 2005, Journal of Controlled Release, vol. 103, No. 1, pp. 149-158.
Ruhe et al., Controlled release of rhBMP-2 loaded poly(DL-lactic-co-glycolic acid)/calcium phosphate cement composites in vivo, 2005, Journal of Controlled Release, vol. 106, pp. 162-171.
Schmaljohann, Thermo- and pH-responsive polymers in drug delivery, 2006, Advanced Drug Delivery Reviews, vol. 58, pp. 1655-1670.
Schroder et al., Hydroxyapatite chromatography: altering the phosphate-dependent elution profile of protein as a function of pH, 2003, Analytical Biochemistry, vol. 313, pp. 176-178.

Su et al., Organization of apatite crystals in human woven bone, 2003, Bone, vol. 32, pp. 150-162, vol. 32.
Tanahashi et al., Apatite Coating on Organic Polymers by a Biomimetic Process, 1994, Journal of the American Ceramic Society, vol. 77, No. 11, pp. 2805-2808.
Uchida et al., Bonelike Apatite Formation Induced on Zirconia Gel in a Simulated Body Fluid and its Modified Solutions, 2001, Journal of the American Ceramic Society, vol. 84, No. 9, pp. 2041-2044.
Urist et al., Purification of bovine bone morphogenetic protein by hydroxyapatite chromatography, 1984, Proc. Natl. Acad. Sci. USA, vol. 81, pp. 371-375.
Vaupel et al., Blood Flow, Oxygen and Nutrient Supply, and Metabolic Microenvironment of Human Tumors: A Review, 1989, Cancer Research, vol. 49, pp. 6449-6465.
Wang et al., Preparation of hollow hydroxyapatite microspheres, 2006, J Mater Sci: Mater Med., vol. 17, pp. 641-646.
Yamaguchi et al., Enhancement of Albumin Expression in Bone Tissues With Healing Rat Fractures, 2003, Journal of Cell. Biochemistry, vol. 89, pp. 356-363.
Yamashita et al., Preparation of Apatite Thin Films through rf-Sputtering from Calcium Phosphate Glasses, 1994, Journal of the American Ceramic Society, vol. 77, No. 9, pp. 2401-2407.
Yang et al., Morphology, drug distribution, and in vitro release profiles of biodegradable polymeric microspheres containing protein fabricated by double-emulsion solvent extraction/evaporation method, 2001, Biomaterials, vol. 22, pp. 231-241.
Yokogawa et al., Growth of calcium phosphate on phosphorylated chitin fibres, 1997, Journal of Materials Science: Materials in Medicine, vol. 8, pp. 407-412.
Zhang et al., Biomimetic Polymer/Apatite Composite Scaffolds for Mineralized Tissue Engineering, 2004, Macromolecular Bioscience, 2004, vol. 4, No. 2, pp. 100-111.
Office Action dated Nov. 20, 2019 issued by the European Patent Office in European Application No. 16759535.4 filed Mar. 3, 2016 for Coating Scaffolds.
Office Action dated Jul. 26, 2019 issued by the Australian IP Offfice in Australian Application No. 2016226095 filed Mar. 3, 2016 for Coating Scaffolds.
Tomomaia, Gheorghe, et al. "On the Collagen Mineralization. A Review." Medicine and Pharmacy Reports, vol. 88, No. 1. Jan. 28, 2015, pp. 15-22.
Extended European Search Report dated Oct. 1, 2018 issued by the European Patent Office in European Application No. 16759535.4 filed Mar. 3, 2016 for Coating Scaffolds.
Sadiasa, A., et al. "Poly(lactide-co-glycolide acid)/biphasic calcium phosphate composite coating on a porous scaffold to deliver simvastatin for bone tissue engineering," J Drug Target, Sep. 2013 (8): 719-729, Abstract.
European Patent Office, Netherlands, European PatentApplication No. 16759535.4, dated Dec. 20, 2021.
Office Action issued by the Japan Patent Office dated Mar. 2, 2022 in corresponding Japanese Application No. 2021-007015 for Coating Scaffolds (English translation provided).
Canadian Office Action dated Apr. 21, 2022 in corresponding Canadian Application No. 2978002.

\* cited by examiner

FIG. 2A-F 3 day 7 day 14 day 3 day 7 day 14 day

Scale bar = 1mm

Scale bar = 500μm

Scale bar =200μm

Scale bar = 50μm

Scale bar = 1mm

Scale bar = 500µm

Scale bar =200μm

Scale bar = 50μm

Scale bar = 20μm

Scale bar = 10μm

FIG. 12A - FIG. 12B
PEEK mesh dip in 2.5 wt% PCL in chloroform
FIG. 12A
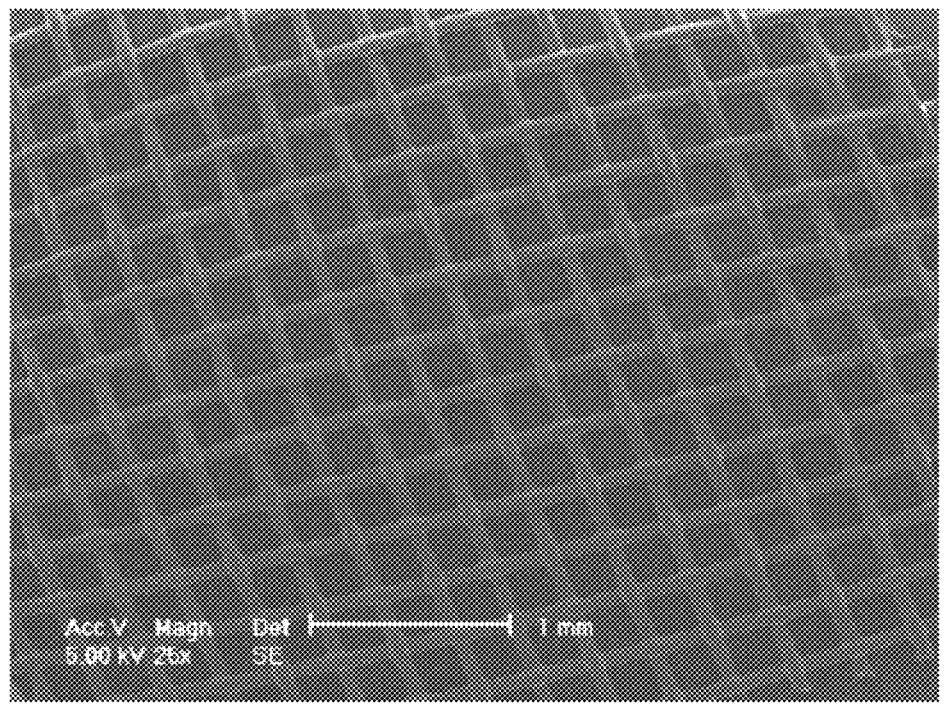
FIG. 12B
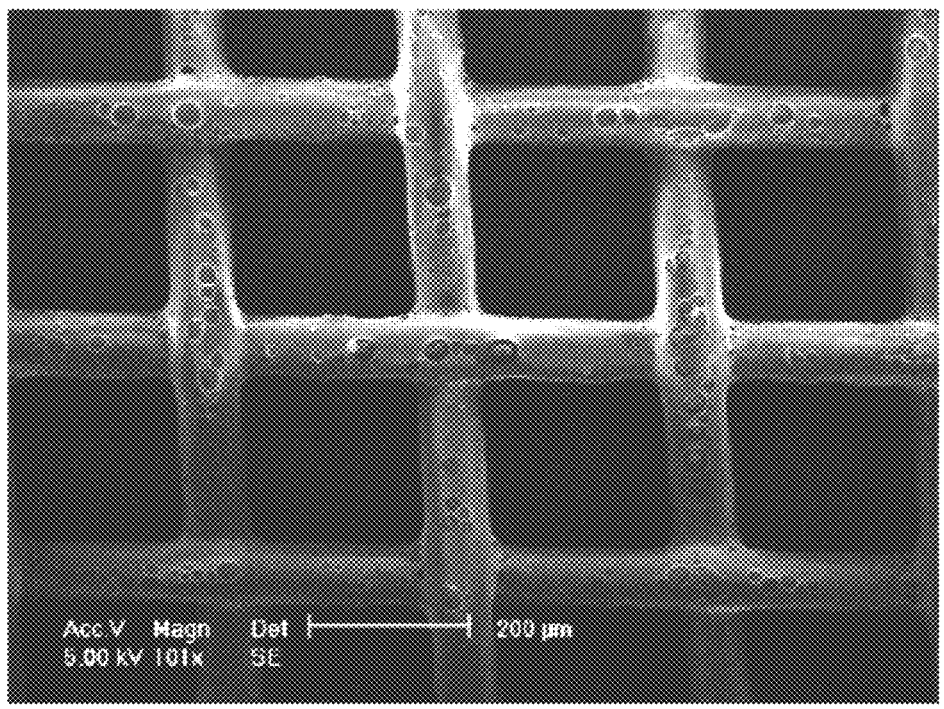

FIG. 13A – FIG. 13B
PEEK mesh dip in 2.5 wt% PCL in acetic acid
FIG. 13A
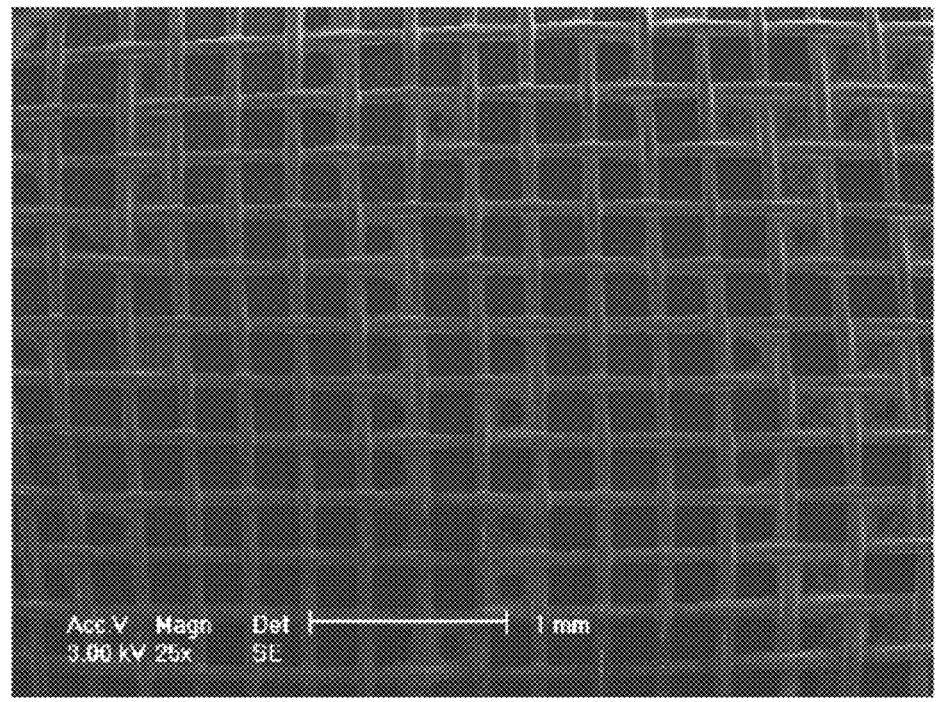
FIG. 13B
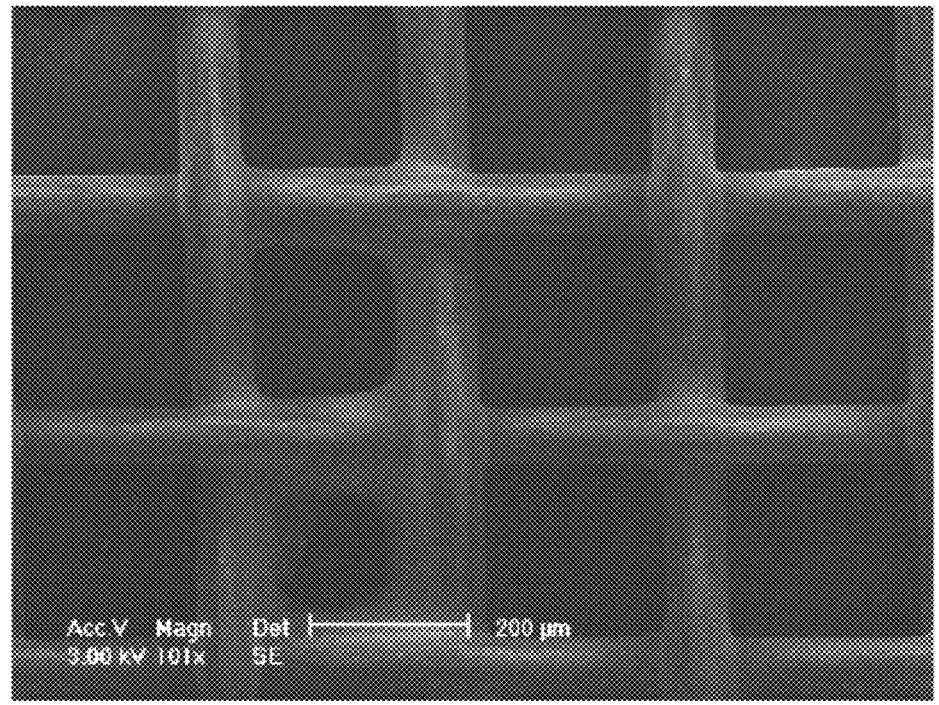

FIG. 14A - FIG. 14B
FIG. 14A
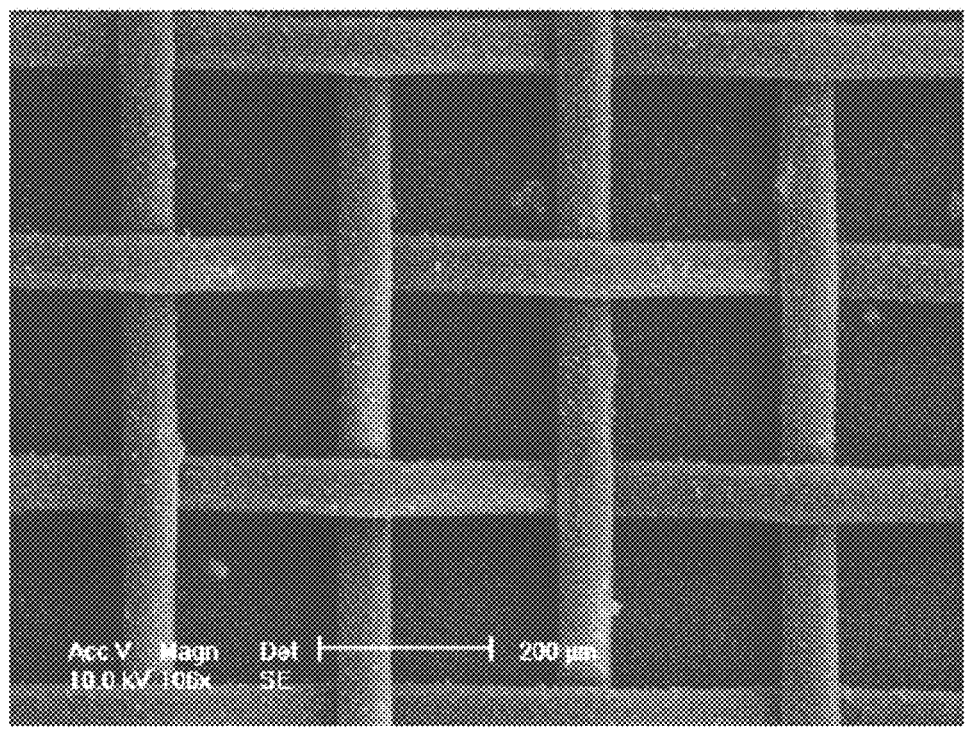
FIG. 14B
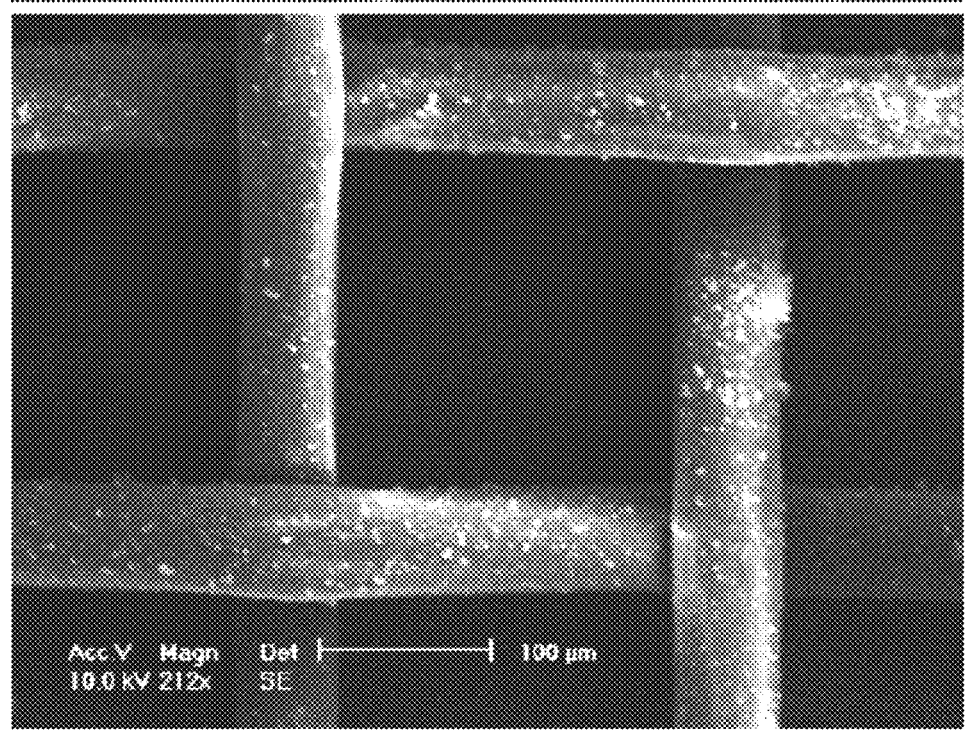

FIG. 14C - FIG. 14D
FIG. 14C
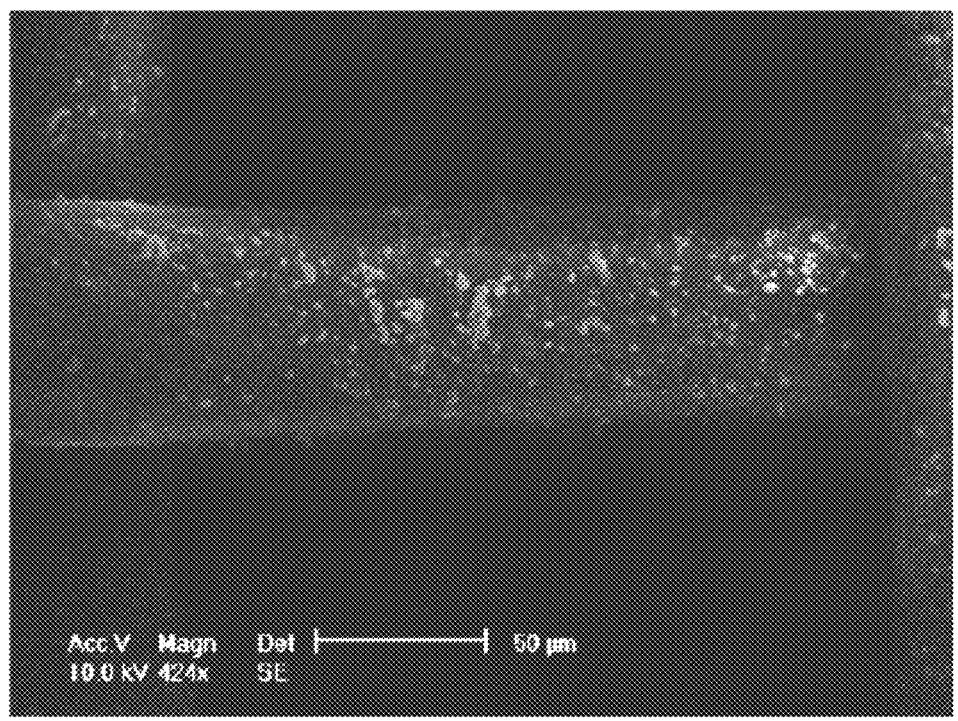
FIG. 14D
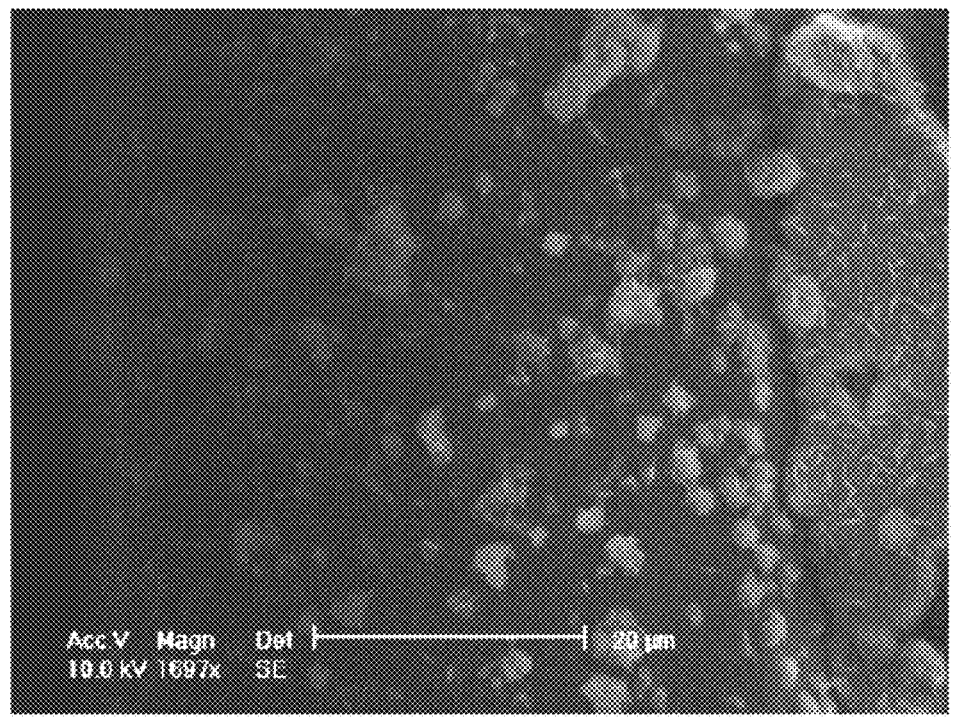

FIG. 15A - FIG. 15B
FIG. 15A
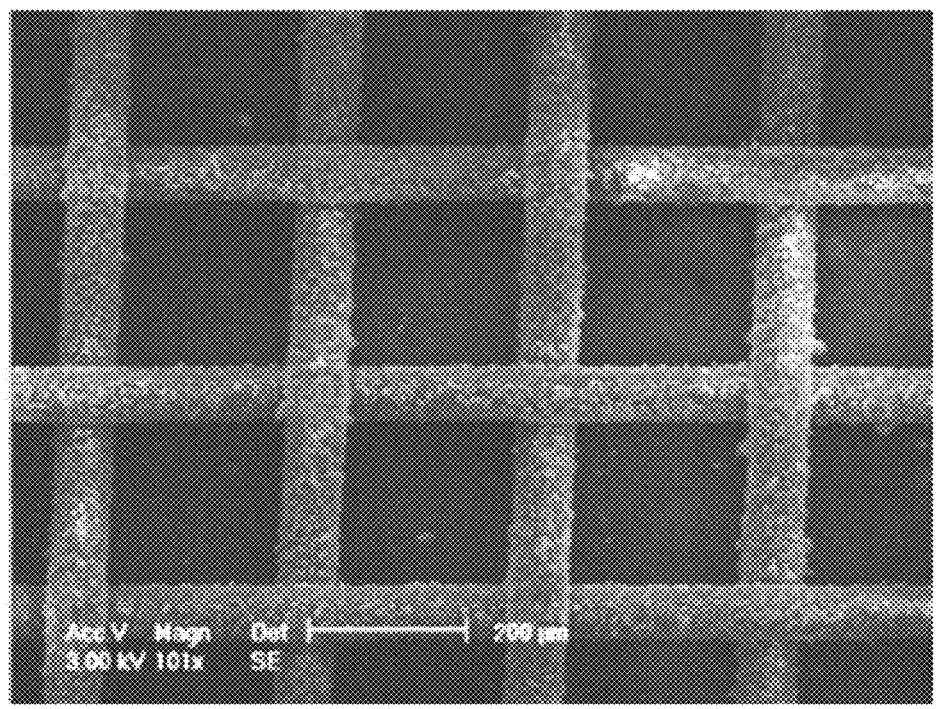
FIG. 15B
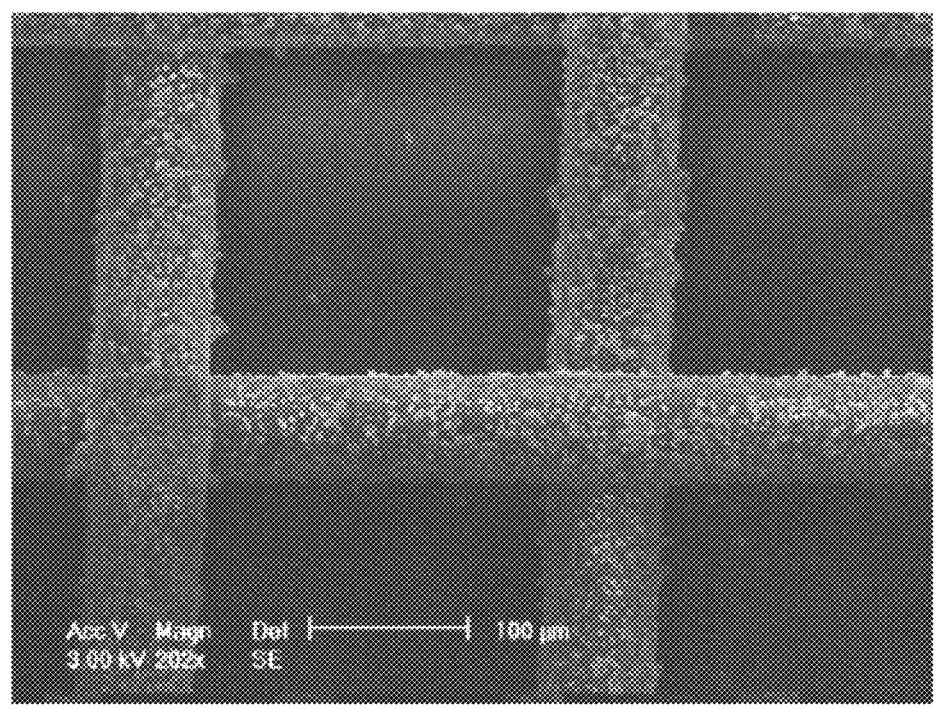

FIG. 15C - FIG. 15D
FIG. 15C
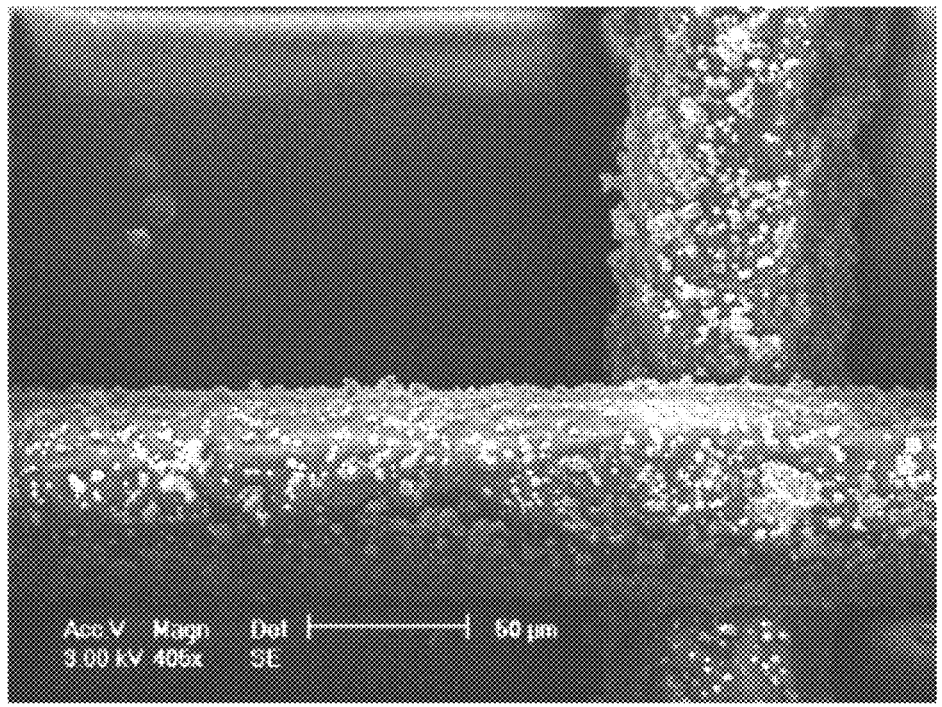
FIG. 15D
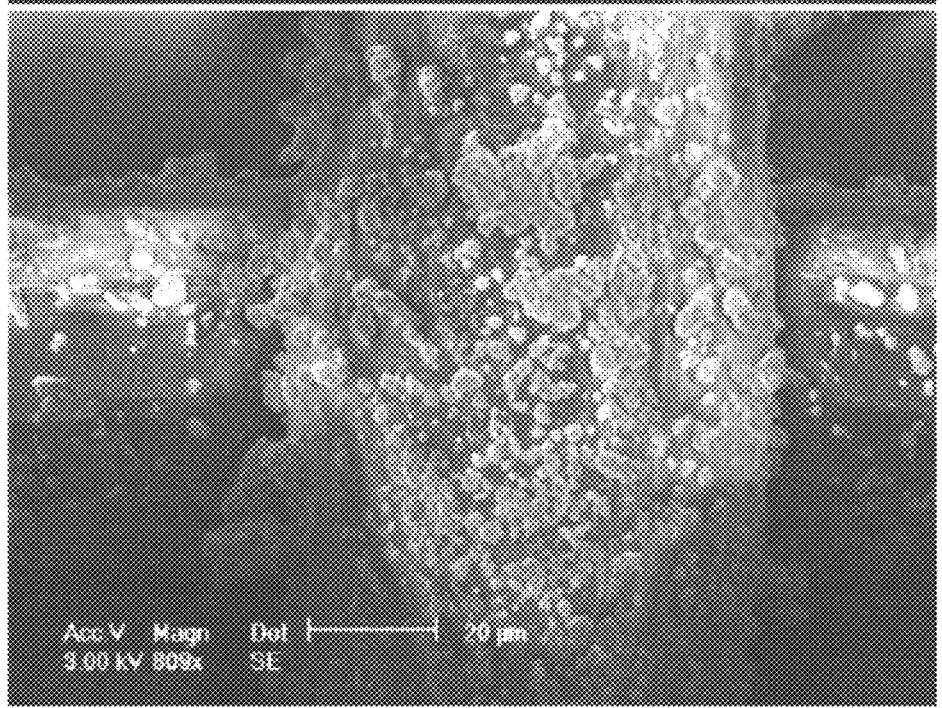

FIG. 16A - FIG. 16B
FIG. 16A
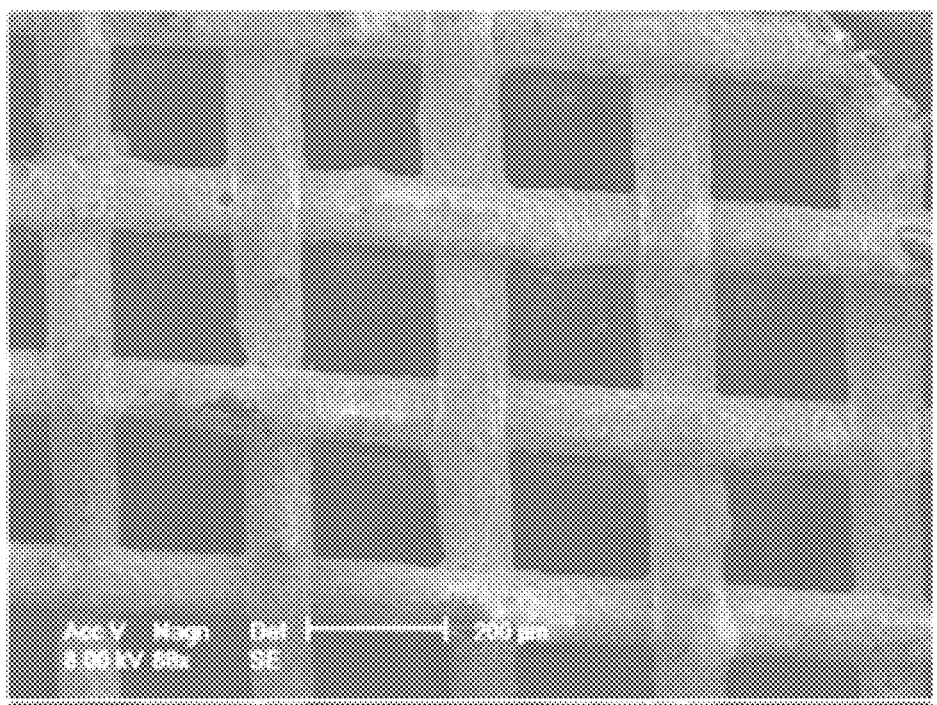
FIG. 16B
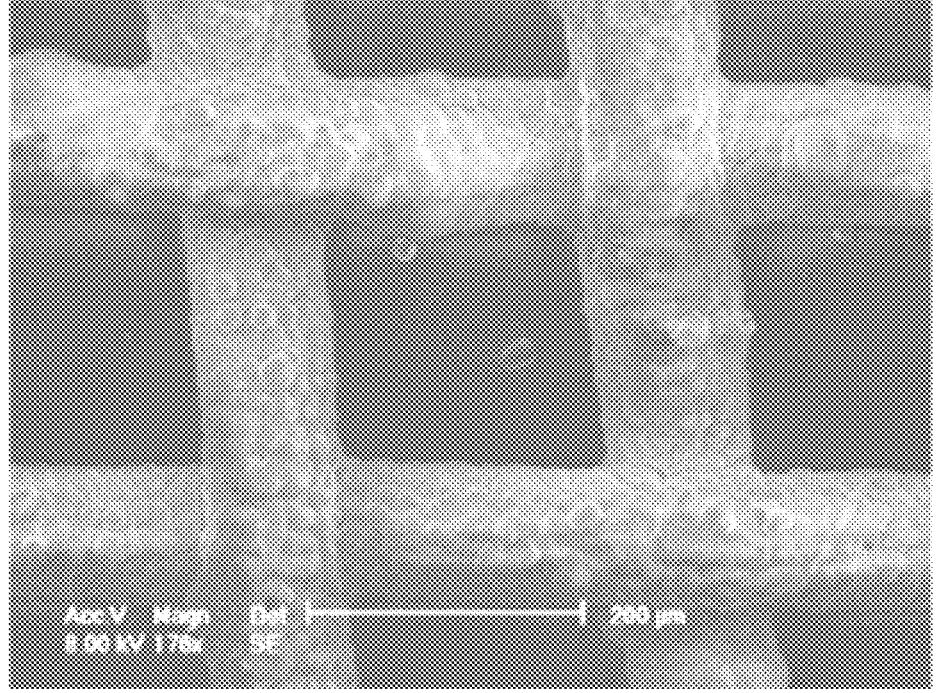

FIG. 16C - FIG. 16D
FIG. 16C
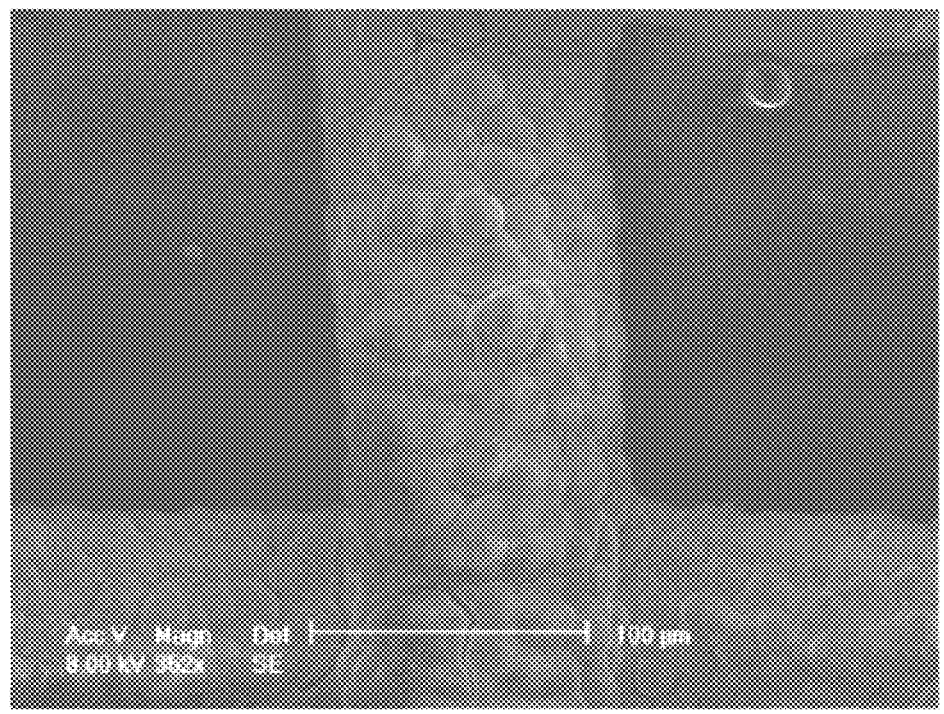
FIG. 16D
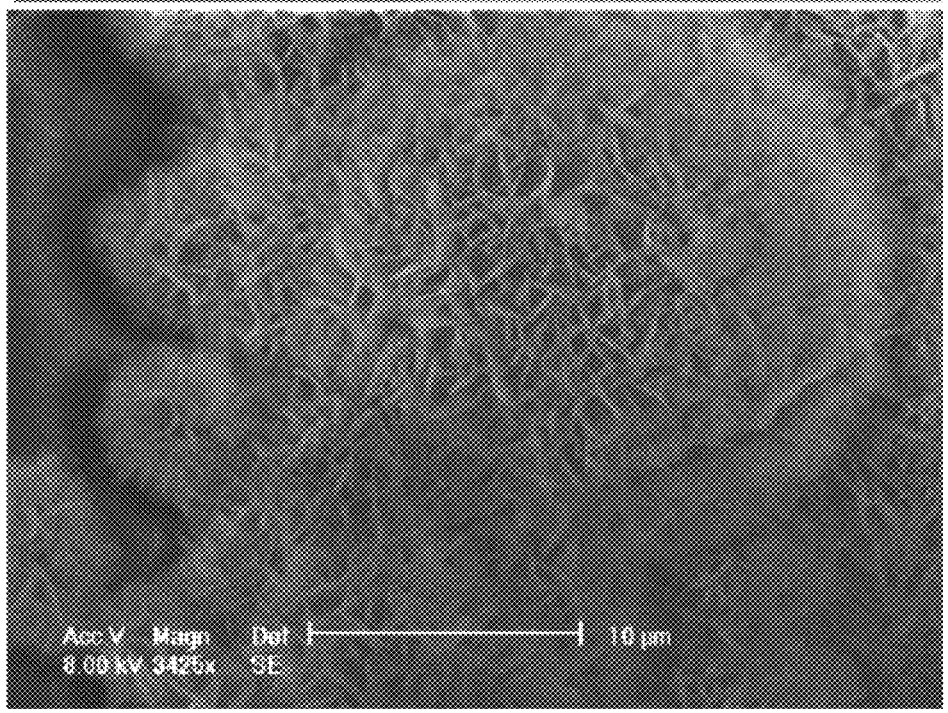

COATING SCAFFOLDS

CROSS-REFERENCE TO RELATED APPLICATIONS

This application claims priority to U.S. Provisional Application Ser. No. 62/197,212 filed 27 Jul. 2015 and U.S. Provisional Application Ser. No. 62/127,762 filed 3 Mar. 2015; each of which is incorporated herein by reference in its entirety.

STATEMENT REGARDING FEDERALLY SPONSORED RESEARCH OR DEVELOPMENT

This invention was made with government support under grant R03AR052893 awarded by The National Institutes of Health. The government has certain rights in the invention.

MATERIAL INCORPORATED-BY-REFERENCE

Not applicable.

FIELD OF THE INVENTION

The present disclosure generally relates to compositions and methods for mineral coated and primer coated scaffolds.

BACKGROUND OF THE INVENTION

Coating PEEK has proven difficult due to its high chemical resistance, low water absorption, smooth surface and high resistance to thermal degradation. Current PEEK coating methods involve high energy, high temperature, and/or highly toxic chemicals.

Hybrid materials composed of organic polymers coated with inorganic minerals have attracted much attention in biology and medicine due to their combination of advantageous properties. Polymeric materials can be a desirable base material for biomedical applications, as they can be processed into a variety of sizes and geometries, and can be designed to bioresorb in a controllable timeframe. Therefore, polymeric biomaterials have been featured in a variety of applications, including medical devices, tissue engineering scaffolds, and drug delivery systems.

Calcium phosphate based mineral coatings represent desirable surfaces for biomedical applications, as they can be similar in composition to bone tissue, and have been shown to promote favorable interactions with natural bone, a property termed "bioactivity". For example, hydroxyapatite, the major inorganic component of bone mineral, is osteoconductive (Ducheyne et al., 1999), and may also be capable of inducing new bone formation in vivo (Habibovic et al., 2006).

A particular subset of approaches used to grow hydroxyapatite coatings on biomaterials surfaces mimics some aspects of natural biomineralization processes, and has therefore been termed "biomimetic" or "bioinspired" (Hong et al., 2006; Gao and Koumoto, 2005; Leveque et al., 2004; Green et al., 2006). This type of approach is a practically and economically attractive alternative to high-temperature commercial processing methods such as plasma-spraying (Gledhill et al., 2001), sputter coating (Yamashita et al., 1994), and laser deposition (Fernandez-Pradas et al., 1998). Kokubo et al. first reported bioinspired growth of apatite coatings on bioactive $CaO$—$SiO_2$ glass in a simulated body fluid (SBF), which had ion concentrations nearly equal to those of human blood plasma and was held at physiologic temperature and pH (Kokubo et al., 1990). A series of subsequent studies reported mineral growth using novel formulations of SBF (Oyane et al., 2003), variation in the mineral growth process (Miyaji et al., 1999), or variations in the base materials (Yogogawa et al., 1997). The basis for mineral nucleation in these studies involved interactions of mineral ions in solution with polar functional groups on the materials surface, such as Si—OH (Li et al., 1992), Ti—OH (Barrere et al., 2004) and Zr—OH (Uchida et al., 2001). A series of recent studies has extended the bioinspired mineralization process to include formation of a bone-like hydroxyapatite coating on biodegradable polymer films (Murphy and Mooney, 2002) or porous scaffolds (Murphy et al., 2000; Zhang and Ma, 2004; Bajpai and Singh, 2007). The mechanism for mineral nucleation and growth on these materials is based on the interaction of carboxylate and hydroxyl groups on the hydrolyzed surface with calcium- and phosphate-rich nuclei in solution, creating a driving force for heterogeneous nucleation and mineral growth (Murphy and Mooney, 2002). This coating process is particularly suitable for biocompatible implants and biodegradable polymers, as it can be carried out at physiological temperature and pH (Tanahashi et al., 1994), and the mild processing conditions also suggest that it is possible to incorporate biologically active molecules such as polypeptides and polynucleotides, during the coating process.

Previous studies have shown that demineralized bone matrix (DBM) is an osteogenic material, but Ozturk et al. 2006 Int Orth. 30, 147-152, shows that DBM alone shows better osteoconductive properties than the DBM/hydroxyapatite (HA) mixture.

SUMMARY OF THE INVENTION

Among the various aspects of the present disclosure is the provision of compositions of a mineral coated scaffold and methods of preparing the same.

One embodiment provides a method for producing a mineral coated scaffold including (i) contacting a primer coating composition and a scaffold or incubating the primer coating composition and the scaffold for a period of time under conditions sufficient to form a primer coated scaffold; (ii) contacting the primer coated scaffold with a modified simulated body fluid; and (iii) incubating the primer coated scaffold and the modified simulated body fluid for a period of time under conditions sufficient to form a mineral coated scaffold, wherein the scaffold includes a matrix material; the primer coating composition includes a polymer or a polymer and a solvent; the primer coating of the scaffold includes a continuous or discontinuous coating; and the primer coating promotes mineral coating of the scaffold.

Another embodiment provides a method for producing a mineral coated scaffold including (i) contacting a scaffold with a modified simulated body fluid; and (ii) incubating the scaffold and the modified simulated body fluid for a period of time under conditions sufficient to form a mineral coated scaffold, wherein the scaffold comprises a matrix material; and the mineral coating comprises a plate-like nanostructure and a carbonate-substituted, calcium deficient hydroxyapatite component.

In some embodiments of the method, the matrix material or the primer coating is a biodegradable material.

In some embodiments of the method, the matrix material includes an orthopedic implant material, cardio implant material, smooth material, metal, polyethylene, machined surface, or smooth metal surface.

In some embodiments of the method, the matrix material includes a metal, calcium ceramic, polymer, or biologic material. In some embodiments of the method, the matrix material includes polycaprolactone (PCL), polyetheretherketone (PEEK), titanium (Ti), stainless steel, vitallium (cobalt-chromium), titanium, gold, hydroxyapatite, tricalcium phosphate, hydroxyapatite cement, bioactive glass, silicone, carbon fiber, carbon fiber reinforced PEEK, polyetheretherketone (PRRK), polymethylmethacrylate, hard tissue replacement (HTR) polymer, polyesters, Dacron, Mersilene, biodegradable polyesters, polyglycolic acid, poly-I-lactic acid), polyamide, Supramid, Nylamid, polyolefin, polyethylene, Medpor, polypropylene, Prolene, Marlex, cyanoacrylate, polytetrafluoroethylene, Teflon, Gore-Tex, collagen, or AlloDerm, or combinations thereof.

In some embodiments of the method, the polymer includes acrylic resin, alginate, caprolactone, collagen, chitosan, hyaluronic acid, hydrogel, hydroxybutyric acid, polyanhydride, polycaprolactone (PCL), poly(dimethylglycolic acid), polydioxanone (PDO), polyester, polyethylene, poly(ethylene glycol), poly(glycolide) (PGA), poly(glycolic acid), polyhydroxobutyrate, poly(2-hydroxyethyl-methacrylate), poly-lactide-co-glycolide (PLCG), poly(D,L-lactide-co-glycolide) (PLG), poly(lactide-co-glycolic acid) (PLGA), polylactide (PLA), polylactic acid (PLLA), poly-lactide-co-glycolide (PLCG), poly(methylethylglycolic acid), polymethylmethacrylate, polyphosphazenes, polyphosphoesters, polypropylene, poly(propylene fumarate), polyurethane (PU), or silicone rubber, or combinations or copolymers thereof. In some embodiments of the method, the polymer includes a bioresorbable polyester or a copolymer selected from one or more of the group consisting of polycaprolactone (PCL), poly(D,L-lactide-co-glycolide) (PLG), polylactide (PLA), polylactic acid (PLLA), and poly-lactide-co-glycolide (PLCG).

In some embodiments of the method, the polymer containing primer coating composition includes a ratio of about 1:1 of two polymers or a polymer and co-polymer thereof.

In some embodiments of the method, the primer coating composition includes a powder comprising a polymer.

In some embodiments of the method, wherein the primer coating composition includes a polymer with a grain size of about 10 μm to about 500 μm or an average grain size of about 10 μm to about 500 μm.

In some embodiments of the method, the solvent includes an acetic acid, alcohol, aliphatic ether, aniline, aromatic hydrocarbon, chlorinated hydrocarbon, aromatic hydrocarbon, aqueous alkali, aqueous solution of cupriethylenediamine, benzene, biphenyl, chlorinated aliphatic hydrocarbon, chlorinated hydrocarbon, chloroform, chlorophenol, chlorobenzene, cyclohexanone, chlorinated hydrocarbon, chloroauric acid, DCM, dimethylformamide (DMF), DMSO, dichlorobiphenyl, dioxane, dilute aqueous sodium hydroxide, 1,2-dichlorobenzene, dichloromethane, DCM, ethanol, ethyl acetate, ethylene carbonate, esters, formic acid, glycols, halogenated hydrocarbons, HFIP, higher aliphatic ester, higher aliphatic ketone, halogenated hydrocarbon, higher aliphatic ester, higher aliphatic ketone, ketone, higher ketone, hydrocarbon, isopropylamine, methyl ethyl ketone, morpholine, methylene chloride, methanol, methyl ethyl ketone, m-Cresol, NMP, phenol, phenylenediamine, sulfuric acid, tetramethylurea, toluene, trifluoroacetic acid, THD, tetramethylurea, tetrahydrofuran (THF), trifluoroacetic acid, trichloroethanol, toluene, trichloroethane, trichloroacetaldehyde hydrate, perfluorokerosene, pyridine, phenyl ether, piperazine, pyridine, water, or xylene, or combinations thereof.

In some embodiments of the method, the solvent is selected from 2 or more of the following solvents: chloroform, acetic acid, formic acid, or a combination of formic acid and acetic acid. In some embodiments of the method, the ratio of the two solvents is 4:1, 3:1, 2:1, or 1:1.

In some embodiments of the method, the percent weight of polymer to volume of solvent is about 1% w/v to about 10% w/v; or about 1% w/v, about 2% w/v, about 3% w/v, about 4% w/v, about 5% w/v, about 6% w/v, about 7% w/v, about 8% w/v, about 9% w/v, or about 10% w/v.

In some embodiments of the method, the applying the primer coating on the scaffold includes solvent casting, air drying, vacuum drying, or iso-temp drying.

In some embodiments of the method, the primer coated scaffold is dried for about 10 minutes to about 24 hours.

In some embodiments of the method, the primer coating includes a thin film.

In some embodiments of the method, the primer coating has a thickness of about 1 μm to about 50 μm.

In some embodiments, the method includes further combining NaCl, KCl, $MgCl_2$, $MgSO_4$, $NaHCO_3$, $CaCl_2$, and $KH_2PO_4$ to form the modified simulated body fluid. In some embodiments of the method, (i) NaCl has a concentration of about 100 mM to about 200 mM; (ii) KCl has a concentration of about 1 mM to about 8 mM; (iii) $MgCl_2$ has a concentration of about 0.2 mM to about 5 mM; (iv) $MgSO_4$ has a concentration of about 0.2 mM to about 5 mM; (v) $NaHCO_3$ has a concentration of about 1 mM to about 100 mM; (vi) $CaCl_2$ has a concentration of about 2 mM to about 20 mM; and (vii) $KH_2PO_4$ has a concentration of about 0.5 mM to about 10 mM. In some embodiments of the method, (i) NaCl has a concentration of about 141 mM; (ii) KCl has a concentration of about 4.0 mM; (iii) $MgCl_2$ has a concentration of about 1.0 mM; (iv) $MgSO_4$ has a concentration of about 0.5 mM; (v) $NaHCO_3$ has a concentration of about 4.2 mM; (vi) $CaCl_2$ has a concentration of about 5 mM; and (vii) $KH_2PO_4$ has a concentration of about 2.0 mM.

In some embodiments of the method, the modified simulated body fluid includes a buffer. In some embodiments of the method, the modified simulated body fluid includes a buffer at a concentration of about 20 mM. In some embodiments of the method, the modified simulated body fluid includes a buffer selected from the group consisting of DPBS, Tris, Tris-HCl, Tris-buffered saline, or PBS.

In some embodiments of the method, the period of time sufficient to form a primer coated scaffold is about 1 day to about 4 days.

In some embodiments of the method, contacting a primer coating composition and a scaffold includes powder coating.

In some embodiments of the method, contacting a primer coating composition and a scaffold includes dip coating.

In some embodiments of the method, incubating the primer coating composition and the scaffold for a period of time sufficient to form a primer coated scaffold is at least about 1 day; at least about 2 days; at least about 3 days; or at least about 4 days.

In some embodiments of the method, the period of time sufficient to form a mineral coated scaffold is about 1 day to about 21 days. In some embodiments of the method, the period of time sufficient to form a mineral coated scaffold is at least about 5 days; at least about 6 days; at least about 7 days; at least about 8 days; at least about 9 days; at least about 10 days; at least about 11 days; at least about 12 days; at least about 13 days; or at least about 14 days. In some embodiments of the method, the period of time sufficient to form a mineral coated scaffold is about 5 days to about 14 days.

In some embodiments, the method further includes drying the mineral coated scaffold or primer coated scaffold.

In some embodiments, the method further includes heating the primer coated scaffold under conditions sufficient to form a continuous or discontinuous coating.

In some embodiments, the method further includes heating the primer coated scaffold under conditions sufficient to dry, soften, melt, or cure the primer coating.

In some embodiments, the method further includes heating the primer coated scaffold at about 50° C. to about 200° C., sufficient to soften, melt, or cure the primer coating.

In some embodiments, the method further includes heating the primer coated scaffold for about 1 hour to about 6 hours, sufficient to soften, melt, or cure the primer coating.

In some embodiments, the method further includes hydrolyzing the scaffold or the primer coated scaffold.

In some embodiments, the method further includes roughening of the scaffold or the primer coated scaffold.

In some embodiments of the method, the incubation of the primer coated scaffold and the modified simulated body fluid includes heating the modified simulated body fluid to physiologic temperature or adjusting to a physiologic pH.

In some embodiments of the method, the physiologic temperature is about 37° C. or physiological pH is about 6.8.

In some embodiments, the method includes (i) incubating the scaffold in the primer coating composition includes replacing the primer coating composition, replenishing the primer coating composition, removing the primer coating composition, or adding the primer coating composition; or (ii) incubating the scaffold in the primer coating composition includes maintaining a concentration of primer coating composition.

In some embodiments, the method includes (i) incubating the primer coated scaffold in the modified simulated body fluid includes replacing the modified simulated body fluid, replenishing the modified simulated body fluid, removing the modified simulated body fluid, or adding the modified simulated body fluid; or (ii) incubating the primer coated scaffold in the modified simulated body fluid includes maintaining a concentration of modified simulated body fluid.

In some embodiments, the method includes maintaining the concentration of primer coating composition includes replacing, replenishing, removing, or adding polymer, solvent, or a combination thereof.

In some embodiments of the method, maintaining the concentration of modified simulated body fluid includes replacing, replenishing, removing, or adding modified simulated body fluid, NaCl, KCl, $MgCl_2$, $MgSO_4$, $NaHCO_3$, $CaCl_2$, or $KH_2PO_4$, or a combination thereof.

In some embodiments of the method, the mineral coating includes (i) about 9% to about 100% hydroxyapatite; (ii) about 90% to about 100% hydroxyapatite; or (iii) about 97% hydroxyapatite.

In some embodiments of the method, the mineral coating includes (i) about 0% to about 30% octacalcium phosphate; (ii) about 0% to about 3% octacalcium phosphate; or (iii) about 3% octacalcium phosphate.

In some embodiments of the method, wherein the mineral coating includes a porosity of (i) between about 2% and about 100%; or (ii) between about 20% and about 28%.

In some embodiments of the method, the mineral coating includes (i) a pore diameter of between about 1 nm and about 3500 nm pore; or (ii) between about 100 nm and about 350 nm pore diameter.

In some embodiments of the method, the primer coating includes a pore diameter more than about 20 μm.

In some embodiments of the method, the scaffold includes a pore diameter (i) between about 200 μm and about 525 μm; (ii) between about 25 μm to about 65 μm; or (iii) more than about 50 μm.

In some embodiments of the method, the scaffold includes a macrochannel length of more than about 100 μm.

In some embodiments of the method, the mineral coating includes (i) about 0.1 to about 18 Ca/P, or (ii) about 1.1 to about 1.76 Ca/P (calcium to phosphate ratio).

In some embodiments of the method, the mineral coating includes (i) about 1.67 to about 1.76 Ca/P, (ii) about 1.1 to about 1.3 Ca/P, or (iii) about 1.37 to about 1.61 Ca/P.

In some embodiments of the method, the mineral coating includes a crystallinity of (i) about 9% to about 100%; (ii) about 90% to about 100%; or (iii) about 96.5%.

In some embodiments, the method further includes lyophilizing the primer coated scaffold or the mineral coated scaffold.

In some embodiments, the method further includes incorporating an auxiliary component with the scaffold, wherein the auxiliary component comprises silver particles or demineralized bone matrix (DBM).

Another aspect provides a mineral coated scaffold including (i) a matrix material and a primer coating, wherein the primer coating of the scaffold includes a polymer; the primer coating of the scaffold includes a continuous or discontinuous coating; and the mineral coating of the scaffold includes a plate-like nanostructure and a carbonate-substituted, calcium-deficient hydroxyapatite component; or (ii) a matrix material, wherein the mineral coating of the scaffold comprises a plate-like nanostructure and a carbonate-substituted, calcium-deficient hydroxyapatite component.

Another aspect provides a mineral coated scaffold including (A) a matrix material and a primer coating, wherein (i) the primer coating of the scaffold includes a polymer; (ii) the primer coating of the scaffold includes a continuous or discontinuous coating; and (iii) the mineral coating of the scaffold includes a plate-like nanostructure and a carbonate-substituted, calcium-deficient hydroxyapatite component; or (B) a matrix material, wherein (i) the mineral coating of the scaffold comprises a plate-like nanostructure and a carbonate-substituted, calcium-deficient hydroxyapatite component. In some embodiments, the mineral mineral coated scaffold includes a bioresorbable thin film primer coating.

Another aspect provides a mineral coated scaffold comprising a matrix material, wherein the mineral coating of the scaffold includes a plate-like nanostructure and a carbonate-substituted, calcium-deficient hydroxyapatite component.

In some embodiments of the mineral coated scaffold the mineral coating includes: (i) about 9% to about 100% hydroxyapatite; about 90% to about 100% hydroxyapatite; or about 97% hydroxyapatite; (ii) about 0% to about 30% octacalcium phosphate; about 0% to about 3% octacalcium phosphate; or about 3% octacalcium phosphate; (iii) between about 2% and about 100% porosity; or between about 20% and about 28% porosity; (iv) between about 1 nm and about 3500 nm pore diameter; or between about 100 nm and about 350 nm pore diameter; (v) about 0.1 to about 18 Ca/P, about 1.1 to about 1.76 Ca/P, about 1.67 to about 1.76 Ca/P, about 1.1 to about 1.3 Ca/P, or about 1.37 to about 1.61 Ca/P, or (vi) about 9% to about 100% crystallinity; about 90% to about 100% crystallinity; or about 96.5% crystallinity.

In some embodiments the mineral coated scaffold includes an auxiliary component, wherein the auxiliary component comprises silver particles or demineralized bone matrix (DBM).

In some embodiments of the mineral coated scaffold, the auxiliary component comprises demineralized bone matrix (DBM), wherein the scaffold exhibits improved osteoinductive properties compared to the mineral coated scaffold without the DBM.

In some embodiments the mineral coated scaffold includes silver particles in an effective amount to provide antimicrobial, antibacterial, biostatic, or anti-infection properties.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A shows a representative SEM micrograph of the coating surfaces on PCL scaffold at low magnification.

FIG. 1B shows a representative SEM micrograph of the coating surfaces on PCL scaffold at high magnification.

FIG. 2A shows SEM micrographs of the coating surfaces after incubating in DPBS on day 3.

FIG. 2B shows SEM micrographs of the coating surfaces after incubating in DPBS on day 7.

FIG. 2C shows SEM micrographs of the coating surfaces after incubating in DPBS on day 14.

FIG. 2D shows SEM micrographs of the coating surfaces after incubating in Tris-HCl on day 3.

FIG. 2E shows SEM micrographs of the coating surfaces after incubating in Tris-HCl on day 7.

FIG. 2F shows SEM micrographs of the coating surfaces after incubating in Tris-HCl on day 14.

FIG. 3A shows the amount of cumulative phosphate release in Tris-HCl.

FIG. 3B shows the amount of cumulative calcium release in Tris-HCl and DPBS.

FIG. 4A shows SEM micrographs of the uncoated Ti.

FIG. 4B shows SEM micrographs of the coated Ti.

FIG. 5A shows SEM micrographs of the uncoated Ti (scale bar=1 mm).

FIG. 5B shows SEM micrographs of the uncoated Ti (scale bar=500 μm).

FIG. 5C shows SEM micrographs of the uncoated Ti (scale bar=200 μm).

FIG. 5D shows SEM micrographs of the uncoated Ti (scale bar=50 μm).

FIG. 6A shows SEM micrographs of the coated Ti (scale bar=1 mm).

FIG. 6B shows SEM micrographs of the coated Ti (scale bar=500 μm).

FIG. 6C shows SEM micrographs of the coated Ti (scale bar=200 μm).

FIG. 6D shows SEM micrographs of the coated Ti (scale bar=50 μm).

FIG. 11A is an SEM image of PEEK mesh at lower magnification (25×). FIG. 11B is an SEM image of PEEK mesh at higher magnification (98×).

FIG. 12A-FIG. 12B is a series of SEM images depicting PEEK mesh in 2.5 wt % PCL in chloroform. FIG. 12A is an SEM image of PEEK mesh dipped in 2.5 wt % PCL in chloroform at lower magnification (25×). FIG. 12B is an SEM image of PEEK mesh dipped in 2.5 wt % PCL in chloroform at higher magnification (101×).

FIG. 13A-FIG. 13B is a series of SEM images depicting PEEK mesh dipped in 2.5 wt % PCL in acetic acid. FIG. 13A is an SEM image of PEEK mesh dipped in 2.5 wt % PCL in acetic acid at lower magnification (25×). FIG. 13B is an SEM image of PEEK mesh dipped in 2.5 wt % PCL in acetic acid at higher magnification (101×).

FIG. 14A-FIG. 14D is a series of SEM images depicting PEEK mesh under coating condition I. FIG. 14A is an SEM image of PEEK mesh under coating condition I at 106× magnification. FIG. 14B is an SEM image of PEEK mesh under coating condition I at 212× magnification. FIG. 14C is an SEM image of PEEK mesh under coating condition I at 424× magnification. FIG. 14D is an SEM image of PEEK mesh under coating condition I at 1697× magnification.

FIG. 15A-FIG. 15D is a series of SEM images depicting PEEK mesh under coating condition II. FIG. 15A is an SEM image of PEEK mesh under coating condition II at 101× magnification. FIG. 15B is an SEM image of PEEK mesh under coating condition II at 202× magnification. FIG. 15C is an SEM image of PEEK mesh under coating condition II at 405× magnification. FIG. 15D is an SEM image of PEEK mesh under coating condition II at 809× magnification.

FIG. 16A-FIG. 16D is a series of SEM images depicting PEEK mesh under coating condition III. FIG. 16A is an SEM image of PEEK mesh under coating condition III at 88× magnification. FIG. 16B is an SEM image of PEEK mesh under coating condition III at 176× magnification. FIG. 16C is an SEM image of PEEK mesh under coating condition III at 352× magnification. FIG. 16D is an SEM image of PEEK mesh under coating condition III at 3425× magnification.

DETAILED DESCRIPTION OF THE INVENTION

Figure 1A:
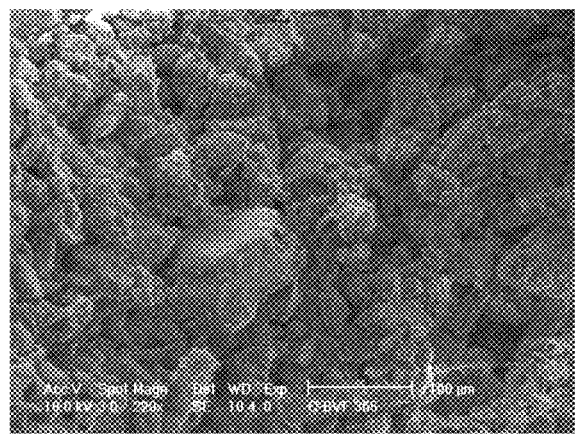
FIG. 1A-FIG. 1B are a series of micrographs depicting the coating surfaces on a PCL scaffold.

The present disclosure is based, at least in part, on the discovery that pre-treatment with a "dip" or "primer" coating of a polymer (e.g., PCL) facilitates mineral coating of materials known to be difficult to mineral coat (e.g., smooth materials, PEEK). Further, the present disclosure is based, at least in part, on the discovery of advantageous properties of methods of producing mineral coated scaffolds to form a coating similar in structure or composition to bone. As shown herein, the coated scaffolds have been produced and characterized to provide advantageous properties.

Primer Coating

A scaffold, or portion or component thereof, described herein can include a surface modification or a coating. The primer coating of a scaffold, as described herein, can be performed by any conventional manner.

The Examples describe exemplary methods that do not require the use of conventional harsh pre-treatment conditions to coat scaffold materials. For example, the methods and compositions as described herein can coat scaffolds (e.g., PEEK, metals, smooth surfaces) with a primer coating without conventional toxic pre-treatment conditions that can damage the material (e.g., the surface of the material or scaffold). Because the compositions and methods described herein do not require harsh pre-treatment conditions, the FDA has approved many materials that can be used to produce the compositions as described herein. The methods described herein can be faster or take less time to coat materials than conventional methods.

Primer Coating Composition.

The Examples describe exemplary methods for producing a primer coated scaffold using a primer coating composition comprising a polymer. For example, the primer coating composition can be a solution comprising a polymer and a solvent. As another example, the primer coating composition can be any composition comprising a polymer. The primer coating composition can be in solution state, solid state, liquid state, gas state, plasma state, or vapor phase. As another example, the primer coating composition can be a powder.

As described herein, the composition of a polymer layer on a scaffold can be manipulated by adjusting the primer coating composition, such as the polymer composition (e.g., type, concentration), additives, or solvent composition (e.g., type, concentration) in the primer coating composition.

(i) Polymer

The Examples describe exemplary methods for producing a primer coated scaffold using a polymer containing coating composition in solution. For example, a polymer containing primer coating composition can include any conventional polymer (see e.g., Nair et al. Prog. Poly. Sci 2007 32(8-9) 762-798; Miller Chou et al. Prog. Poly. Sci 2003 28 1223-1270). As another example, a polymer in a polymer containing primer coating composition can include one or more of acrylic resin, alginate, caprolactone, collagen, chitosan, hyaluronic acid, hydrogel, hydroxybutyric acid, polyanhydride, polycaprolactone (PCL), poly(dimethylglycolic acid), polydioxanone (PDO), polyester, polyethylene, poly(ethylene glycol), poly(glycolide) (PGA), poly(glycolic acid), polyhydroxobutyrate, poly(2-hydroxyethyl-methacrylate), poly-lactide-co-glycolide (PLCG), poly(D,L-lactide-co-glycolide) (PLG), poly(lactide-co-glycolic acid) (PLGA), polylactide (PLA), polylactic acid (PLLA), poly-lactide-co-glycolide (PLCG), poly(methylethylglycolic acid), polymethylmethacrylate, polyphosphazenes, polyphosphoesters, polypropylene, poly(propylene fumarate), polyurethane (PU), silicone rubber, or combinations or copolymers thereof.

As another example, a polymer in a polymer containing primer coating can include one or more of a bioresorbable polyester or its copolymers. The biodegradable polyester or its copolymer can be, for example, one or more of the following: polycaprolactone (PCL), poly(D,L-lactide-co-glycolide) (PLG), polylactide (PLA), polylactic acid (PLLA), or poly-lactide-co-glycolide (FLCG).

The primer coating composition, as described herein, can include two polymers. For example, the polymer containing primer coating composition, as described herein, can comprise a ratio of two polymers of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40. It is understood that recitation of the above discrete values includes a range between each recited value.

The primer coating composition can include a powder comprising one or more polymers as described herein. The powder can comprise a range of particle grain sizes. The powder can comprise an average grain size. For example, the powder can include a grain size or an average grain size of about 1 μm to about 5,000 μm. As another example, the powder can include a grain size or an average grain size of about 10 μm to about 500 μm. As another example, the powder can include a grain size or an average grain size of about 1 μm; about 2 μm; about 3 μm; about 4 μm; about 5 μm; about 6 μm; about 7 μm; about 8 μm; about 9 μm; about 10 μm; about 11 μm; about 12 μm; about 13 μm; about 14 μm; about 15 μm; about 16 μm; about 17 μm; about 18 μm; about 19 μm; about 20 μm; about 21 μm; about 22 μm; about 23 μm; about 24 μm; about 25 μm; about 26 μm; about 27 μm; about 28 μm; about 29 μm; about 30 μm; about 31 μm; about 32 μm; about 33 μm; about 34 μm; about 35 μm; about 36 μm; about 37 μm; about 38 μm; about 39 μm; about 40 μm; about 41 μm; about 42 μm; about 43 μm; about 44 μm; about 45 μm; about 46 μm; about 47 μm; about 48 μm; about 49 μm; about 50 μm; about 60 μm; about 70 μm; about 80 μm; about 90 μm; about 100 μm; about 110 μm; about 120 μm; about 130 μm; about 140 μm; about 150 μm; about 160 μm; about 170 μm; about 180 μm; about 190 μm; about 200 μm; about 210 μm; about 220 μm; about 230 μm; about 240 μm; about 250 μm; about 260 μm; about 270 μm; about 280 μm; about 290 μm; about 300 μm; about 310 μm; about 320 μm; about 330 μm; about 340 μm; about 350 μm; about 360 μm; about 370 μm; about 380 μm; about 390 μm; about 400 μm; about 410 μm; about 420 μm; about 430 μm; about 440 μm; about 450 μm; about 460 μm; about 470 μm; about 480 μm; about 490 μm; or about 500 μm. It is understood that recitation of the above discrete values includes a range between each recited value.

(ii) Solvent.

The Examples describe exemplary methods for producing a primer coated scaffold using a polymer containing coating composition in solution (e.g., primer coating solution). For example, the polymer containing primer coating solution can include any conventional solvent (see e.g., Nair et al. Prog. Poly. Sci 2007 32(8-9) 762-798; Miller Chou et al. Prog. Poly. Sci 2003 28 1223-1270). As another example, the solvent can be sufficient for polymer dissolution (see e.g., Miller-Chou et al. 2003 Prog. Polym. Sci. (28) 1223-1270). As another example, the solvent in the polymer containing primer coating solution can include one or more of acetic acid, alcohols, aliphatic ethers, aniline, aromatic hydrocarbons, chlorinated hydrocarbons, aromatic hydrocarbons, aqueous alkali, aqueous solutions of cupriethylenediamine, benzene, biphenyl, chlorinated aliphatic hydrocarbons, chlorinated hydrocarbons, chloroform, chlorophenol, chlorobenzene, cyclohexanone, chlorinated hydrocarbons, chloroauric acid, DCM, dimethylformamide (DMF), DMSO, dichlorobiphenyl, dioxane, dilute aqueous sodium hydroxide, 1,2-dichlorobenzene, dichloromethane, DCM, ethanol, ethyl acetate, ethylene carbonate, esters, formic acid, glycols, halogenated hydrocarbons, HFIP, higher aliphatic esters or ketones, halogenated hydrocarbons, higher aliphatic esters, higher aliphatic ketones, ketones, higher ketones, hydrocarbons, isopropylamine, methyl ethyl ketone, morpholine, methylene chloride, methanol, methyl ethyl ketone, m-Cresol, NMP, phenol, phenylenediamines, sulfuric acid, tetramethylurea, toluene, trifluoroacetic acid, THD, tetramethylurea, tetrahydrofuran (THF), trifluoroacetic acid, trichloroethanol, Toluene, trichloroethane, trichloroacetaldehyde hydrate, perfluorokerosene, pyridine, phenyl ether, piperazine, pyridine, water, or xylene, or combinations thereof.

The polymer containing primer coating solution, as described herein, can include two solvents. For example, the polymer containing primer coating solution, as described herein, can include a ratio of two solvents of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, or about 1:40. It is understood that recitation of the above discrete values includes a range between each recited value.

The polymer containing primer coating solution, as described herein, can have a weight % of polymer/volume of solvent (% w/v). For example, the polymer containing primer coating solution, as described herein, can have about 0.1% weight polymer/volume of solvent; about 0.2,% weight polymer/volume of solvent; about 0.3% weight polymer/volume of solvent; about 0.4% weight polymer/volume of solvent; about 0.5% weight polymer/volume of solvent; about 0.6% weight polymer/volume of solvent; about 0.7% weight polymer/volume of solvent; about 0.8% weight polymer/volume of solvent; about 0.9% weight polymer/volume of solvent; about 1% weight polymer/volume of solvent; about 2% weight polymer/volume of solvent; about 3% weight polymer/volume of solvent; about 4% weight polymer/volume of solvent; about 5% weight polymer/volume of solvent; about 6% weight polymer/volume of solvent; about 7% weight polymer/volume of solvent; about 8% weight polymer/volume of solvent; about 9% weight polymer/volume of solvent; about 10% weight polymer/volume of solvent; 11% weight polymer/volume of solvent; about 12% weight polymer/volume of solvent; about 13% weight polymer/volume of solvent; about 14% weight polymer/volume of solvent; about 15% weight polymer/volume of solvent; about 16% weight polymer/volume of solvent; about 17% weight polymer/volume of solvent; about 18% weight polymer/volume of solvent; about 19% weight polymer/volume of solvent; about 20% weight polymer/volume of solvent; 21% weight polymer/volume of solvent; about 22% weight polymer/volume of solvent; about 23% weight polymer/volume of solvent; about 24% weight polymer/volume of solvent; about 25% weight polymer/volume of solvent; about 26% weight polymer/volume of solvent; about 27% weight polymer/volume of solvent; about 28% weight polymer/volume of solvent; about 29% weight polymer/volume of solvent; about 30% weight polymer/volume of solvent; 31% weight polymer/volume of solvent; about 32% weight polymer/volume of solvent; about 33% weight polymer/volume of solvent; about 34% weight polymer/volume of solvent; about 35% weight polymer/volume of solvent; about 36% weight polymer/volume of solvent; about 37% weight polymer/volume of solvent; about 38% weight polymer/volume of solvent; about 39% weight polymer/volume of solvent; about 40% weight polymer/volume of solvent; 41% weight polymer/volume of solvent; about 42% weight polymer/volume of solvent; about 43% weight polymer/volume of solvent; about 44% weight polymer/volume of solvent; about 45% weight polymer/volume of solvent; about 46% weight polymer/volume of solvent; about 47% weight polymer/volume of solvent; about 48% weight polymer/volume of solvent; about 49% weight polymer/volume of solvent; about 50% weight polymer/volume of solvent; about 60% weight polymer/volume of solvent; about 70% weight polymer/volume of solvent; about 80% weight polymer/volume of solvent; about 90% weight polymer/volume of solvent; or about 100% weight polymer/volume of solvent. It is understood that recitation of the above discrete values includes a range between each recited value.

Primer Coating Deposition Techniques.

Provided herein, the primer coating can be applied by any method known in the art (see e.g., Hans-Ulrich Krebs, GK: Polymer thin films-1-Vorlesung/Lecture). For example, the primer coating can be applied by dip coating, solvent casting, painting, spray coating, spin coating, thermal spray processing (e.g., gun), annealed free standing polymer films, multilayers or diblock copolymer thin films, polymers produced by surface absorption of monolayers (SAM), floating technique, Langmuir-Blodgett films, thin film deposition techniques such as thin film deposition from the vapor phase (e.g., evaporation, sputtering, pulsed laser deposition (PLD), plasma polymerization). As another example, a primer coating composition can be a powder and be applied to the scaffold and heated under conditions sufficient to form a primer coating.

(i) Scaffold Incubation in Primer Coating Solution.

As described herein, a primer coating can be applied to a scaffold using a primer coating composition. The primer coating composition can comprise a polymer and a solvent forming a polymer containing primer coating solution.

The Examples describe exemplary methods for producing a primer coated scaffold using a polymer containing coating solution (e.g., dip coating). The scaffold can be incubated in a primer coating solution for a period of time sufficient to coat a scaffold with a primer coating (e.g., the primer coating can be continuous or discontinuous). Incubation of the scaffold in the primer coating solution can be for a period of time sufficient to deposit an amount of primer coating sufficient to promote formation of a mineral coating on the primer-coated scaffold. For example, the scaffold can be incubated in a coating solution for about 0.1 days to about 40 days. As another example, the scaffold can be incubated in a coating solution for about 1 to about 4 days.

As another example, the scaffold can be incubated in a primer coating solution between at least about 0.1 days and at least about 40 days. As another example, the scaffold can be incubated in a coating solution for at least about 0.1 day; at least about 0.2 days; at least about 0.3 days; at least about 0.4 days; at least about 0.5 days; at least about 0.6 days; at least about 0.7 days; at least about 0.8 days; at least about 0.9 days; at least about 1 day; at least about 2 days; at least about 3 days; at least about 4 days; at least about 5 days; at least about 6 days; at least about 7 days; at least about 8 days; at least about 9 days; at least about 10 days; at least about 11 days; at least about 12 days; at least about 13 days; at least about 14 days; at least about 15 days; at least about 16 days; at least about 17 days; at least about 18 days; at least about 19 days; at least about 20 days; at least about 21 days; at least about 22 days; at least about 23 days; at least about 24 days; at least about 25 days; at least about 26 days; at least about 27 days; at least about 28 days; at least about 29 days; at least about 30 days; at least about 31 days; at least about 32 days; at least about 33 days; at least about 34 days; at least about 35 days; at least about 36 days; at least about 37 days; at least about 38 days; at least about 39 days; or at least about 40 days. It is understood that recitation of the above discrete values includes a range between each recited value.

As another example, the scaffold can be incubated in a coating solution between about 0.1 days and about 40 days. As another example, the scaffold can be incubated in a coating solution for about 0.1 day; about 0.2 days; about 0.3 days; about 0.4 days; about 0.5 days; about 0.6 days; about 0.7 days; about 0.8 days; about 0.9 days; about 1 day; about 2 days; about 3 days; about 4 days; about 5 days; about 6 days; about 7 days; about 8 days; about 9 days; about 10 days; about 11 days; about 12 days; about 13 days; about 14 days; about 15 days; about 16 days; about 17 days; about 18 days; about 19 days; about 20 days; about 21 days; about 22 days; about 23 days; about 24 days; about 25 days; about 26 days; about 27 days; about 28 days; about 29 days; about 30 days; about 31 days; about 32 days; about 33 days; about 34 days; about 35 days; about 36 days; about 37 days; about 38 days; about 39 days; or about 40 days. It is understood that recitation of the above discrete values includes a range between each recited value.

(ii) Primer Coating Drying or Solvent Removal.

As described herein, the primer coating can be prepared by any method known in the art. For example, the scaffold can be coated by introducing a scaffold and a coating solution for a period of time sufficient to coat the scaffold and the coated scaffold is dried.

The primer coated scaffold can be removed from the solution and dried by any method known in the art. For example, the removal of the solvent from the primer coating solution and scaffold can be performed by air drying, vacuum drying, or iso-temp drying.

As described herein, removal of the solvent from the primer coating solution and scaffold, as described herein, can be performed by drying for at least about 1 minute to at least about 100 hours. As another example, removal of the solvent from the primer coating solution and scaffold, as described herein, can be performed by drying for at least about 10 minutes to at least about 24 hours.

As another example, removal of the solvent from the primer coating solution and scaffold, as described herein, can be performed by drying for at least about 1 minute to at least at least about 100 minutes. As another example, removal of the solvent from the primer coating solution and scaffold, as described herein, can be performed by drying for at least about 1 minute; at least about 2 minutes; at least about 3 minutes; at least about 4 minutes; at least about 5 minutes; at least about 6 minutes; at least about 7 minutes; at least about 8 minutes; at least about 9 minutes; at least about 10 minutes; at least about 11 minutes; at least about 12 minutes; at least about 13 minutes; at least about 14 minutes; at least about 15 minutes; at least about 16 minutes; at least about 17 minutes; at least about 18 minutes; at least about 19 minutes; at least about 20 minutes; at least about 21 minutes; at least about 22 minutes; at least about 23 minutes; at least about 24 minutes; at least about 25 minutes; at least about 26 minutes; at least about 27 minutes; at least about 28 minutes; at least about 29 minutes; at least about 30 minutes; at least about 31 minutes; at least about 32 minutes; at least about 33 minutes; at least about 34 minutes; at least about 35 minutes; at least about 36 minutes; at least about 37 minutes; at least about 38 minutes; at least about 39 minutes; at least about 40 minutes; at least about 41 minutes; at least about 42 minutes; at least about 43 minutes; at least about 44 minutes; at least about 45 minutes; at least about 46 minutes; at least about 47 minutes; at least about 48 minutes; at least about 49 minutes; at least about 50 minutes; at least about 51 minutes; at least about 52 minutes; at least about 53 minutes; at least about 54 minutes; at least about 55 minutes; at least about 56 minutes; at least about 57 minutes; at least about 58 minutes; at least about 59 minutes; at least about 60 minutes; at least about 61 minutes; at least about 62 minutes; at least about 63 minutes; at least about 64 minutes; at least about 65 minutes; at least about 66 minutes; at least about 67 minutes; at least about 68 minutes; at least about 69 minutes; at least about 70 minutes; at least about 71 minutes; at least about 72 minutes; at least about 73 minutes; at least about 74 minutes; at least about 75 minutes; at least about 76 minutes; at least about 77 minutes; at least about 78 minutes; at least about 79 minutes; at least about 80 minutes; at least about 81 minutes; at least about 82 minutes; at least about 83 minutes; at least about 84 minutes; at least about 85 minutes; at least about 86 minutes; at least about 87 minutes; at least about 88 minutes; at least about 89 minutes; at least about 90 minutes; at least about 91 minutes; at least about 92 minutes; at least about 93 minutes; at least about 94 minutes; at least about 95 minutes; at least about 96 minutes; at least about 97 minutes; at least about 98 minutes; at least about 99 minutes; or at least about 100 minutes. It is understood that recitation of the above discrete values includes a range between each recited value.

As another example, removal of the solvent from the primer coating solution and scaffold, as described herein, can be performed by drying for about 1 minute to about 100 minutes. As another example, removal of the solvent from the primer coating solution and scaffold, as described herein, can be performed by drying for about 1 minute; about 2 minutes; about 3 minutes; about 4 minutes; about 5 minutes; about 6 minutes; about 7 minutes; about 8 minutes; about 9 minutes; about 10 minutes; about 11 minutes; about 12 minutes; about 13 minutes; about 14 minutes; about 15 minutes; about 16 minutes; about 17 minutes; about 18 minutes; about 19 minutes; about 20 minutes; about 21 minutes; about 22 minutes; about 23 minutes; about 24 minutes; about 25 minutes; about 26 minutes; about 27 minutes; about 28 minutes; about 29 minutes; about 30 minutes; about 31 minutes; about 32 minutes; about 33 minutes; about 34 minutes; about 35 minutes; about 36 minutes; about 37 minutes; about 38 minutes; about 39 minutes; about 40 minutes; about 41 minutes; about 42 minutes; about 43 minutes; about 44 minutes; about 45 minutes; about 46 minutes; about 47 minutes; about 48 minutes; about 49 minutes; about 50 minutes; about 51 minutes; about 52 minutes; about 53 minutes; about 54 minutes; about 55 minutes; about 56 minutes; about 57 minutes; about 58 minutes; about 59 minutes; about 60 minutes; about 61 minutes; about 62 minutes; about 63 minutes; about 64 minutes; about 65 minutes; about 66 minutes; about 67 minutes; about 68 minutes; about 69 minutes; about 70 minutes; about 71 minutes; about 72 minutes; about 73 minutes; about 74 minutes; about 75 minutes; about 76 minutes; about 77 minutes; about 78 minutes; about 79 minutes; about 80 minutes; about 81 minutes; about 82 minutes; about 83 minutes; about 84 minutes; about 85 minutes; about 86 minutes; about 87 minutes; about 88 minutes; about 89 minutes; about 90 minutes; about 91 minutes; about 92 minutes; about 93 minutes; about 94 minutes; about 95 minutes; about 96 minutes; about 97 minutes; about 98 minutes; about 99 minutes; or about 100 minutes. It is understood that recitation of the above discrete values includes a range between each recited value.

As another example, removal of the solvent from the primer coating solution and scaffold, as described herein, can be performed by drying for at least about 1 hour to at least at least about 100 hours. As another example, removal of the solvent from the primer coating solution and scaffold, as described herein, can be performed by drying for at least about 1 hour; at least about 2 hours; at least about 3 hours; at least about 4 hours; at least about 5 hours; at least about 6 hours; at least about 7 hours; at least about 8 hours; at least about 9 hours; at least about 10 hours; at least about 11 hours; at least about 12 hours; at least about 13 hours; at least about 14 hours; at least about 15 hours; at least about 16 hours; at least about 17 hours; at least about 18 hours; at least about 19 hours; at least about 20 hours; at least about 21 hours; at least about 22 hours; at least about 23 hours; at least about 24 hours; at least about 25 hours; at least about 26 hours; at least about 27 hours; at least about 28 hours; at least about 29 hours; at least about 30 hours; at least about 31 hours; at least about 32 hours; at least about 33 hours; at least about 34 hours; at least about 35 hours; at least about 36 hours; at least about 37 hours; at least about 38 hours; at least about 39 hours; at least about 40 hours; at least about 41 hours; at least about 42 hours; at least about 43 hours; at least about 44 hours; at least about 45 hours; at least about 46 hours; at least about 47 hours; at least about 48 hours; at least about 49 hours; at least about 50 hours; at least about 51 hours; at least about 52 hours; at least about 53 hours; at least about 54 hours; at least about 55 hours; at least about 56 hours; at least about 57 hours; at least about 58 hours; at least about 59 hours; at least about 60 hours; at least about 61 hours; at least about 62 hours; at least about 63 hours; at least about 64 hours; at least about 65 hours; at least about 66 hours; at least about 67 hours; at least about 68 hours; at least about 69 hours; at least about 70 hours; at least about 71 hours; at least about 72 hours; at least about 73 hours; at least about 74 hours; at least about 75 hours; at least about 76 hours; at least about 77 hours; at least about 78 hours; at least about 79 hours; at least about 80 hours; at least about 81 hours; at least about 82 hours; at least about 83 hours; at least about 84 hours; at least about 85 hours; at least about 86 hours; at least about 87 hours; at least about 88 hours; at least about 89 hours; at least about 90 hours; at least about 91 hours; at least about 92 hours; at least about 93 hours; at least about 94 hours; at least about 95 hours; at least about 96 hours; at least about 97 hours; at least about 98 hours; at least about 99 hours; or at least about 100 hours. It is understood that recitation of the above discrete values includes a range between each recited value.

As another example, removal of the solvent from the primer coating solution and scaffold, as described herein, can be performed by drying for about 1 hour to about 100 hours. As another example, removal of the solvent from the primer coating solution and scaffold, as described herein, can be performed by drying for about 1 hour; about 2 hours; about 3 hours; about 4 hours; about 5 hours; about 6 hours; about 7 hours; about 8 hours; about 9 hours; about 10 hours; about 11 hours; about 12 hours; about 13 hours; about 14 hours; about 15 hours; about 16 hours; about 17 hours; about 18 hours; about 19 hours; about 20 hours; about 21 hours; about 22 hours; about 23 hours; about 24 hours; about 25 hours; about 26 hours; about 27 hours; about 28 hours; about 29 hours; about 30 hours; about 31 hours; about 32 hours; about 33 hours; about 34 hours; about 35 hours; about 36 hours; about 37 hours; about 38 hours; about 39 hours; about 40 hours; about 41 hours; about 42 hours; about 43 hours; about 44 hours; about 45 hours; about 46 hours; about 47 hours; about 48 hours; about 49 hours; about 50 hours; about 51 hours; about 52 hours; about 53 hours; about 54 hours; about 55 hours; about 56 hours; about 57 hours; about 58 hours; about 59 hours; about 60 hours; about 61 hours; about 62 hours; about 63 hours; about 64 hours; about 65 hours; about 66 hours; about 67 hours; about 68 hours; about 69 hours; about 70 hours; about 71 hours; about 72 hours; about 73 hours; about 74 hours; about 75 hours; about 76 hours; about 77 hours; about 78 hours; about 79 hours; about 80 hours; about 81 hours; about 82 hours; about 83 hours; about 84 hours; about 85 hours; about 86 hours; about 87 hours; about 88 hours; about 89 hours; about 90 hours; about 91 hours; about 92 hours; about 93 hours; about 94 hours; about 95 hours; about 96 hours; about 97 hours; about 98 hours; about 99 hours; or about 100 hours. It is understood that recitation of the above discrete values includes a range between each recited value.

(iii) Deposition of Primer Coating by Powder Coating.

As described herein, a primer coating can be applied to a scaffold using a primer coating composition. The primer coating composition can comprise a polymer and heated to form a coating on the scaffold. For example, the primer coating composition can be a powder.

A powder coating can be applied as a free-flowing, dry powder. A powder coating can be applied electrostatically. The powder can be applied by a spray process. The powder can be applied by a powder slurry process, wherein the powder is dispersed in water and coated on a surface. The powder can be applied by a powder slurry process, wherein the powder is dispersed in water and coated on a surface.

The powder can comprise any polymer known in the art or described herein. For example, the polymer can be a thermoplastic or a thermoset polymer. For example, a thermoplastic or a thermoset polymer can comprise a polyester, polyurethane, polyester-epoxy (e.g., a hybrid), straight epoxy (e.g., fusion bonded epoxy) and acrylic. The powder can comprise additives such as hardeners.

(iv) Heating of Primer Coating.

A primer coated scaffold can be heated to dry, soften, melt, or cure a primer coating. For example, a primer coating can be heated (e.g., dried, softened, melted, cured) by any method known in the art. As another example, a powder coating can be heated (e.g., dried, softened, melted, cured) to form a coating by any method known in the art.

Provided herein, the primer coating (e.g., powder coating, dip coating) can be heated at a temperature sufficient to form a coating or sufficient to dry, soften, melt, or cure the primer coating (e.g., powder coating, dip coating). For example, the temperature sufficient to form a coating or temperature sufficient to dry, soften, cure, or melt the primer coating can be between about 25° C. to about 300° C. For example, the temperature sufficient to form a coating or temperature sufficient to dry, soften, cure, or melt the primer coating can be between about 50° C. to about 200° C.

As another example, the temperature sufficient to form a coating or temperature sufficient to dry, soften, cure, or melt the primer coating can be at least about 25° C., at least about 26° C., at least about 27° C., at least about 28° C.; at least about 29° C., at least about 30° C., at least about 31° C., at least about 32° C., at least about 33° C., at least about 34° C., at least about 35° C., at least about 36° C.; at least about 37° C.; at least about 38° C.; at least about 39° C.; at least about 40° C.; at least about 41° C.; at least about 42° C.; at least about 43° C.; at least about 44° C.; at least about 45° C.; at least about 46° C.; at least about 47° C.; at least about 48° C.; at least about 49° C.; at least about 50° C.; at least about 51° C.; at least about 52° C.; at least about 53° C.; at least about 54° C.; at least about 55° C.; at least about 56° C.; at least about 57° C.; at least about 58° C.; at least about 59° C.; at least about 60° C.; at least about 61° C.; at least about 62° C.; at least about 63° C.; at least about 64° C.; at least about 65° C.; at least about 66° C.; at least about 67° C.; at least about 68° C.; at least about 69° C.; at least about 70° C.; at least about 71° C.; at least about 72° C.; at least about 73° C.; at least about 74° C.; at least about 75° C.; at least about 76° C.; at least about 77° C.; at least about 78° C.; at least about 79° C.; at least about 80° C.; at least about 81° C.; at least about 82° C.; at least about 83° C.; at least about 84° C.; at least about 85° C.; at least about 86° C.; at least about 87° C.; at least about 88° C.; at least about 89° C.; at least about 90° C.; at least about 91° C.; at least about 92° C.; at least about 93° C.; at least about 94° C.; at least about 95° C.; at least about 96° C.; at least about 97° C.; at least about 98° C.; at least about 99° C.; at least about 100° C.; at least about 101° C.; at least about 102° C.; at least about 103° C.; at least about 104° C.; at least about 105° C.; at least about 106° C.; at least about 107° C.; at least about 108° C.; at least about 109° C.; at least about 110° C., at least about 111° C.; at least about 112° C.; at least about 113° C., at least about 114° C., at least about 115° C., at least about 116° C., at least about 117° C., at least about 118° C., at least about 119° C., at least about 120° C., at least about 121° C., at least about 122° C., at least about 123° C., at least about 124° C., at least about 125° C., at least about 126° C., at least about 127° C., at least about 128° C., at least about 129° C., at least about 130° C., at least about 131° C., at least about 132° C., at least about 133° C., at least about 134° C., at least about 135° C., at least about 136° C., at least about 137° C., at least about 138° C., at least about 139° C., at least about 140° C., at least about 141° C., at least about 142° C., at least about 143° C., at least about 144° C., at least about 145° C., at least about 146° C., at least about 147° C., at least about 148° C., at least about 149° C., at least about 150° C., at least about 151° C., at least about 152° C., at least about 153° C., at least about 154° C., at least about 155° C., at least about 156° C., at least about 157° C., at least about 158° C., at least about 159° C., at least about 160° C., at least about 161° C., at least about 162° C., at least about 163° C., at least about 164° C., at least about 165° C., at least about 166° C., at least about 167° C., at least about 168° C., at least about 169° C., at least about 170° C., at least about 171° C., at least about 172° C., at least about 173° C., at least about 174° C., at least about 175° C., at least about 176° C., at least about 177° C., at least about 178° C., at least about 179° C., at least about 180° C., at least about 181° C., at least about 182° C., at least about 183° C., at least about 184° C., at least about 185° C., at least about 186° C., at least about 187° C., at least about 188° C., at least about 189° C., at least about 190° C., at least about 191° C., at least about 192° C., at least about 193° C., at least about 194° C., at least about 195° C., at least about 196° C., at least about 197° C., at least about 198° C., at least about 199° C., at least about 200° C., at least about 201° C., at least about 202° C., at least about 203° C., at least about 204° C., at least about 205° C., at least about 206° C., at least about 207° C., at least about 208° C., at least about 209° C., at least about 210° C., at least about 211° C., at least about 212° C., at least about 213° C., at least about 214° C., at least about 215° C., at least about 216° C., at least about 217° C., at least about 218° C., at least about 219° C., at least about 220° C., at least about 221° C., at least about 222° C., at least about 223° C., at least about 224° C., at least about 225° C., at least about 226° C., at least about 227° C., at least about 228° C., at least about 229° C., at least about 230° C., at least about 231° C., at least about 232° C., at least about 233° C., at least about 234° C., at least about 235° C., at least about 236° C., at least about 237° C., at least about 238° C., at least about 239° C., at least about 240° C., at least about 241° C., at least about 242° C., at least about 243° C., at least about 244° C., at least about 245° C., at least about 246° C., at least about 247° C., at least about 248° C., at least about 249° C., at least about 250° C., at least about 251° C., at least about 252° C., at least about 253° C., at least about 254° C., at least about 255° C., at least about 256° C., at least about 257° C., at least about 258° C., at least about 259° C., at least about 260° C., at least about 261° C., at least about 262° C., at least about 263° C., at least about 264° C., at least about 265° C., at least about 266° C., at least about 267° C., at least about 268° C., at least about 269° C., at least about 270° C., at least about 271° C., at least about 272° C., at least about 273° C., at least about 274° C., at least about 275° C., at least about 276° C., at least about 277° C., at least about 278° C., at least about 279° C., at least about 280° C., at least about 281° C., at least about 282° C., at least about 283° C., at least about 284° C., at least about 285° C., at least about 286° C., at least about 287° C., at least about 288° C., at least about 289° C., at least about 290° C., at least about 291° C., at least about 292° C., at least about 293° C., at least about 294° C., at least about 295° C., at least about 296° C., at least about 297° C., at least about 298° C., at least about 299° C., or at least about 300° C. It is understood that recitation of the above discrete values includes a range between each recited value.

As another example, the temperature sufficient to form a coating or temperature sufficient to dry, soften, cure, or melt the primer coating can be about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C., about 116° C., about 117° C., about 118° C., about 119° C., about 120° C., about 121° C., about 122° C., about 123° C., about 124° C., about 125° C., about 126° C., about 127° C., about 128° C., about 129° C., about 130° C., about 131° C., about 132° C., about 133° C., about 134° C., about 135° C., about 136° C., about 137° C., about 138° C., about 139° C., about 140° C., about 141° C., about 142° C., about 143° C., about 144° C., about 145° C., about 146° C., about 147° C., about 148° C., about 149° C., about 150° C., about 151° C., about 152° C., about 153° C., about 154° C., about 155° C., about 156° C., about 157° C., about 158° C., about 159° C., about 160° C., about 161° C., about 162° C., about 163° C., about 164° C., about 165° C., about 166° C., about 167° C., about 168° C., about 169° C., about 170° C., about 171° C., about 172° C., about 173° C., about 174° C., about 175° C., about 176° C., about 177° C., about 178° C., about 179° C., about 180° C., about 181° C., about 182° C., about 183° C., about 184° C., about 185° C., about 186° C., about 187° C., about 188° C., about 189° C., about 190° C., about 191° C., about 192° C., about 193° C., about 194° C., about 195° C., about 196° C., about 197° C., about 198° C., about 199° C., about 200° C., about 201° C., about 202° C., about 203° C., about 204° C., about 205° C., about 206° C., about 207° C., about 208° C., about 209° C., about 210° C., about 211° C., about 212° C., about 213° C., about 214° C., about 215° C., about 216° C., about 217° C., about 218° C., about 219° C., about 220° C., about 221° C., about 222° C., about 223° C., about 224° C., about 225° C., about 226° C., about 227° C., about 228° C., about 229° C., about 230° C., about 231° C., about 232° C., about 233° C., about 234° C., about 235° C., about 236° C., about 237° C., about 238° C., about 239° C., about 240° C., about 241° C., about 242° C., about 243° C., about 244° C., about 245° C., about 246° C., about 247° C., about 248° C., about 249° C., about 250° C., about 251° C., about 252° C., about 253° C., about 254° C., about 255° C., about 256° C., about 257° C., about 258° C., about 259° C., about 260° C., about 261° C., about 262° C., about 263° C., about 264° C., about 265° C., about 266° C., about 267° C., about 268° C., about 269° C., about 270° C., about 271° C., about 272° C., about 273° C., about 274° C., about 275° C., about 276° C., about 277° C., about 278° C., about 279° C., about 280° C., about 281° C., about 282° C., about 283° C., about 284° C., about 285° C., about 286° C., about 287° C., about 288° C., about 289° C., about 290° C., about 291° C., about 292° C., about 293° C., about 294° C., about 295° C., about 296° C., about 297° C., about 298° C., about 299° C., or about 300° C. It is understood that recitation of the above discrete values includes a range between each recited value.

Provided herein, the primer coating (e.g., powder coating, dip coating) can be heated for a period of time sufficient to form a coating or sufficient to dry, soften, cure, or melt the primer coating (e.g., powder coating, dip coating). For example, the primer coating can be heated between at least about 1 minute to least about 100 hours. As another example, heating of the primer coating can be heated between about 1 minute to at least at least about 6 hours.

As another example, heating of the primer coating can be at least about 1 minute; at least about 2 minutes; at least about 3 minutes; at least about 4 minutes; at least about 5 minutes; at least about 6 minutes; at least about 7 minutes; at least about 8 minutes; at least about 9 minutes; at least about 10 minutes; at least about 11 minutes; at least about 12 minutes; at least about 13 minutes; at least about 14 minutes; at least about 15 minutes; at least about 16 minutes; at least about 17 minutes; at least about 18 minutes; at least about 19 minutes; at least about 20 minutes; at least about 21 minutes; at least about 22 minutes; at least about 23 minutes; at least about 24 minutes; at least about 25 minutes; at least about 26 minutes; at least about 27 minutes; at least about 28 minutes; at least about 29 minutes; at least about 30 minutes; at least about 31 minutes; at least about 32 minutes; at least about 33 minutes; at least about 34 minutes; at least about 35 minutes; at least about 36 minutes; at least about 37 minutes; at least about 38 minutes; at least about 39 minutes; at least about 40 minutes; at least about 41 minutes; at least about 42 minutes; at least about 43 minutes; at least about 44 minutes; at least about 45 minutes; at least about 46 minutes; at least about 47 minutes; at least about 48 minutes; at least about 49 minutes; at least about 50 minutes; at least about 51 minutes; at least about 52 minutes; at least about 53 minutes; at least about 54 minutes; at least about 55 minutes; at least about 56 minutes; at least about 57 minutes; at least about 58 minutes; at least about 59 minutes; at least about 60 minutes; at least about 61 minutes; at least about 62 minutes; at least about 63 minutes; at least about 64 minutes; at least about 65 minutes; at least about 66 minutes; at least about 67 minutes; at least about 68 minutes; at least about 69 minutes; at least about 70 minutes; at least about 71 minutes; at least about 72 minutes; at least about 73 minutes; at least about 74 minutes; at least about 75 minutes; at least about 76 minutes; at least about 77 minutes; at least about 78 minutes; at least about 79 minutes; at least about 80 minutes; at least about 81 minutes; at least about 82 minutes; at least about 83 minutes; at least about 84 minutes; at least about 85 minutes; at least about 86 minutes; at least about 87 minutes; at least about 88 minutes; at least about 89 minutes; at least about 90 minutes; at least about 91 minutes; at least about 92 minutes; at least about 93 minutes; at least about 94 minutes; at least about 95 minutes; at least about 96 minutes; at least about 97 minutes; at least about 98 minutes; at least about 99 minutes; or at least about 100 minutes. It is understood that recitation of the above discrete values includes a range between each recited value.

As another example, heating of the primer coating can be about 1 minute; about 2 minutes; about 3 minutes; about 4 minutes; about 5 minutes; about 6 minutes; about 7 minutes; about 8 minutes; about 9 minutes; about 10 minutes; about 11 minutes; about 12 minutes; about 13 minutes; about 14 minutes; about 15 minutes; about 16 minutes; about 17 minutes; about 18 minutes; about 19 minutes; about 20 minutes; about 21 minutes; about 22 minutes; about 23 minutes; about 24 minutes; about 25 minutes; about 26 minutes; about 27 minutes; about 28 minutes; about 29 minutes; about 30 minutes; about 31 minutes; about 32 minutes; about 33 minutes; about 34 minutes; about 35 minutes; about 36 minutes; about 37 minutes; about 38 minutes; about 39 minutes; about 40 minutes; about 41 minutes; about 42 minutes; about 43 minutes; about 44 minutes; about 45 minutes; about 46 minutes; about 47 minutes; about 48 minutes; about 49 minutes; about 50 minutes; about 51 minutes; about 52 minutes; about 53 minutes; about 54 minutes; about 55 minutes; about 56 minutes; about 57 minutes; about 58 minutes; about 59 minutes; about 60 minutes; about 61 minutes; about 62 minutes; about 63 minutes; about 64 minutes; about 65 minutes; about 66 minutes; about 67 minutes; about 68 minutes; about 69 minutes; about 70 minutes; about 71 minutes; about 72 minutes; about 73 minutes; about 74 minutes; about 75 minutes; about 76 minutes; about 77 minutes; about 78 minutes; about 79 minutes; about 80 minutes; about 81 minutes; about 82 minutes; about 83 minutes; about 84 minutes; about 85 minutes; about 86 minutes; about 87 minutes; about 88 minutes; about 89 minutes; about 90 minutes; about 91 minutes; about 92 minutes; about 93 minutes; about 94 minutes; about 95 minutes; about 96 minutes; about 97 minutes; about 98 minutes; about 99 minutes; or about 100 minutes. It is understood that recitation of the above discrete values includes a range between each recited value.

As another example, heating of the primer coating can be at least about 1 hour; at least about 2 hours; at least about 3 hours; at least about 4 hours; at least about 5 hours; at least about 6 hours; at least about 7 hours; at least about 8 hours; at least about 9 hours; at least about 10 hours; at least about 11 hours; at least about 12 hours; at least about 13 hours; at least about 14 hours; at least about 15 hours; at least about 16 hours; at least about 17 hours; at least about 18 hours; at least about 19 hours; at least about 20 hours; at least about 21 hours; at least about 22 hours; at least about 23 hours; at least about 24 hours; at least about 25 hours; at least about 26 hours; at least about 27 hours; at least about 28 hours; at least about 29 hours; at least about 30 hours; at least about 31 hours; at least about 32 hours; at least about 33 hours; at least about 34 hours; at least about 35 hours; at least about 36 hours; at least about 37 hours; at least about 38 hours; at least about 39 hours; at least about 40 hours; at least about 41 hours; at least about 42 hours; at least about 43 hours; at least about 44 hours; at least about 45 hours; at least about 46 hours; at least about 47 hours; at least about 48 hours; at least about 49 hours; at least about 50 hours; at least about 51 hours; at least about 52 hours; at least about 53 hours; at least about 54 hours; at least about 55 hours; at least about 56 hours; at least about 57 hours; at least about 58 hours; at least about 59 hours; at least about 60 hours; at least about 61 hours; at least about 62 hours; at least about 63 hours; at least about 64 hours; at least about 65 hours; at least about 66 hours; at least about 67 hours; at least about 68 hours; at least about 69 hours; at least about 70 hours; at least about 71 hours; at least about 72 hours; at least about 73 hours; at least about 74 hours; at least about 75 hours; at least about 76 hours; at least about 77 hours; at least about 78 hours; at least about 79 hours; at least about 80 hours; at least about 81 hours; at least about 82 hours; at least about 83 hours; at least about 84 hours; at least about 85 hours; at least about 86 hours; at least about 87 hours; at least about 88 hours; at least about 89 hours; at least about 90 hours; at least about 91 hours; at least about 92 hours; at least about 93 hours; at least about 94 hours; at least about 95 hours; at least about 96 hours; at least about 97 hours; at least about 98 hours; at least about 99 hours; or at least about 100 hours. It is understood that recitation of the above discrete values includes a range between each recited value.

As another example, heating of the primer coating can be about 1 hour; about 2 hours; about 3 hours; about 4 hours; about 5 hours; about 6 hours; about 7 hours; about 8 hours; about 9 hours; about 10 hours; about 11 hours; about 12 hours; about 13 hours; about 14 hours; about 15 hours; about 16 hours; about 17 hours; about 18 hours; about 19 hours; about 20 hours; about 21 hours; about 22 hours; about 23 hours; about 24 hours; about 25 hours; about 26 hours; about 27 hours; about 28 hours; about 29 hours; about 30 hours; about 31 hours; about 32 hours; about 33 hours; about 34 hours; about 35 hours; about 36 hours; about 37 hours; about 38 hours; about 39 hours; about 40 hours; about 41 hours; about 42 hours; about 43 hours; about 44 hours; about 45 hours; about 46 hours; about 47 hours; about 48 hours; about 49 hours; about 50 hours; about 51 hours; about 52 hours; about 53 hours; about 54 hours; about 55 hours; about 56 hours; about 57 hours; about 58 hours; about 59 hours; about 60 hours; about 61 hours; about 62 hours; about 63 hours; about 64 hours; about 65 hours; about 66 hours; about 67 hours; about 68 hours; about 69 hours; about 70 hours; about 71 hours; about 72 hours; about 73 hours; about 74 hours; about 75 hours; about 76 hours; about 77 hours; about 78 hours; about 79 hours; about 80 hours; about 81 hours; about 82 hours; about 83 hours; about 84 hours; about 85 hours; about 86 hours; about 87 hours; about 88 hours; about 89 hours; about 90 hours; about 91 hours; about 92 hours; about 93 hours; about 94 hours; about 95 hours; about 96 hours; about 97 hours; about 98 hours; about 99 hours; or about 100 hours. It is understood that recitation of the above discrete values includes a range between each recited value.

Primer Coating Features.

As described herein, the thickness or surface morphology of the primer coating (e.g., a polymer thin film) can be tailored by varying the type of polymers, primer coating deposition techniques, ratio of two or more polymers, weight %, coating time, type of solvents, or drying techniques.

(i) Polymer.

The Examples describe exemplary methods for producing a primer coated scaffold using a primer coating composition comprising a polymer. For example, a polymer in a primer coating can include any conventional polymer (see e.g., Nair et al. Prog. Poly. Sci 2007 32(8-9) 762-798; Miller Chou et al. Prog. Poly. Sci 2003 28 1223-1270). For example, a polymer containing primer coating can include one or more of one or more of acrylic resins, alginate, caprolactone, collagen, chitosan, hyaluronic acid, hydrogels, hydroxybutyric acid, polyanhydride, polycaprolactone (PCL), poly(dimethylglycolic acid), polydioxanone (PDO), polyester, polyethylene, poly(ethylene glycol), poly(glycolide) (PGA), poly(glycolic acid), polyhydroxobutyrate, poly(2-hydroxyethyl-methacrylate), poly-lactide-co-glycolide (PLCG), poly(D,L-lactide-co-glycolide) (PLG), poly(lactide-co-glycolic acid) (PLGA), polylactide (PLA), polylactic acid (PLLA), poly-lactide-co-glycolide (PLCG), poly(methylethylglycolic acid), polymethylmethacrylate, polyphosphazenes, polyphosphoesters, polypropylene, poly(propylene fumarate), polyurethane (PU), silicone rubber, or combinations or copolymers thereof.

As another example, a polymer in a polymer containing primer coating composition can include one or more of a bioresorbable polyester or its copolymers. The biodegradable polyester or its copolymer can be, for example, one or more of the following: polycaprolactone (PCL), poly(D,L-lactide-co-glycolide) (PLG), polylactide (PLA), polylactic acid (PLLA), or poly-lactide-co-glycolide (FLCG).

(ii) Resorbable Thin Film.

As described herein, the polymer containing primer coating can be resorbable or bioresorbable. For example, the polymer containing primer coating can be a resorbable or a bioresorbable thin film.

As described herein, priming a material with a resorbable thin film can enable the type of resorbable biomaterial to be varied to address specific challenges or produce desired characteristics. For example, the polymer containing primer coating can be a polymer thin film. As another example, the polymer containing primer coating can be a resorbable thin film (e.g., a bioresorbable thin film).

As described herein, a resorbable or degradable primer coating or thin film can be tailored to degrade faster or slower as desired. For example, a resorbable or degradable primer coating or thin film can include any bioresorbable polymer known in the art (see e.g., Nair et al. Prog. Poly. Sci 2007 32(8-9) 762-798). As another example, a resorbable or degradable primer coating or thin film can include a bioresorbable polymer (e.g., polyester) or its copolymer. For example, a bioresorbable polymer or its copolymer can include a polyester (e.g., PCL), copolymer PLCG, copolymer of poly(lactide), poly(glycolide), poly(dioxanone), alginate, collagen, poly(ethylene glycol), or hyaluronic acid.

(iii) Primer Coating Coverage.

Provided herein, is the provision of a primer coated scaffold. The primer coating can be continuous or discontinuous. For example, a continuous or discontinuous primer coating can cover the entire scaffold, a portion of the scaffold, cover a % of the scaffold, or a combination thereof. For example, the primer coating, as described herein, can include a scaffold coverage of at least about 1% coverage; at least about 2% coverage; at least about 3% coverage; at least about 4% coverage; at least about 5% coverage; at least about 6% coverage; at least about 7% coverage; at least about 8% coverage; at least about 9% coverage; at least about 10% coverage; at least about 11% coverage; at least about 12% coverage; at least about 13% coverage; at least about 14% coverage; at least about 15% coverage; at least about 16% coverage; at least about 17% coverage; at least about 18% coverage; at least about 19% coverage; at least about 20% coverage; at least about 21% coverage; at least about 22% coverage; at least about 23% coverage; at least about 24% coverage; at least about 25% coverage; at least about 26% coverage; at least about 27% coverage; at least about 28% coverage; at least about 29% coverage; at least about 30% coverage; at least about 31% coverage; at least about 32% coverage; at least about 33% coverage; at least about 34% coverage; at least about 35% coverage; at least about 36% coverage; at least about 37% coverage; at least about 38% coverage; at least about 39% coverage; at least about 40% coverage; at least about 41% coverage; at least about 42% coverage; at least about 43% coverage; at least about 44% coverage; at least about 45% coverage; at least about 46% coverage; at least about 47% coverage; at least about 48% coverage; at least about 49% coverage; at least about 50% coverage; at least about 51% coverage; at least about 52% coverage; at least about 53% coverage; at least about 54% coverage; at least about 55% coverage; at least about 56% coverage; at least about 57% coverage; at least about 58% coverage; at least about 59% coverage; at least about 60% coverage; at least about 61% coverage; at least about 62% coverage; at least about 63% coverage; at least about 64% coverage; at least about 65% coverage; at least about 66% coverage; at least about 67% coverage; at least about 68% coverage; at least about 69% coverage; at least about 70% coverage; at least about 71% coverage; at least about 72% coverage; at least about 73% coverage; at least about 74% coverage; at least about 75% coverage; at least about 76% coverage; at least about 77% coverage; at least about 78% coverage; at least about 79% coverage; at least about 80% coverage; at least about 81% coverage; at least about 82% coverage; at least about 83% coverage; at least about 84% coverage; at least about 85% coverage; at least about 86% coverage; at least about 87% coverage; at least about 88% coverage; at least about 89% coverage; at least about 90% coverage; at least about 91% coverage; at least about 92% coverage; at least about 93% coverage; at least about 94% coverage; at least about 95% coverage; at least about 96% coverage; at least about 97% coverage; at least about 98% coverage; at least about 99% coverage; or at least about 100% coverage. It is understood that recitation of the above discrete values includes a range between each recited value.

As another example, the primer coating, as described herein, can include a scaffold coverage of about 1% coverage; about 2% coverage; about 3% coverage; about 4% coverage; about 5% coverage; about 6% coverage; about 7% coverage; about 8% coverage; about 9% coverage; about 10% coverage; about 11% coverage; about 12% coverage; about 13% coverage; about 14% coverage; about 15% coverage; about 16% coverage; about 17% coverage; about 18% coverage; about 19% coverage; about 20% coverage; about 21% coverage; about 22% coverage; about 23% coverage; about 24% coverage; about 25% coverage; about 26% coverage; about 27% coverage; about 28% coverage; about 29% coverage; about 30% coverage; about 31% coverage; about 32% coverage; about 33% coverage; about 34% coverage; about 35% coverage; about 36% coverage; about 37% coverage; about 38% coverage; about 39% coverage; about 40% coverage; about 41% coverage; about 42% coverage; about 43% coverage; about 44% coverage; about 45% coverage; about 46% coverage; about 47% coverage; about 48% coverage; about 49% coverage; about 50% coverage; about 51% coverage; about 52% coverage; about 53% coverage; about 54% coverage; about 55% coverage; about 56% coverage; about 57% coverage; about 58% coverage; about 59% coverage; about 60% coverage; about 61% coverage; about 62% coverage; about 63% coverage; about 64% coverage; about 65% coverage; about 66% coverage; about 67% coverage; about 68% coverage; about 69% coverage; about 70% coverage; about 71% coverage; about 72% coverage; about 73% coverage; about 74% coverage; about 75% coverage; about 76% coverage; about 77% coverage; about 78% coverage; about 79% coverage; about 80% coverage; about 81% coverage; about 82% coverage; about 83% coverage; about 84% coverage; about 85% coverage; about 86% coverage; about 87% coverage; about 88% coverage; about 89% coverage; about 90% coverage; about 91% coverage; about 92% coverage; about 93% coverage; about 94% coverage; about 95% coverage; about 96% coverage; about 97% coverage; about 98% coverage; about 99% coverage; or about 100% coverage. It is understood that recitation of the above discrete values includes a range between each recited value.

(iv) Primer Coating Thickness.

As described herein, the thickness of primer coating can be a thickness sufficient for initiating mineral coating formation. For example, conditions sufficient for mineral coating formation can include a primer coating thickness between about 0.1 µm and 500 µm. As another example, conditions sufficient for mineral coating formation can include a primer coating thickness between about 1-50 µm. As another example, the primer coating thickness sufficient for mineral coating formation can be about 0.1 µm; about 0.2, µm; about 0.3, µm; about 0.4 µm; about 0.5 µm; about 0.6 µm; about 0.7 µm; about 0.8 µm; about 0.9 µm; about 1 µm; about 2 µm; about 3 µm; about 4 µm; about 5 µm; about 6 µm; about 7 µm; about 8 µm; about 9 µm; about 10 µm; about 11 µm; about 12 µm; about 13 µm; about 14 µm; about 15 µm; about 16 µm; about 17 µm; about 18 µm; about 19 µm; about 20 µm; about 21 µm; about 22 µm; about 23 µm; about 24 µm; about 25 µm; about 26 µm; about 27 µm; about 28 µm; about 29 µm; about 30 µm; about 31 µm; about 32 µm; about 33 µm; about 34 µm; about 35 µm; about 36 µm; about 37 µm; about 38 µm; about 39 µm; about 40 µm; about 41 µm; about 42 µm; about 43 µm; about 44 µm; about 45 µm; about 46 µm; about 47 µm; about 48 µm; about 49 µm; about 50 µm; about 60 µm; about 70 µm; about 80 µm; about 90 µm; about 100 µm; about 110 µm; about 120 µm; about 130 µm; about 140 µm; about 150 µm; about 160 µm; about 170 µm; about 180 µm; about 190 µm; about 200 µm; about 210 µm; about 220 µm; about 230 µm; about 240 µm; about 250 µm; about 260 µm; about 270 µm; about 280 µm; about 290 µm; about 300 µm; about 310 µm; about 320 µm; about 330 µm; about 340 µm; about 350 µm; about 360 µm; about 370 µm; about 380 µm; about 390 µm; about 400 µm; about 410 µm; about 420 µm; about 430 µm; about 440 µm; about 450 µm; about 460 µm; about 470 µm; about 480 µm; about 490 µm; or about 500 µm. It is understood that recitation of the above discrete values includes a range between each recited value.

(v) Macrochannel Sizes after Coating.

As described herein, a primer coating can be formed onto a scaffold comprising macrochannels. For example, the primer coated scaffold can have macrochannels between at least about 20 µm and 1000 µm. As another example, the primer coated scaffold can have macrochannels of least about 100 µm.

As another example, the primer coated scaffold can have macrochannels of at least about 20 µm; at least about 30 µm; at least about 40 µm; at least about 50 µm; at least about 60 µm; at least about 70 µm; at least about 80 µm; at least about 90 µm; at least about 100 µm; at least about 110 µm; at least about 120 µm; at least about 130 µm; at least about 140 µm; at least about 150; at least about 160 µm; at least about 170 µm; at least about 180 µm; at least about 190 µm; at least about 200 µm; at least about 210 µm; at least about 220 µm; at least about 230 µm; at least about 240 µm; at least about 250; at least about 260 µm; at least about 270 µm; at least about 280 µm; at least about 290 µm; at least about 300 µm; at least about 310 µm; at least about 320 µm; at least about 330 µm; at least about 340 µm; at least about 350; at least about 360 µm; at least about 370 µm; at least about 380 µm; at least about 390 µm; at least about 400 µm; at least about 410 µm; at least about 420 µm; at least about 430 µm; at least about 440 µm; at least about 450; at least about 460 µm; at least about 470 µm; at least about 480 µm; at least about 490 µm; at least about 500 µm; at least about 510 µm; at least about 520 µm; at least about 530 µm; at least about 540 µm; at least about 550; at least about 560 µm; at least about 570 µm; at least about 580 µm; at least about 590 µm; at least about 600 µm; at least about 610 µm; at least about 620 µm; at least about 630 µm; at least about 640 µm; at least about 650; at least about 660 µm; at least about 670 µm; at least about 680 µm; at least about 690 µm; at least about 700 µm; at least about 710 µm; at least about 720 µm; at least about 730 µm; at least about 740 µm; at least about 750; at least about 760 µm; at least about 770 µm; at least about 780 µm; at least about 790 µm; at least about 800 µm; at least about 810 µm; at least about 820 µm; at least about 830 µm; at least about 840 µm; at least about 850; at least about 860 µm; at least about 870 µm; at least about 880 µm; at least about 890 µm; at least about 900 µm; at least about 910 µm; at least about 920 µm; at least about 930 µm; at least about 940 µm; at least about 950; at least about 960 µm; at least about 970 µm; at least about 980 µm; at least about 990 µm; or at least about 1000 µm. It is understood that recitation of the above discrete values includes a range between each recited value.

As another example, the primer coated scaffold can have macrochannels of about 20 µm; about 30 µm; about 40 µm; about 50 µm; about 60 µm; about 70 µm; about 80 µm; about 90 µm; about 100 µm; about 110 µm; about 120 µm; about 130 µm; about 140 µm; about 150; about 160 µm; about 170 µm; about 180 µm; about 190 µm; about 200 µm; about 210 µm; about 220 µm; about 230 µm; about 240 µm; about 250; about 260 µm; about 270 µm; about 280 µm; about 290 µm; about 300 µm; about 310 µm; about 320 µm; about 330 µm; about 340 µm; about 350; about 360 µm; about 370 µm; about 380 µm; about 390 µm; about 400 µm; about 410 µm; about 420 µm; about 430 µm; about 440 µm; about 450; about 460 µm; about 470 µm; about 480 µm; about 490 µm; about 500 µm; about 510 µm; about 520 µm; about 530 µm; about 540 µm; about 550; about 560 µm; about 570 µm; about 580 µm; about 590 µm; about 600 µm; about 610 µm; about 620 µm; about 630 µm; about 640 µm; about 650; about 660 µm; about 670 µm; about 680 µm; about 690 µm; about 700 µm; about 710 µm; about 720 µm; about 730 µm; about 740 µm; about 750; about 760 µm; about 770 µm; about 780 µm; about 790 µm; about 800 µm; about 810 µm; about 820 µm; about 830 µm; about 840 µm; about 850; about 860 µm; about 870 µm; about 880 µm; about 890 µm; about 900 µm; about 910 µm; about 920 µm; about 930 µm; about 940 µm; about 950; about 960 µm; about 970 µm; about 980 µm; about 990 µm; or about 1000 µm. It is understood that recitation of the above discrete values includes a range between each recited value.

(vi) Pore Size after Coating.

As described herein, the primer coating can formed onto a scaffold comprising pores. For example, the primer coated scaffold can have pores between at least about 2 µm and 200 µm. As another example, the primer coated scaffold can have pores of least about 20 µm.

As another example, the primer coated scaffold can have pores of at least about 2 µm; at least about 3 µm; at least about 4 µm; at least about 5 µm; at least about 6 µm; at least about 7 µm; at least about 8 µm; at least about 9 µm; at least about 10 µm; at least about 11 µm; at least about 12 µm; at least about 13 µm; at least about 14 µm; at least about 15; at least about 16 µm; at least about 17 µm; at least about 18 µm; at least about 19 µm; at least about 20 µm; at least about 21 µm; at least about 22 µm; at least about 23 µm; at least about 24 µm; at least about 25 µm; at least about 26 µm; at least about 27 µm; at least about 28 µm; at least about 29 µm; at least about 30 µm; at least about 31 µm; at least about 32 µm; at least about 33 µm; at least about 34 µm; at least about 35 µm; at least about 36 µm; at least about 37 µm; at least about 38 µm; at least about 39 µm; at least about 40 µm; at least about 41 µm; at least about 42 µm; at least about 43 µm; at least about 44 µm; at least about 45 µm; at least about 46 µm; at least about 47 µm; at least about 48 µm; at least about 49 µm; at least about 50 µm; at least about 51 µm; at least about 52 µm; at least about 53 µm; at least about 54 µm; at least about 55 µm; at least about 56 µm; at least about 57 µm; at least about 58 µm; at least about 59 µm; at least about 60 µm; at least about 61 µm; at least about 62 µm; at least about 63 µm; at least about 64 µm; at least about 65 µm; at least about 66 µm; at least about 67 µm; at least about 68 µm; at least about 69 µm; at least about 70 µm; at least about 71 µm; at least about 72 µm; at least about 73 µm; at least about 74 µm; at least about 75 µm; at least about 76 µm; at least about 77 µm; at least about 78 µm; at least about 79 µm; at least about 80 µm; at least about 81 µm; at least about 82 µm; at least about 83 µm; at least about 84 µm; at least about 85 µm; at least about 86 µm; at least about 87 µm; at least about 88 µm; at least about 89 µm; at least about 90 µm; at least about 91 µm; at least about 92 µm; at least about 93 µm; at least about 94 µm; at least about 95 µm; at least about 96 µm; at least about 97 µm; at least about 98 µm; at least about 99 µm; at least about 100 µm; at least about 110 prn, at least about 111 prn, at least about 112 prn, at least about 113 µm; at least about 114 µm; at least about 115; at least about 116 µm; at least about 117 µm; at least about 118 µm; at least about 119 µm; at least about 120 µm; at least about 121 µm; at least about 122 µm; at least about 123 µm; at least about 124 µm; at least about 125 µm; at least about 126 µm; at least about 127 µm; at least about 128 µm; at least about 129 µm; at least about 130 µm; at least about 131 µm; at least about 132 µm; at least about 133 µm; at least about 134 µm; at least about 135 µm; at least about 136 µm; at least about 137 µm; at least about 138 µm; at least about 139 µm; at least about 140 µm; at least about 141 µm; at least about 142 µm; at least about 143 µm; at least about 144 µm; at least about 145 µm; at least about 146 µm; at least about 147 µm; at least about 148 µm; at least about 149 µm; at least about 150 µm; at least about 151 µm; at least about 152 µm; at least about 153 µm; at least about 154 µm; at least about 155 µm; at least about 156 µm; at least about 157 µm; at least about 158 µm; at least about 159 µm; at least about 160 µm; at least about 161 µm; at least about 162 µm; at least about 163 µm; at least about 164 µm; at least about 165 µm; at least about 166 µm; at least about 167 µm; at least about 168 µm; at least about 169 µm; at least about 170 µm; at least about 171 µm; at least about 172 µm; at least about 173 µm; at least about 174 µm; at least about 175 µm; at least about 176 µm; at least about 177 µm; at least about 178 µm; at least about 179 µm; at least about 180 µm; at least about 181 µm; at least about 182 µm; at least about 183 µm; at least about 184 µm; at least about 185 µm; at least about 186 µm; at least about 187 µm; at least about 188 µm; at least about 189 µm; at least about 190 µm; at least about 191 µm; at least about 192 µm; at least about 193 µm; at least about 194 µm; at least about 195 µm; at least about 196 µm; at least about 197 µm; at least about 198 µm; at least about 199 µm; or at least about 200 µm. It is understood that recitation of the above discrete values includes a range between each recited value.

As another example, the primer coated scaffold can have pores of about 2 µm; about 3 µm; about 4 µm; about 5 µm; about 6 µm; about 7 µm; about 8 µm; about 9 µm, about 10 µm, about 11 µm, about 12 µm, about 13 µm, about 14 µm; about 15; about 16 µm; about 17 µm; about 18 µm; about 19 µm; about 20 µm; about 21 µm; about 22 µm; about 23 µm; about 24 µm; about 25 µm; about 26 µm; about 27 µm; about 28 µm; about 29 µm; about 30 µm; about 31 µm; about 32 µm; about 33 µm; about 34 µm; about 35 µm; about 36 µm; about 37 µm; about 38 µm; about 39 µm; about 40 µm; about 41 µm; about 42 µm; about 43 µm; about 44 µm; about 45 µm; about 46 µm; about 47 µm; about 48 µm; about 49 µm; about 50 µm; about 51 µm; about 52 µm; about 53 µm; about 54 µm; about 55 µm; about 56 µm; about 57 µm; about 58 µm; about 59 µm; about 60 µm; about 61 µm; about 62 µm; about 63 µm; about 64 µm; about 65 µm; about 66 µm; about 67 µm; about 68 µm; about 69 µm; about 70 µm; about 71 µm; about 72 µm; about 73 µm; about 74 µm; about 75 µm; about 76 µm; about 77 µm; about 78 µm; about 79 µm; about 80 µm; about 81 µm; about 82 µm; about 83 µm; about 84 µm; about 85 µm; about 86 µm; about 87 µm; about 88 µm; about 89 µm; about 90 µm; about 91 µm; about 92 µm; about 93 µm; about 94 µm; about 95 µm; about 96 µm; about 97 µm; about 98 µm; about 99 µm; about 100 µm; about 110 µm; about 111 µm; about 112 µm; about 113 µm; about 114 µm; about 115; about 116 µm; about 117 µm; about 118 µm; about 119 µm; about 120 µm; about 121 µm; about 122 µm; about 123 µm; about 124 µm; about 125 µm; about 126 µm; about 127 µm; about 128 µm; about 129 µm; about 130 µm; about 131 µm; about 132 µm; about 133 µm; about 134 µm; about 135 µm; about 136 µm; about 137 µm; about 138 µm; about 139 µm; about 140 µm; about 141 µm; about 142 µm; about 143 µm; about 144 µm; about 145 µm; about 146 µm; about 147 µm; about 148 µm; about 149 µm; about 150 µm; about 151 µm; about 152 µm; about 153 µm; about 154 µm; about 155 µm; about 156 µm; about 157 µm; about 158 µm; about 159 µm; about 160 µm; about 161 µm; about 162 µm; about 163 µm; about 164 µm; about 165 µm; about 166 µm; about 167 µm; about 168 µm; about 169 µm; about 170 µm; about 171 µm; about 172 µm; about 173 µm; about 174 µm; about 175 µm; about 176 µm; about 177 µm; about 178 µm; about 179 µm; about 180 µm; about 181 µm; about 182 µm; about 183 µm; about 184 µm; about 185 µm; about 186 µm; about 187 µm; about 188 µm; about 189 µm; about 190 µm; about 191 µm; about 192 µm; about 193 µm; about 194 µm; about 195 µm; about 196 µm; about 197 µm; about 198 µm; about 199 µm; or about 200 µm. It is understood that recitation of the above discrete values includes a range between each recited value.

As described herein, the average pore volume can be about 10%; about 20%; about 30%; about 40%; about 50%; about 60%; about 70%; about 80%; or about 90%. It is understood that recitation of the above discrete values includes a range between each recited value.

Scaffold

One aspect of the present disclosure provides a scaffold material suitable for a primer coating or a mineral coating.

As described herein, a scaffold can provide a substrate for a primer coating. A primer coating can provide a substrate for a mineral coating. The scaffold including a primer coating and simulated body fluid can promote mineral coating of the scaffold with a plate-like nanostructure or a carbonate-substituted, calcium-deficient hydroxyapatite phase.

As described herein, a scaffold can be suitable for mineral coating. A scaffold can provide a substrate for the growth of bone mineral. The scaffold including a simulated body fluid can promote mineral coating of the scaffold with a plate-like nanostructure or a carbonate-substituted, calcium-deficient hydroxyapatite phase.

A scaffold can be as described in U.S. application Ser. Nos. 13/407,441; 13/879,178; and 13/036,470 and are incorporated herein by reference.

The material can be formed of any suitable scaffold material known in the art. The selection of the scaffold material for any particular application can be made without undue experimentation. For example, an application of the scaffold can be for a medical device or an implant.

A scaffold can include a bead, a microsphere, a cage, or a modular scaffold. The mineral coated scaffolds can be prepared by the methods described in U.S. application Ser. Nos. 13/407,441; 13/879,178; and 13/036,470 and are incorporated herein by reference.

Scaffold Materials.

A scaffold can comprise a matrix material. As used herein, a "matrix" can be a material (e.g., a polymer, in which one or more ingredients can be suspended). A "scaffold" is understood to have a secondary or tertiary structure (e.g., a columnar structure or a porous structure in which one or more ingredients can permeate). The present disclosure is not limited to any particular matrix or scaffold.

A scaffold or matrix material, as described herein, can be any material suitable for use as a device or implant. A scaffold, as described herein, can be any material suitable for mineral coating or mineral composite.

A scaffold, or portion or component thereof, can be produced from proteins (e.g. extracellular matrix proteins such as fibrin, collagen, or fibronectin), polymers (e.g., polyvinylpyrrolidone), polysaccharides (e.g. alginate), hyaluronic acid, or analogs, mixtures, combinations, or derivatives of the above.

As described herein, a scaffold can be a hydrolyzable scaffold. For example, the scaffold can be biodegradable. As another example, the scaffold can be a polycaprolactone (PCL) scaffold or polyetheretherketone (PEEK) scaffold. As another example, the PCL or PEEK scaffold can be hydrolyzed using NaOH.

As described herein, a scaffold can be coated. For example, the coating can be a primer coating. As another example, the coating can be a mineral coating. As another example, the coating can be a primer coating and a mineral coating.

Polymers.

A scaffold, or portion or component thereof, can be formed from polymers, such as synthetic polymers or natural polymers.

A scaffold or matrix, as described herein, can include one or more components fabricated in whole or in part from a polymer material, such as a degradable polymer material, a porous polymer material, or a degradable porous polymer material. Suitable scaffold materials are discussed in, for example, Ma and Elisseeff, ed. (2005) Scaffolding in Tissue Engineering, CRC, ISBN 1574445219; Saltzman (2004) Tissue Engineering: Engineering Principles for the Design of Replacement Organs and Tissues, Oxford ISBN 019514130X.

A scaffold made in whole or in part from a polymer material can: provide structural or functional features of the target tissue (e.g., bone); allow cell attachment and migration; deliver and retain cells and biochemical factors; enable diffusion of cell nutrients and expressed products; or exert certain mechanical and biological influences to modify the behavior of the cell phase.

For example, a scaffold, or portion or component thereof, can be formed from synthetic polymers. For example, synthetic polymers can include poly(ethylene) glycol, bioerodible polymers (e.g., poly(lactide), poly(glycolic acid), poly (lactide-co-glycolide), poly(caprolactone), polyester (e.g., poly-(L-lactic acid), polyanhydride, polyglactin, polyglycolic acid), polycarbonates, polyamides, polyanhydrides, polyamino acids, polyortho esters, polyacetals, polycyanoacrylates), polyphosphazene, degradable polyurethanes, non-erodible polymers (e.g., polyacrylates, ethylene-vinyl acetate polymers or other acyl substituted cellulose acetates or derivatives thereof), non-erodible polyurethanes, polystyrenes, polyvinyl chloride, polyvinyl fluoride, polyvinyl pyrrolidone, poly(vinylimidazole), chlorosulphonated polyolifins, polyethylene oxide, polyvinyl alcohol (e.g., polyvinyl alcohol sponge), synthetic marine adhesive proteins, Teflon®, nylon, or analogs, mixtures, combinations (e.g., polyethylene oxide-polypropylene glycol block copolymer, poly (D,L-lactide-co-glycolide) fiber matrix), or analogs, mixtures, combinations, or derivatives of any of the above.

As another example, suitable scaffold materials can include a collagen gel, polyvinyl alcohol, a marine adhesive protein, a PLG fiber matrix, a polyglactin fiber, a calcium alginate gel, a polyglycolic acid, polyester (e.g., poly-(L-lactic acid) or a polyanhydride), a polysaccharide (e.g. alginate), chitosan, polyphosphazene, polyacrylate, polyethylene oxide-polypropylene glycol block copolymer, fibrin, collagen, fibronectin, polyvinylpyrrolidone, hyaluronic acid, poly(lactide), poly(glycolic acid), poly(lactide-co-glycolide), poly(caprolactone), polycarbonates, polyamides, polyanhydrides, polyamino acids, polyortho esters, polyacetals, polycyanoacrylates), polyurethanes, polyacrylates, ethylene-vinyl acetate polymers or other acyl substituted cellulose acetates or derivatives thereof), polyurethanes, polystyrenes, polyvinyl chloride, polyvinyl fluoride, poly (vinylimidazole), chlorosulphonated polyolifins, polyethylene oxide, polyvinyl alcohol, Teflon®, nylon, or analogs, mixtures, combinations, or derivatives of any of the above.

As another example, a scaffold, or portion or component thereof, can be formed of naturally occurring polymers or natively derived polymers. For example, a naturally occurring polymer or natively derived polymer can comprise agarose, alginate (e.g., calcium alginate gel), fibrin, fibrinogen, fibronectin, collagen (e.g., a collagen gel), gelatin, hyaluronic acid, chitin, or other suitable polymers or biopolymers, or analogs, mixtures, combinations, or derivatives of the above. Also, a scaffold, or portion or component thereof, can be formed from a mixture of naturally occurring biopolymers or synthetic polymers.

As another example, a scaffold, or portion or component thereof, can comprise polycarboxylates, polyanhydrides, poly(α-hydroxyesters), poly(ethylene terephthalates), poly (carbonates), poly(amides), poly(lactones), poly(saccharides), poly(acrylates), or analogs, mixtures, combinations, or derivatives of any of the above.

In some embodiments, a scaffold, or portion or component thereof, can comprise polycaprolactone, polylactide, polyglycolide, poly(lactide-glycolide), poly(propylene fumarate), poly(caprolactone fumarate), polyethylene glycol, poly(glycolide-co-caprolactone), or analogs, mixtures, combinations, or derivatives of any of the above.

Crystalline or Mineral Component

A scaffold, or portion or component thereof, can comprise a crystalline or mineral component. For example, a scaffold, or portion or component thereof, can include the inorganic mineral hydroxyapatite (also known as hydroxylapatite). About seventy percent of natural bone can be made up of hydroxyapatite. In some embodiments, a scaffold, or portion or component thereof, comprises a ground natural substance containing hydroxyapatite, such as bone. In some embodiments, a scaffold, or portion or component thereof, comprises substantially pure hydroxyapatite.

Composite

A scaffold, or portion or component thereof, can comprise a composite material comprising at least two components described above. As an example, a composite scaffold material can comprise at least three, at least four, at least five, at least six, at least seven, at least eight, at least nine, at least ten, or more, components. The plurality of components can be homogenously mixed throughout the scaffold, heterologously mixed throughout the scaffold, or separated into different layers of the scaffold, or a combination thereof.

For example, a scaffold, or portion or component thereof, can be formed in whole or in part of polycaprolactone or a mixture, composite, or derivative thereof. Polycaprolactone can be a particularly useful material where the scaffolds can be prepared by the methods described in U.S. Pat Pub No. 2003/0069718, U.S. Pat Pub No. 2006/0276925, U.S. Pat Pub No. 2008/0195211, U.S. Pat Pub No. 2008/0215093, or U.S. Patent application Ser. No. 13/036,470, all are incorporated herein by reference in their entireties.

Metallic

As described herein, a scaffold can be a metallic scaffold or comprise a metallic material (e.g., Ti). As another example the metallic scaffold can be a biocompatible metallic scaffold. As another example the metallic scaffold can be a titanium (Ti) scaffold. As another example the Ti scaffold can be a Ti alloy scaffold. As another example, a Ti alloy can be Ti-35Nb-5Ta-7Zr, or TNZT.

A scaffold or matrix, as described herein, can include one or more components fabricated in whole or in part from a metallic material, such as titanium or stainless steel. Suitable metallic scaffold materials are discussed in, for example, Alvarez et al. 2009 Materials 2, 790-832.

As described herein, the metal scaffold can be treated with physical or chemical methods to impart roughness to the surface. As another example, the treatment can impart submicron- or nano-roughness to the metal surface. As another example, the metal scaffold can be treated with an alkaline solution. As another example, the alkaline solution can be NaOH or KOH. Suitable treatments for metallic scaffold materials are discussed in, for example, Alvarez et al. 2009 Materials 2, 790-832.

Biocompatible

Scaffold materials can be biocompatible materials that generally form a porous, microcellular matrix, which can provide a physical support or an adhesive substrate for introducing bioactive agents or cells during fabrication, culturing, or in vivo implantation.

A scaffold comprising a matrix material can be biocompatible. Generally, a biocompatible material can be one which stimulates at most only a mild, often transient, implantation response, as opposed to a severe or escalating response. A biodegradable or degradable material can be generally understood to decompose under normal in vivo physiological conditions into components which can be metabolized or excreted.

A scaffold comprising a matrix material can be biodegradable. Material biodegradability can provide for absorption of the matrix by the surrounding tissues or can eliminate the necessity of a surgical removal. The rate at which degradation occurs can coincide as much as possible with the rate of mineral formation. Thus, while the mineral coating is fabricating their own natural structure around themselves, the scaffold or components thereof can provide structural integrity and eventually break down leaving the mineral which can assume the mechanical load. One or more scaffold materials can be modified so as to increase biodegradability. For example, polycaprolactone (PCL) is a biodegradable polyester by hydrolysis of its ester linkages in physiological conditions, and can be further modified with ring opening polymerization to increase its biodegradability.

In some embodiments, the scaffold or matrix material comprises a negative charge, which can promote the deposition of the calcium containing material. The negative charge can be provided by any moiety present on the scaffold, for example a carboxylate group, as is present in poly(D,L-lactide-co-glycolide) (PLG).

In some embodiments, the scaffold or matrix material provided herein can be formed from polycaprolactone, a biocompatible and biodegradable polymer. However, other polymers are known to be biocompatible, and can be used for the scaffolds described herein. Nonlimiting examples of suitable biodegradable materials can include polycaprolactone, polylactide, polyglycolide, poly(lactide-glycolide), poly(propylene fumarate), poly(caprolactone fumarate), polyethylene glycol, poly(glycolide-co-caprolactone), polysaccharides (e.g., alginate), chitosan, polyphosphazene, polyacrylate, polyethylene oxide-polypropylene glycol block copolymer, fibrin, collagen, fibronectin, polyvinylpyrrolidone, hyaluronic acid, polycarbonates, polyamides, polyanhydrides, polyamino acids, polyortho esters, polyacetals, polycyanoacrylates, polyurethanes, polyacrylates, ethylene-vinyl acetate polymers or other acyl substituted cellulose acetates or derivatives thereof, or analogs, mixtures, combinations or derivatives of any of the above.

Pores.

In some embodiments, a scaffold, or portion or component thereof, comprises a material having a porous microstructure. Pores of a scaffold, or portion or component thereof, can mimic internal bone structure, allow adherence of cells, provide an open volume for seeding of cells, provide an open volume for growth factors or other additives, allow adherence of another matrix layer, serve as conduits for vascularization, provide internal bone features, or facilitate perfusion. A scaffold material with a high porosity and an adequate pore size is preferred so as to facilitate mineralization, cell introduction, or diffusion throughout the whole structure of both cells and nutrients. It is understood that the pores of a scaffold material can have the same, approximately the same, or different average diameters between different components or portions of a scaffold.

Pores of a scaffold material can be engineered to be of various diameters. For example, the pores of a scaffold material can have a diameter range from micrometers to millimeters. As another example, the pores of the matrix material can have a diameter of about 2 µm to about 600 µm. As another example, the pores of the matrix material can have a diameter of about 150 µm, about 200 µm, about 250 µm, about 300 µm, about 350 µm, about 400 µm, about 450 µm, about 500 µm, about 550 µm, or about 600 µm. It is understood that recitation of the above discrete values includes a range between each recited value.

As described herein, the scaffold or matrix material can have larger pore structures and smaller pore structures.

As described herein, the larger pore structures can be at least about 200 µm. For example, the larger pore structure can be at least about 200 µm; at least about 225 µm; at least about 250 µm; at least about 275 µm; at least about 300 µm; at least about 325 µm; at least about 350 µm; at least about 375 µm; at least about 400 µm; at least about 425 µm; at least about 450 µm; at least about 475 µm; at least about 500 µm; at least about 525 µm; at least about 550 µm; at least about 575 µm; or at least about 600 µm. It is understood that recitation of the above discrete values includes a range between each recited value.

As described herein, the larger pore structures can be at about 200 µm; about 225 µm; about 250 µm; about 275 µm; about 300 µm; about 325 µm; about 350 µm; about 375 µm; about 400 µm; about 425 µm; about 450 µm; about 475 µm; about 500 µm; about 525 µm; about 550 µm; about 575 µm; or about 600 µm. It is understood that recitation of the above discrete values includes a range between each recited value.

As described herein, the smaller pore structures can be at least about 2 µm. For example, the smaller pore structure can be at least about 2 µm; at least about 3 µm; at least about 4 µm; at least about 5 µm; at least about 6 µm; at least about 7 µm; at least about 8 µm; at least about 9 µm; at least about 10 µm; at least about 11 µm; at least about 12 µm; at least about 13 µm; at least about 14 µm; at least about 15; at least about 16 µm; at least about 17 µm; at least about 18 µm; at least about 19 µm; at least about 20 µm; at least about 21 µm; at least about 22 µm; at least about 23 µm; at least about 24 µm; at least about 25 µm; at least about 26 µm; at least about 27 µm; at least about 28 µm; at least about 29 µm; at least about 30 µm; at least about 31 µm; at least about 32 µm; at least about 33 µm; at least about 34 µm; at least about 35 µm; at least about 36 µm; at least about 37 µm; at least about 38 µm; at least about 39 µm; at least about 40 µm; at least about 41 µm; at least about 42 µm; at least about 43 µm; at least about 44 µm; at least about 45 µm; at least about 46 µm; at least about 47 µm; at least about 48 µm; at least about 49 µm; at least about 50 µm; at least about 51 µm; at least about 52 µm; at least about 53 µm; at least about 54 µm; at least about 55 µm; at least about 56 µm; at least about 57 µm; at least about 58 µm; at least about 59 µm; at least about 60 µm; at least about 61 µm; at least about 62 µm; at least about 63 µm; at least about 64 µm; at least about 65 µm; at least about 66 µm; at least about 67 µm; at least about 68 µm; at least about 69 µm; at least about 70 µm; at least about 71 µm; at least about 72 µm; at least about 73 µm; at least about 74 µm; at least about 75 µm; at least about 76 µm; at least about 77 µm; at least about 78 µm; at least about 79 µm; at least about 80 µm; at least about 81 µm; at least about 82 µm; at least about 83 µm; at least about 84 µm; at least about 85 µm; at least about 86 µm; at least about 87 µm; at least about 88 µm; at least about 89 µm; at least about 90 µm; at least about 91 µm; at least about 92 µm; at least about 93 µm; at least about 94 µm; at least about 95 µm; at least about 96 µm; at least about 97 µm; at least about 98 µm; at least about 99 µm; at least about 100 µm; at least about 101 µm; at least about 102 µm; at least about 103 µm; at least about 104 µm; at least about 105 µm; at least about 106 µm; at least about 107 µm; at least about 108 µm; at least about 109 µm; at least about 110 µm; at least about 111 µm; at least about 112 µm; at least about 113 µm; at least about 114 µm; at least about 115; at least about 116 µm; at least about 117 µm; at least about 118 µm; at least about 119 µm; at least about 120 µm; at least about 121 µm; at least about 122 µm; at least about 123 µm; at least about 124 µm; at least about 125 µm; at least about 126 µm; at least about 127 µm; at least about 128 µm; at least about 129 µm; at least about 130 µm; at least about 131 µm; at least about 132 µm; at least about 133 µm; at least about 134 µm; at least about 135 µm; at least about 136 µm; at least about 137 µm; at least about 138 µm; at least about 139 µm; at least about 140 µm; at least about 141 µm; at least about 142 µm; at least about 143 µm; at least about 144 µm; at least about 145 µm; at least about 146 µm; at least about 147 µm; at least about 148 µm; at least about 149 µm; at least about 150 µm; at least about 151 µm; at least about 152 µm; at least about 153 µm; at least about 154 µm; at least about 155 µm; at least about 156 µm; at least about 157 µm; at least about 158 µm; at least about 159 µm; at least about 160 µm; at least about 161 µm; at least about 162 µm; at least about 163 µm; at least about 164 µm; at least about 165 µm; at least about 166 µm; at least about 167 µm; at least about 168 µm; at least about 169 µm; at least about 170 µm; at least about 171 µm; at least about 172 µm; at least about 173 µm; at least about 174 µm; at least about 175 µm; at least about 176 µm; at least about 177 µm; at least about 178 µm; at least about 179 µm; at least about 180 µm; at least about 181 µm; at least about 182 µm; at least about 183 µm; at least about 184 µm; at least about 185 µm; at least about 186 µm; at least about 187 µm; at least about 188 µm; at least about 189 µm; at least about 190 µm; at least about 191 µm; at least about 192 µm; at least about 193 µm; at least about 194 µm; at least about 195 µm; at least about 196 µm; at least about 197 µm; at least about 198 µm; at least about 199 µm; or at least about 200 µm. It is understood that recitation of the above discrete values includes a range between each recited value.

As described herein, the smaller pore structures can be about 2 µm; about 3 µm; about 4 µm; about 5 µm; about 6 µm; about 7 µm; about 8 µm; about 9 µm, about 10 µm, about 11 µm, about 12 µm, about 13 µm, about 14 µm; about 15; about 16 µm; about 17 µm; about 18 µm; about 19 µm; about 20 µm; about 21 µm; about 22 µm; about 23 µm; about 24 µm; about 25 µm; about 26 µm; about 27 µm; about 28 µm; about 29 µm; about 30 µm; about 31 µm; about 32 µm; about 33 µm; about 34 µm; about 35 µm; about 36 µm; about 37 µm; about 38 µm; about 39 µm; about 40 µm; about 41 µm; about 42 µm; about 43 µm; about 44 µm; about 45 µm; about 46 µm; about 47 µm; about 48 µm; about 49 µm; about 50 µm; about 51 µm; about 52 µm; about 53 µm; about 54 µm; about 55 µm; about 56 µm; about 57 µm; about 58 µm; about 59 µm; about 60 µm; about 61 µm; about 62 µm; about 63 µm; about 64 µm; about 65 µm; about 66 µm; about 67 µm; about 68 µm; about 69 µm; about 70 µm; about 71 µm; about 72 µm; about 73 µm; about 74 µm; about 75 µm; about 76 µm; about 77 µm; about 78 µm; about 79 µm; about 80 µm; about 81 µm; about 82 µm; about 83 µm; about 84 µm; about 85 µm; about 86 µm; about 87 µm; about 88 µm; about 89 µm; about 90 µm; about 91 µm; about 92 µm; about 93 µm; about 94 µm; about 95 µm; about 96 µm; about 97 µm; about 98 µm; about 99 µm; about 100 µm; about 101 µm; about 102 µm; about 103 µm; about 104 µm; about 105 µm; about 106 µm; about 107 µm; about 108 µm; about 109 µm; about 110 µm; about 111 µm; about 112 µm; about 113 µm; about 114 µm; about 115; about 116 µm; about 117 µm; about 118 µm; about 119 µm; about 120 µm; about 121 µm; about 122 µm; about 123 µm; about 124 µm; about 125 µm; about 126 µm; about 127 µm; about 128 µm; about 129 µm; about 130 µm; about 131 µm; about 132 µm; about 133 µm; about 134 µm; about 135 µm; about 136 µm; about 137 µm; about 138 µm; about 139 µm; about 140 µm; about 141 µm; about 142 µm; about 143 µm; about 144 µm; about 145 µm; about 146 µm; about 147 µm; about 148 µm; about 149 µm; about 150 µm; about 151 µm; about 152 µm; about 153 µm; about 154 µm; about 155 µm; about 156 µm; about 157 µm; about 158 µm; about 159 µm; about 160 µm; about 161 µm; about 162 µm; about 163 µm; about 164 µm; about 165 µm; about 166 µm; about 167 µm; about 168 µm; about 169 µm; about 170 µm; about 171 µm; about 172 µm; about 173 µm; about 174 µm; about 175 µm; about 176 µm; about 177 µm; about 178 µm; about 179 µm; about 180 µm; about 181 µm; about 182 µm; about 183 µm; about 184 µm; about 185 µm; about 186 µm; about 187 µm; about 188 µm; about 189 µm; about 190 µm; about 191 µm; about 192 µm; about 193 µm; about 194 µm; about 195 µm; about 196 µm; about 197 µm; about 198 µm; about 199 µm; or about 200 µm. It is understood that recitation of the above discrete values includes a range between each recited value.

As described herein, the average pore volume can be about 10%; about 20%; about 30%; about 40%; about 50%; about 60%; about 70%; about 80%; or about 90%. It is understood that recitation of the above discrete values includes a range between each recited value.

Difficult to Coat Materials.

A scaffold as described herein can comprise a material that is known to be difficult to coat with a mineral coating.

A material known to be difficult to coat can be orthopedic implant materials, cardio implant materials, smooth materials, metals, polyethylene, machined surfaces, or smooth metal surfaces. Properties that can cause coating to be challenging include increased chemical resistance, smooth surface, low water absorption, or highly resistant to thermal degradation. Conventional coating methods for difficult to coat materials can include high energy, high temperature, or highly toxic chemicals.

The Examples describe exemplary methods for producing high-quality mineral coating on a primer coated PEEK scaffold using a polymer (e.g., PCL) containing coating solution to produce the primer coating. As described herein, coating PEEK has been known to be difficult to coat due to its high chemical resistance, low water absorption, smooth surface, and its high resistance to thermal degradation. Conventional PEEK coating methods involve high energy, high temperature, or highly toxic chemicals.

Materials that are difficult to coat can include metals, calcium ceramics, polymers, or biologic materials. For example, a metal material can include stainless steel, vitallium (e.g., cobalt-chromium), titanium, or gold. As another example, a calcium ceramic material can include hydroxyapatite, tricalcium phosphate, hydroxyapatite cement, or bioactive glass. As another example, polymer material can comprise silicone, carbon fiber, carbon fiber reinforced PEEK, polyetheretherketone (PRRK), polymethylmethacrylate, hard tissue replacement (HTR) polymer, polyester (e.g., Dacron, Mersilene), biodegradable polyester (e.g., polyglycolic acid, poly-I-lactic acid), polyamide (e.g., Supramid, Nylamid), polyolefin, polyethylene (e.g., Medpor), polypropylene (e.g., Prolene, Marlex), cyanoacrylate, or polytetrafluoroethylene (e.g., Teflon, Gore-Tex). As another example, a biologic material can include collagen or AlloDerm.

Surface Roughness.

As described herein, smoothness or roughness of a material can be an inherent property of the material.

As described herein, smoothness or roughness of a material can be dictated by its manufacturing method, rather than the nature of the raw material itself. For example, manufacturing processes can include flame cutting, snagging, planing, shaping, drilling, chemical milling, electric discharge machining, milling, broaching, reaming, electron beam, laser, electrochemical, boring, turning, barrel finishing, electrolyte grinding, roller burnishing, grinding, homing, electro-polishing, polishing, superfinishing, sandcasting, hot rolling, permanent mold casting, investment casting, extruding, cold rolling, drawing, or die casting.

Roughness can be measured in a unit known as Roughness Average ($R_a$). The units of $R_a$ can be, for example, in μm or μin.

Processes to smooth materials can result in surface finish with a roughness value ($R_a$) between about 0.012 μm and about 50 μm (about 0.5 μin and about 2000 μin). Processes to smooth materials can result in surface finish with a roughness value ($R_a$) between about 0.012 μm and about 200 μm. For example, a surface finish can have an R value of about 0.01 μm; about 0.012 μm, about 0.014 μm, about 0.016 μm, about 0.018 μm, about 0.02 μm, about 0.025 μm; about 0.05 μm; about 0.075 μm; about 0.1 μm; about 0.2 μm; about 0.4 μm; about 0.6 μm; about 0.8 μm; about 1 μm; about 2 μm; about 3 μm; about 4 μm; about 5 μm; about 6 μm; about 7 μm; about 8 μm; about 9 μm; about 10 μm; about 11 μm; about 12 μm; about 13 μm; about 14 μm; about 15; about 16 μm; about 17 μm; about 18 μm; about 19 μm; about 20 μm; about 21 μm; about 22 μm; about 23 μm; about 24 μm; about 25 μm; about 26 μm; about 27 μm; about 28 μm; about 29 μm; about 30 μm; about 31 μm; about 32 μm; about 33 μm; about 34 μm; about 35 μm; about 36 μm; about 37 μm; about 38 μm; about 39 μm; about 40 μm; about 41 μm; about 42 μm; about 43 μm; about 44 μm; about 45 μm; about 46 μm; about 47 μm; about 48 μm; about 49 μm; about 50 μm; about 51 μm; about 52 μm; about 53 μm; about 54 μm; about 55 μm; about 56 μm; about 57 μm; about 58 μm; about 59 μm; about 60 μm; about 61 μm; about 62 μm; about 63 μm; about 64 μm; about 65 μm; about 66 μm; about 67 μm; about 68 μm; about 69 μm; about 70 μm; about 71 μm; about 72 μm; about 73 μm; about 74 μm; about 75 μm; about 76 μm; about 77 μm; about 78 μm; about 79 μm; about 80 μm; about 81 μm; about 82 μm; about 83 μm; about 84 μm; about 85 μm; about 86 μm; about 87 μm; about 88 μm; about 89 μm; about 90 μm; about 91 μm; about 92 μm; about 93 μm; about 94 μm; about 95 μm; about 96 μm; about 97 μm; about 98 μm; about 99 μm; about 100 μm; about 101 μm; about 102 μm; about 103 μm; about 104 μm; about 105 μm; about 106 μm; about 107 μm; about 108 μm; about 109 μm; about 110 μm; about 111 μm; about 112 μm; about 113 μm; about 114 μm; about 115; about 116 μm; about 117 μm; about 118 μm; about 119 μm; about 120 μm; about 121 μm; about 122 μm; about 123 μm; about 124 μm; about 125 μm; about 126 μm; about 127 μm; about 128 μm; about 129 μm; about 130 μm; about 131 μm; about 132 μm; about 133 μm; about 134 μm; about 135 μm; about 136 μm; about 137 μm; about 138 μm; about 139 μm; about 140 μm; about 141 μm; about 142 μm; about 143 μm; about 144 μm; about 145 μm; about 146 μm; about 147 μm; about 148 μm; about 149 μm; about 150 μm; about 151 μm; about 152 μm; about 153 μm; about 154 μm; about 155 μm; about 156 μm; about 157 μm; about 158 μm; about 159 μm; about 160 μm; about 161 μm; about 162 μm; about 163 μm; about 164 μm; about 165 μm; about 166 μm; about 167 μm; about 168 μm; about 169 μm; about 170 μm; about 171 μm; about 172 μm; about 173 μm; about 174 μm; about 175 μm; about 176 μm; about 177 μm; about 178 μm; about 179 μm; about 180 μm; about 181 μm; about 182 μm; about 183 μm; about 184 μm; about 185 μm; about 186 μm; about 187 μm; about 188 μm; about 189 μm; about 190 μm; about 191 μm; about 192 μm; about 193 μm; about 194 μm; about 195 μm; about 196 μm; about 197 μm; about 198 μm; about 199 μm; or about 200 μm. It is understood that recitation of the above discrete values includes a range between each recited value. It is understood that recitation of the above discrete values includes a range between each recited value.

A scaffold, a matrix material, or a portion thereof can have an average surface roughness value. As described herein, the average surface roughness ($R_a$) can be about 0.01 μm; about 0.012 μm; about 0.014 μm; about 0.016 μm; about 0.018 μm; about 0.02 μm; about 0.025 μm; about 0.05 μm; about 0.075 μm; about 0.1 μm; about 0.2 μm; about 0.4 μm; about 0.6 μm; about 0.8 μm; about 1 μm; about 2 μm; about 3 μm; about 4 μm; about 5 μm; about 6 μm; about 7 μm; about 8 μm; about 9 μm; about 10 μm; about 11 μm; about 12 μm; about 13 μm; about 14 μm; about 15; about 16 μm; about 17 μm; about 18 μm; about 19 μm; about 20 μm; about 21 μm; about 22 μm; about 23 μm; about 24 μm; about 25 μm; about 26 μm; about 27 μm; about 28 μm; about 29 μm; about 30 μm; about 31 μm; about 32 μm; about 33 μm; about 34 μm; about 35 μm; about 36 μm; about 37 μm; about 38 μm; about 39 μm; about 40 μm; about 41 μm; about 42 μm; about 43 μm; about 44 μm; about 45 μm; about 46 μm; about 47 μm; about 48 μm; about 49 μm; about 50 μm; about 51 μm; about 52 μm; about 53 μm; about 54 μm; about 55 μm; about 56 μm; about 57 μm; about 58 μm; about 59 μm; about 60 μm; about 61 μm; about 62 μm; about 63 μm; about 64 μm; about 65 μm; about 66 μm; about 67 μm; about 68 μm; about 69 μm; about 70 μm; about 71 μm; about 72 μm; about 73 μm; about 74 μm; about 75 μm; about 76 μm; about 77 μm; about 78 μm; about 79 μm; about 80 μm; about 81 μm; about 82 μm; about 83 μm; about 84 μm; about 85 μm; about 86 μm; about 87 μm; about 88 μm; about 89 μm; about 90 μm; about 91 μm; about 92 μm; about 93 μm; about 94 μm; about 95 μm; about 96 μm; about 97 μm; about 98 μm; about 99 μm; about 100 μm; about 101 μm; about 102 μm; about 103 μm; about 104 μm; about 105 μm; about 106 μm; about 107 μm; about 108 μm; about 109 μm; about 110 μm; about 111 μm; about 112 μm; about 113 μm; about 114 μm; about 115; about 116 μm; about 117 μm; about 118 μm; about 119 μm; about 120 μm; about 121 μm; about 122 μm; about 123 μm; about 124 μm; about 125 μm; about 126 μm; about 127 μm; about 128 μm; about 129 μm; about 130 μm; about 131 μm; about 132 μm; about 133 μm; about 134 μm; about 135 μm; about 136 μm; about 137 μm; about 138 μm; about 139 μm; about 140 μm; about 141 μm; about 142 μm; about 143 μm; about 144 μm; about 145 μm; about 146 μm; about 147 μm; about 148 μm; about 149 μm; about 150 μm; about 151 μm; about 152 μm; about 153 μm; about 154 μm; about 155 μm; about 156 μm; about 157 μm; about 158 μm; about 159 μm; about 160 μm; about 161 μm; about 162 μm; about 163 μm; about 164 μm; about 165 μm; about 166 μm; about 167 μm; about 168 μm; about 169 μm; about 170 μm; about 171 μm; about 172 μm; about 173 μm; about 174 μm; about 175 μm; about 176 μm; about 177 μm; about 178 μm; about 179 μm; about 180 μm; about 181 μm; about 182 μm; about 183 μm; about 184 μm; about 185 μm; about 186 μm; about 187 μm; about 188 μm; about 189 μm; about 190 μm; about 191 μm; about 192 μm; about 193 μm; about 194 μm; about 195 μm;

about 196 μm; about 197 μm; about 198 μm; about 199 μm; or about 200 μm. It is understood that recitation of the above discrete values includes a range between each recited value.

Macrochannel.

As described herein, the scaffold or matrix material can have macrochannel structures. For example, the macrochannel structure can be at least about 10 μm. As another example, the macrochannel structure can be at least about 100 μm.

As another example, the macrochannel structure can be at least about 10 μm; at least about 20 μm; at least about 30 μm; at least about 40 μm; at least about 50 μm; at least about 60 μm; at least about 70 μm; at least about 80 μm; at least about 90 μm; at least about 100 μm; at least about 110 μm; at least about 120 μm; at least about 130 μm; at least about 140 μm; at least about 150; at least about 160 μm; at least about 170 μm; at least about 180 μm; at least about 190 μm; at least about 200 μm; at least about 210 μm; at least about 220 μm; at least about 230 μm; at least about 240 μm; at least about 250; at least about 260 μm; at least about 270 μm; at least about 280 μm; at least about 290 μm; at least about 300 μm; at least about 310 μm; at least about 320 μm; at least about 330 μm; at least about 340 μm; at least about 350; at least about 360 μm; at least about 370 μm; at least about 380 μm; at least about 390 μm; at least about 400 μm; at least about 410 μm; at least about 420 μm; at least about 430 μm; at least about 440 μm; at least about 450; at least about 460 μm; at least about 470 μm; at least about 480 μm; at least about 490 μm; at least about 500 μm; at least about 510 μm; at least about 520 μm; at least about 530 μm; at least about 540 μm; at least about 550; at least about 560 μm; at least about 570 μm; at least about 580 μm; at least about 590 μm; at least about 600 μm; at least about 610 μm; at least about 620 μm; at least about 630 μm; at least about 640 μm; at least about 650; at least about 660 μm; at least about 670 μm; at least about 680 μm; at least about 690 μm; at least about 700 μm; at least about 710 μm; at least about 720 μm; at least about 730 μm; at least about 740 μm; at least about 750; at least about 760 μm; at least about 770 μm; at least about 780 μm; at least about 790 μm; at least about 800 μm; at least about 810 μm; at least about 820 μm; at least about 830 μm; at least about 840 μm; at least about 850; at least about 860 μm; at least about 870 μm; at least about 880 μm; at least about 890 μm; at least about 900 μm; at least about 910 μm; at least about 920 μm; at least about 930 μm; at least about 940 μm; at least about 950; at least about 960 μm; at least about 970 μm; at least about 980 μm; at least about 990 μm; or at least about 1000 μm. It is understood that recitation of the above discrete values includes a range between each recited value.

As another example, the macrochannel structure can be about 10 μm; about 20 μm; about 30 μm; about 40 μm; about 50 μm; about 60 μm; about 70 μm; about 80 μm; about 90 μm; about 100 μm; about 110 μm; about 120 μm; about 130 μm; about 140 μm; about 150; about 160 μm; about 170 μm; about 180 μm; about 190 μm; about 200 μm; about 210 μm; about 220 μm; about 230 μm; about 240 μm; about 250; about 260 μm; about 270 μm; about 280 μm; about 290 μm; about 300 μm; about 310 μm; about 320 μm; about 330 μm; about 340 μm; about 350; about 360 μm; about 370 μm; about 380 μm; about 390 μm; about 400 μm; about 410 μm; about 420 μm; about 430 μm; about 440 μm; about 450; about 460 μm; about 470 μm; about 480 μm; about 490 μm; about 500 μm; about 510 μm; about 520 μm; about 530 μm; about 540 μm; about 550; about 560 μm; about 570 μm; about 580 μm; about 590 μm; about 600 μm; about 610 μm; about 620 μm; about 630 μm; about 640 μm; about 650; about 660 μm; about 670 μm; about 680 μm; about 690 μm; about 700 μm; about 710 μm; about 720 μm; about 730 μm; about 740 μm; about 750; about 760 μm; about 770 μm; about 780 μm; about 790 μm; about 800 μm; about 810 μm; about 820 μm; about 830 μm; about 840 μm; about 850; about 860 μm; about 870 μm; about 880 μm; about 890 μm; about 900 μm; about 910 μm; about 920 μm; about 930 μm; about 940 μm; about 950; about 960 μm; about 970 μm; about 980 μm; about 990 μm; or about 1000 μm. It is understood that recitation of the above discrete values includes a range between each recited value.

Modified Simulated Body Fluid

A modified simulated body fluid as described herein can be a solution including ionic constituents of blood plasma. In some embodiments, the modified simulated body fluid does not comprise organic components. Inorganic minerals suitable for producing a calcium-containing mineral coating include various bone mineral ions, such as, but not limited to calcium and phosphate and combinations of bone mineral ions, such as calcium-phosphates. A modified simulated body fluid can be as described in U.S. application Ser. Nos. 13/407,441; 13/879,178; and 13/036,470 and are incorporated by reference.

A modified simulated body fluid as described herein can be used to mineral coat a scaffold. For example, the scaffold can be immersed and incubated in a modified simulated body fluid. As another example, the modified simulated body fluid can be replaced, replenished, or removed and added at least about once a day; at least about twice per day; or at least about three times per day. As another example, the modified simulated body fluid can be replaced at least about once every day; at least about once every two days; at least once every three days; at least once every four days; at least once every five days; at least once every six days; or at least once every seven days.

As described herein, a modified simulated body fluid can be a solution of ionic constituents of blood plasma, with double the concentrations of calcium and phosphate ions.

As described herein, a modified simulated body fluid can be a solution comprising NaCl, KCl, $MgCl_2$, $MgSO_4$, $NaHCO_3$, $CaCl_2$, and $KH_2PO_4$.

A modified simulated body fluid can include at least about 1 mM NaCl. For example, a modified simulated body fluid can include at least about 1 mM NaCl; at least about 10 mM NaCl; at least about 20 mM NaCl; at least about 30 mM NaCl; at least about 40 mM NaCl; at least about 50 mM NaCl; at least about 60 mM NaCl; at least about 70 mM NaCl; at least about 80 mM NaCl; at least about 90 mM NaCl; at least about 100 mM NaCl; at least about 110 mM NaCl; at least about 120 mM NaCl; at least about 130 mM NaCl; at least about 140 mM NaCl; at least about 150 mM NaCl; at least about 160 mM NaCl; at least about 170 mM NaCl; at least about 180 mM NaCl; at least about 190 mM NaCl; at least about 200 mM NaCl; at least about 300 mM NaCl; at least about 400 mM NaCl; at least about 500 mM NaCl; at least about 600 mM NaCl; at least about 700 mM NaCl; at least about 800 mM NaCl; at least about 900 mM NaCl; at least about 1000 mM NaCl; at least about 1100 mM NaCl; at least about 1200 mM NaCl; at least about 1300 mM NaCl; at least about 1400 mM NaCl; at least about 1500 mM NaCl; at least about 1600 mM NaCl; at least about 1700 mM NaCl; at least about 1800 mM NaCl; at least about 1900 mM NaCl; or at least about 2000 mM NaCl. It is understood that recitation of the above discrete values includes a range between each recited value.

As another example, a modified simulated body fluid can include about 1 mM NaCl, about 10 mM NaCl; about 20 mM NaCl; about 30 mM NaCl; about 40 mM NaCl; about 50 mM NaCl; about 60 mM NaCl; about 70 mM NaCl; about 80 mM NaCl; about 90 mM NaCl; about 100 mM NaCl; about 110 mM NaCl; about 120 mM NaCl; about 130 mM NaCl; about 140 mM NaCl; about 150 mM NaCl; about 160 mM NaCl; about 170 mM NaCl; about 180 mM NaCl; about 190 mM NaCl; about 200 mM NaCl; about 300 mM NaCl; about 400 mM NaCl; about 500 mM NaCl; about 600 mM NaCl; about 700 mM NaCl; about 800 mM NaCl; about 900 mM NaCl; about 1000 mM NaCl; about 1100 mM NaCl; about 1200 mM NaCl; about 1300 mM NaCl; about 1400 mM NaCl; about 1500 mM NaCl; about 1600 mM NaCl; about 1700 mM NaCl; about 1800 mM NaCl; about 1900 mM NaCl; or about 2000 mM NaCl. It is understood that recitation of the above discrete values includes a range between each recited value.

A modified simulated body fluid can include at least about 0.4 mM KCl. For example, a modified simulated body fluid can include at least about 0.4 mM KCl; at least about 1 mM KCl; at least about 2 mM KCl; at least about 3 mM KCl; at least about 4 mM KCl; at least about 5 mM KCl; at least about 6 mM KCl; at least about 7 mM KCl; at least about 8 mM KCl; at least about 9 mM KCl; at least about 10 mM KCl; at least about 11 mM KCl; at least about 12 mM KCl; at least about 13 mM KCl; at least about 14 mM KCl; at least about 15 mM KCl; at least about 16 mM KCl; at least about 17 mM KCl; at least about 18 mM KCl; at least about 19 mM KCl; at least about 20 mM KCl; at least about 21 mM KCl; at least about 22 mM KCl; at least about 23 mM KCl; at least about 24 mM KCl; at least about 25 mM KCl; at least about 26 mM KCl; at least about 27 mM KCl; at least about 28 mM KCl; at least about 29 mM KCl; at least about 30 mM KCl; at least about 31 mM KCl; at least about 32 mM KCl; at least about 33 mM KCl; at least about 34 mM KCl; at least about 35 mM KCl; at least about 36 mM KCl; at least about 37 mM KCl; at least about 38 mM KCl; at least about 39 mM KCl; at least about 40 mM KCl; at least about 41 mM KCl; at least about 42 mM KCl; at least about 43 mM KCl; at least about 44 mM KCl; at least about 45 mM KCl; at least about 46 mM KCl; at least about 47 mM KCl; at least about 48 mM KCl; at least about 49 mM KCl; at least about 50 mM KCl; at least about 51 mM KCl; at least about 52 mM KCl; at least about 53 mM KCl; at least about 54 mM KCl; at least about 55 mM KCl; at least about 56 mM KCl; at least about 57 mM KCl; at least about 58 mM KCl; at least about 59 mM KCl; at least about 60 mM KCl; at least about 61 mM KCl; at least about 62 mM KCl; at least about 63 mM KCl; at least about 64 mM KCl; at least about 65 mM KCl; at least about 66 mM KCl; at least about 67 mM KCl; at least about 68 mM KCl; at least about 69 mM KCl; at least about 70 mM KCl; at least about 71 mM KCl; at least about 72 mM KCl; at least about 73 mM KCl; at least about 74 mM KCl; at least about 75 mM KCl; at least about 76 mM KCl; at least about 77 mM KCl; at least about 78 mM KCl; at least about 79 mM KCl; or at least about 80 mM KCl. It is understood that recitation of the above discrete values includes a range between each recited value.

As another example, a modified simulated body fluid can include about 0.4 mM KCl, about 1 mM KCl, about 2 mM KCl, about 3 mM KCl, about 4 mM KCl, about 5 mM KCl, about 6 mM KCl, about 7 mM KCl, about 8 mM KCl, about 9 mM KCl, about 10 mM KCl, about 11 mM KCl, about 12 mM KCl, about 13 mM KCl, about 14 mM KCl, about 15 mM KCl, about 16 mM KCl, about 17 mM KCl, about 18 mM KCl, about 19 mM KCl, about 20 mM KCl, about 21 mM KCl, about 22 mM KCl, about 23 mM KCl, about 24 mM KCl, about 25 mM KCl, about 26 mM KCl, about 27 mM KCl, about 28 mM KCl, about 29 mM KCl, about 30 mM KCl, about 31 mM KCl, about 32 mM KCl, about 33 mM KCl, about 34 mM KCl, about 35 mM KCl, about 36 mM KCl, about 37 mM KCl, about 38 mM KCl, about 39 mM KCl, about 40 mM; about 41 mM KCl, about 42 mM KCl, about 43 mM KCl, about 44 mM KCl, about 45 mM KCl, about 46 mM KCl, about 47 mM KCl, about 48 mM KCl, about 49 mM KCl, about 50 mM KCl, about 51 mM KCl, about 52 mM KCl, about 53 mM KCl, about 54 mM KCl, about 55 mM KCl, about 56 mM KCl, about 57 mM KCl, about 58 mM KCl, about 59 mM KCl, about 60 mM KCl, about 61 mM KCl, about 62 mM KCl, about 63 mM KCl, about 64 mM KCl, about 65 mM KCl, about 66 mM KCl, about 67 mM KCl, about 68 mM KCl, about 69 mM KCl, about 70 mM KCl, about 71 mM KCl, about 72 mM KCl, about 73 mM KCl, about 74 mM KCl, about 75 mM KCl, about 76 mM KCl, about 77 mM KCl, about 78 mM KCl, about 79 mM KCl, or about 80 mM KCl. It is understood that recitation of the above discrete values includes a range between each recited value.

A modified simulated body fluid can include at least about 0.1 mM $MgCl_2$. For example, a modified simulated body fluid can include at least about 0.1 mM $MgCl_2$, at least about 0.25 mM $MgCl_2$, at least about 0.5 mM $MgCl_2$, at least about 1 mM $MgCl_2$, at least about 1.25 mM $MgCl_2$, at least about 1.5 mM $MgCl_2$, at least about 1.75 mM $MgCl_2$, at least about 2 mM $MgCl_2$, at least about 2.25 mM $MgCl_2$, at least about 2.5 mM $MgCl_2$, at least about 2.75 mM $MgCl_2$, at least about 3 mM $MgCl_2$, at least about 3.25 mM $MgCl_2$, at least about 3.5 mM $MgCl_2$, at least about 3.75 mM $MgCl_2$, at least about 4 mM $MgCl_2$, at least about 4.25 mM $MgCl_2$, at least about 4.5 mM $MgCl_2$, at least about 4.75 mM $MgCl_2$, at least about 5 mM $MgCl_2$, at least about 5.25 mM $MgCl_2$, at least about 5.5 mM $MgCl_2$, at least about 5.75 mM $MgCl_2$, at least about 6 mM $MgCl_2$, at least about 6.25 mM $MgCl_2$, at least about 6.5 mM $MgCl_2$, at least about 6.75 mM $MgCl_2$, at least about 7 mM $MgCl_2$, at least about 7.25 mM $MgCl_2$, at least about 7.5 mM $MgCl_2$, at least about 7.75 mM $MgCl_2$, at least about 8 mM $MgCl_2$, at least about 8.25 mM $MgCl_2$, at least about 8.5 mM $MgCl_2$, at least about 8.75 mM $MgCl_2$, at least about 9 mM $MgCl_2$, at least about 9.25 mM $MgCl_2$, at least about 9.5 mM $MgCl_2$, at least about 9.75 mM $MgCl_2$, at least about 10 mM $MgCl_2$, at least about 11 mM $MgCl_2$, at least about 12 mM $MgCl_2$, at least about 13 mM $MgCl_2$, at least about 14 mM $MgCl_2$, at least about 15 mM $MgCl_2$, at least about 16 mM $MgCl_2$, at least about 17 mM $MgCl_2$, at least about 18 mM $MgCl_2$, at least about 19 mM $MgCl_2$, at least about 20 mM $MgCl_2$, at least about 21 mM $MgCl_2$, at least about 22 mM $MgCl_2$, at least about 23 mM $MgCl_2$, at least about 24 mM $MgCl_2$, at least about 25 mM $MgCl_2$, at least about 26 mM $MgCl_2$, at least about 27 mM $MgCl_2$, at least about 28 mM $MgCl_2$, at least about 29 mM $MgCl_2$, at least about 30 mM $MgCl_2$, at least about 31 mM $MgCl_2$, at least about 32 mM $MgCl_2$, at least about 33 mM $MgCl_2$, at least about 34 mM $MgCl_2$, at least about 35 mM $MgCl_2$, at least about 36 mM $MgCl_2$, at least about 37 mM $MgCl_2$, at least about 38 mM $MgCl_2$, at least about 39 mM $MgCl_2$, at least about 40 mM $MgCl_2$, at least about 41 mM $MgCl_2$, at least about 42 mM $MgCl_2$, at least about 43 mM $MgCl_2$, at least about 44 mM $MgCl_2$, at least about 45 mM $MgCl_2$, at least about 46 mM $MgCl_2$, at least about 47 mM $MgCl_2$, at least about 48 mM $MgCl_2$, at least about 49 mM $MgCl_2$, or at least about 50 mM $MgCl_2$. It is understood that recitation of the above discrete values includes a range between each recited value.

As another example, a modified simulated body fluid can include about 0.1 mM $MgCl_2$, at least about 0.25 mM $MgCl_2$, about 0.5 mM $MgCl_2$, about 1 mM $MgCl_2$, about 1.25 mM $MgCl_2$, about 1.5 mM $MgCl_2$, about 1.75 mM $MgCl_2$, about 2 mM $MgCl_2$, about 2.25 mM $MgCl_2$, about 2.5 mM $MgCl_2$, about 2.75 mM $MgCl_2$, about 3 mM $MgCl_2$, about 3.25 mM $MgCl_2$, about 3.5 mM $MgCl_2$, about 3.75 mM $MgCl_2$, about 4 mM $MgCl_2$, about 4.25 mM $MgCl_2$, about 4.5 mM $MgCl_2$, about 4.75 mM $MgCl_2$, about 5 mM $MgCl_2$, about 5.25 mM $MgCl_2$, about 5.5 mM $MgCl_2$, about 5.75 mM $MgCl_2$, about 6 mM $MgCl_2$, about 6.25 mM $MgCl_2$, about 6.5 mM $MgCl_2$, about 6.75 mM $MgCl_2$, about 7 mM $MgCl_2$, about 7.25 mM $MgCl_2$, about 7.5 mM $MgCl_2$, about 7.75 mM $MgCl_2$, about 8 mM $MgCl_2$, about 8.25 mM $MgCl_2$, about 8.5 mM $MgCl_2$, about 8.75 mM $MgCl_2$, about 9 mM $MgCl_2$, about 9.25 mM $MgCl_2$, about 9.5 mM $MgCl_2$, about 9.75 mM $MgCl_2$, about 10 mM $MgCl_2$, about 11 mM $MgCl_2$, about 12 mM $MgCl_2$, about 13 mM $MgCl_2$, about 14 mM $MgCl_2$, about 15 mM $MgCl_2$, about 16 mM $MgCl_2$, about 17 mM $MgCl_2$, about 18 mM $MgCl_2$, about 19 mM $MgCl_2$, about 20 mM $MgCl_2$, about 21 mM $MgCl_2$, about 22 mM $MgCl_2$, about 23 mM $MgCl_2$, about 24 mM $MgCl_2$, about 25 mM $MgCl_2$, about 26 mM $MgCl_2$, about 27 mM $MgCl_2$, about 28 mM $MgCl_2$, about 29 mM $MgCl_2$, about 30 mM $MgCl_2$, about 31 mM $MgCl_2$, about 32 mM $MgCl_2$, about 33 mM $MgCl_2$, about 34 mM $MgCl_2$, about 35 mM $MgCl_2$, about 36 mM $MgCl_2$, about 37 mM $MgCl_2$, about 38 mM $MgCl_2$, about 39 mM $MgCl_2$, about 40 mM $MgCl_2$, about 41 mM $MgCl_2$, about 42 mM $MgCl_2$, about 43 mM $MgCl_2$, about 44 mM $MgCl_2$, about 45 mM $MgCl_2$, about 46 mM $MgCl_2$, about 47 mM $MgCl_2$, about 48 mM $MgCl_2$, about 49 mM $MgCl_2$, or about 50 mM $MgCl_2$. It is understood that recitation of the above discrete values includes a range between each recited value.

A modified simulated body fluid can include at least about 0.05 mM $MgSO_4$. For example, a modified simulated body fluid can include at least about 0.05 mM $MgSO_4$; at least about 0.25 mM $MgSO_4$; at least about 0.5 mM $MgSO_4$; at least about 0.75 mM $MgSO_4$; at least about 1 mM $MgSO_4$; at least about 1.25 mM $MgSO_4$; at least about 1.5 mM $MgSO_4$; at least about 1.75 mM $MgSO_4$; at least about 2 mM $MgSO_4$; at least about 2.25 mM $MgSO_4$; at least about 2.5 mM $MgSO_4$; at least about 2.75 mM $MgSO_4$; at least about 3 mM $MgSO_4$; at least about 3.25 mM $MgSO_4$; at least about 3.5 mM $MgSO_4$; at least about 3.75 mM $MgSO_4$; at least about 4 mM $MgSO_4$; at least about 4.25 mM $MgSO_4$; at least about 4.5 mM $MgSO_4$; at least about 4.75 mM $MgSO_4$; at least about 5 mM $MgSO_4$; at least about 6 mM $MgSO_4$; at least about 7 mM $MgSO_4$; at least about 8 mM $MgSO_4$; at least about 9 mM $MgSO_4$; at least about 10 mM $MgSO_4$; at least about 11 mM $MgSO_4$; at least about 12 mM $MgSO_4$; at least about 13 mM $MgSO_4$; at least about 14 mM $MgSO_4$; at least about 15 mM $MgSO_4$; at least about 16 mM $MgSO_4$; at least about 17 mM $MgSO_4$; at least about 18 mM $MgSO_4$; at least about 19 mM $MgSO_4$; at least about 20 mM $MgSO_4$; at least about 21 mM $MgSO_4$; at least about 22 mM $MgSO_4$; at least about 23 mM $MgSO_4$; at least about 24 mM $MgSO_4$; at least about 25 mM $MgSO_4$; at least about 26 mM $MgSO_4$; at least about 27 mM $MgSO_4$; at least about 28 mM $MgSO_4$; at least about 29 mM $MgSO_4$; at least about 30 mM $MgSO_4$; at least about 31 mM $MgSO_4$; at least about 32 mM $MgSO_4$; at least about 33 mM $MgSO_4$; at least about 34 mM $MgSO_4$; at least about 35 mM $MgSO_4$; at least about 36 mM $MgSO_4$; at least about 37 mM $MgSO_4$; at least about 38 mM $MgSO_4$; at least about 39 mM $MgSO_4$; at least about 40 mM $MgSO_4$; at least about 41 mM $MgSO_4$; at least about 42 mM $MgSO_4$; at least about 43 mM $MgSO_4$; at least about 44 mM $MgSO_4$; at least about 45 mM $MgSO_4$; at least about 46 mM $MgSO_4$; at least about 47 mM $MgSO_4$; at least about 48 mM $MgSO_4$; at least about 49 mM $MgSO_4$; or at least about 50 mM $MgSO_4$. It is understood that recitation of the above discrete values includes a range between each recited value.

As another example, a modified simulated body fluid can include about 0.05 mM $MgSO_4$; about 0.25 mM $MgSO_4$; about 0.5 mM $MgSO_4$; about 0.75 mM $MgSO_4$; about 1 mM $MgSO_4$; about 1.25 mM $MgSO_4$; about 1.5 mM $MgSO_4$; about 1.75 mM $MgSO_4$; about 2 mM $MgSO_4$; about 2.25 mM $MgSO_4$; about 2.5 mM $MgSO_4$; about 2.75 mM $MgSO_4$; about 3 mM $MgSO_4$; about 3.25 mM $MgSO_4$; about 3.5 mM $MgSO_4$; about 3.75 mM $MgSO_4$; about 4 mM $MgSO_4$; about 4.25 mM $MgSO_4$; about 4.5 mM $MgSO_4$; about 4.75 mM $MgSO_4$; about 5 mM $MgSO_4$; about 6 mM $MgSO_4$; about 7 mM $MgSO_4$; about 8 mM $MgSO_4$; about 9 mM $MgSO_4$; about 10 mM $MgSO_4$; about 11 mM $MgSO_4$; about 12 mM $MgSO_4$; about 13 mM $MgSO_4$; about 14 mM $MgSO_4$; about 15 mM $MgSO_4$; about 16 mM $MgSO_4$; about 17 mM $MgSO_4$; about 18 mM $MgSO_4$; about 19 mM $MgSO_4$; about 20 mM $MgSO_4$; about 21 mM $MgSO_4$; about 22 mM $MgSO_4$; about 23 mM $MgSO_4$; about 24 mM $MgSO_4$; about 25 mM $MgSO_4$; about 26 mM $MgSO_4$; about 27 mM $MgSO_4$; about 28 mM $MgSO_4$; about 29 mM $MgSO_4$; about 30 mM $MgSO_4$; about 31 mM $MgSO_4$; about 32 mM $MgSO_4$; about 33 mM $MgSO_4$; about 34 mM $MgSO_4$; about 35 mM $MgSO_4$; about 36 mM $MgSO_4$; about 37 mM $MgSO_4$; about 38 mM $MgSO_4$; about 39 mM $MgSO_4$; about 40 mM $MgSO_4$; about 41 mM $MgSO_4$; about 42 mM $MgSO_4$; about 43 mM $MgSO_4$; about 44 mM $MgSO_4$; about 45 mM $MgSO_4$; about 46 mM $MgSO_4$; about 47 mM $MgSO_4$; about 48 mM $MgSO_4$; about 49 mM $MgSO_4$; or about 50 mM $MgSO_4$. It is understood that recitation of the above discrete values includes a range between each recited value.

A modified simulated body fluid can include at least about 0.4 mM $NaHCO_3$. For example, a modified simulated body fluid can include at least about 0.4 mM $NaHCO_3$; at least about 0.6 mM $NaHCO_3$; at least about 0.8 mM $NaHCO_3$; at least about 1.0 mM $NaHCO_3$; at least about 1.2 mM $NaHCO_3$; at least about 1.4 mM $NaHCO_3$; at least about 1.6 mM $NaHCO_3$; at least about 1.8 mM $NaHCO_3$; at least about 2.0 mM $NaHCO_3$; at least about 2.2 mM $NaHCO_3$; at least about 2.4 mM $NaHCO_3$; at least about 2.6 mM $NaHCO_3$; at least about 2.8 mM $NaHCO_3$; at least about 3.0 mM $NaHCO_3$; at least about 3.2 mM $NaHCO_3$; at least about 3.4 mM $NaHCO_3$; at least about 3.6 mM $NaHCO_3$; at least about 3.8 mM $NaHCO_3$; at least about 4.0 mM $NaHCO_3$; at least about 4.2 mM $NaHCO_3$; at least about 4.4 mM $NaHCO_3$; at least about 4.6 mM $NaHCO_3$; at least about 4.8 mM $NaHCO_3$; at least about 5.0 mM $NaHCO_3$; at least about 5.2 mM $NaHCO_3$; at least about 5.4 mM $NaHCO_3$; at least about 5.6 mM $NaHCO_3$; at least about 5.8 mM $NaHCO_3$; at least about 6.0 mM $NaHCO_3$; at least about 6.2 mM $NaHCO_3$; at least about 6.4 mM $NaHCO_3$; at least about 6.6 mM $NaHCO_3$; at least about 6.8 mM $NaHCO_3$; at least about 7.0 mM $NaHCO_3$; at least about 7.2 mM $NaHCO_3$; at least about 7.4 mM $NaHCO_3$; at least about 7.6 mM $NaHCO_3$; at least about 7.8 mM $NaHCO_3$; at least about 8.0 mM $NaHCO_3$; at least about 8.2 mM $NaHCO_3$; at least about 8.4 mM $NaHCO_3$; at least about 8.6 mM $NaHCO_3$; at least about 8.8 mM $NaHCO_3$; at least about 9.0 mM $NaHCO_3$; at least about 10 mM $NaHCO_3$; at least about 20 mM $NaHCO_3$; at least about 30 mM $NaHCO_3$; at least about 40 mM $NaHCO_3$; at least about 50 mM $NaHCO_3$; at least about 60 mM $NaHCO_3$; at least about 70 mM $NaHCO_3$; at least about 80 mM $NaHCO_3$; at least about 90 mM $NaHCO_3$; at least about 100 mM $NaHCO_3$; at least about 200 mM $NaHCO_3$; at least about 300 mM $NaHCO_3$; at least about 400 mM $NaHCO_3$; at least about 500 mM NaHCO$_3$; at least about 600 mM NaHCO$_3$; at least about 700 mM NaHCO$_3$; at least about 800 mM NaHCO$_3$; at least about 900 mM NaHCO$_3$; or at least about 1000 mM NaHCO$_3$. It is understood that recitation of the above discrete values includes a range between each recited value.

As another example, a modified simulated body fluid can include about 0.4 mM NaHCO$_3$; about 0.6 mM NaHCO$_3$; about 0.8 mM NaHCO$_3$; about 1.0 mM NaHCO$_3$; about 1.2 mM NaHCO$_3$; about 1.4 mM NaHCO$_3$; about 1.6 mM NaHCO$_3$; about 1.8 mM NaHCO$_3$; about 2.0 mM NaHCO$_3$; about 2.2 mM NaHCO$_3$; about 2.4 mM NaHCO$_3$; about 2.6 mM NaHCO$_3$; about 2.8 mM NaHCO$_3$; about 3.0 mM NaHCO$_3$; about 3.2 mM NaHCO$_3$; about 3.4 mM NaHCO$_3$; about 3.6 mM NaHCO$_3$; about 3.8 mM NaHCO$_3$; about 4.0 mM NaHCO$_3$; about 4.2 mM NaHCO$_3$; about 4.4 mM NaHCO$_3$; about 4.6 mM NaHCO$_3$; about 4.8 mM NaHCO$_3$; about 5.0 mM NaHCO$_3$; about 5.2 mM NaHCO$_3$; about 5.4 mM NaHCO$_3$; about 5.6 mM NaHCO$_3$; about 5.8 mM NaHCO$_3$; about 6.0 mM NaHCO$_3$; about 6.2 mM NaHCO$_3$; about 6.4 mM NaHCO$_3$; about 6.6 mM NaHCO$_3$; about 6.8 mM NaHCO$_3$; about 7.0 mM NaHCO$_3$; about 7.2 mM NaHCO$_3$; about 7.4 mM NaHCO$_3$; about 7.6 mM NaHCO$_3$; about 7.8 mM NaHCO$_3$; about 8.0 mM NaHCO$_3$; about 8.2 mM NaHCO$_3$; about 8.4 mM NaHCO$_3$; about 8.6 mM NaHCO$_3$; about 8.8 mM NaHCO$_3$; about 9.0 mM NaHCO$_3$; about 10 mM NaHCO$_3$; about 20 mM NaHCO$_3$; about 30 mM NaHCO$_3$; about 40 mM NaHCO$_3$; about 50 mM NaHCO$_3$; about 60 mM NaHCO$_3$; about 70 mM NaHCO$_3$; about 80 mM NaHCO$_3$; about 90 mM NaHCO$_3$; about 100 mM NaHCO$_3$; about 200 mM NaHCO$_3$; about 300 mM NaHCO$_3$; about 400 mM NaHCO$_3$; about 500 mM NaHCO$_3$; about 600 mM NaHCO$_3$; about 700 mM NaHCO$_3$; about 800 mM NaHCO$_3$; about 900 mM NaHCO$_3$; or about 1000 mM NaHCO$_3$. It is understood that recitation of the above discrete values includes a range between each recited value.

A modified simulated body fluid can include at least about 0.5 mM CaCl$_2$. For example, a modified simulated body fluid can include at least about 0.5 mM CaCl$_2$, at least about 1.0 mM CaCl$_2$, at least about 1.5 mM CaCl$_2$, at least about 2.0 mM CaCl$_2$, at least about 2.5 mM CaCl$_2$, at least about 3.0 mM CaCl$_2$, at least about 3.5 mM CaCl$_2$, at least about 4.0 mM CaCl$_2$, at least about 4.5 mM CaCl$_2$, at least about 5.0 mM CaCl$_2$, at least about 5.5 mM CaCl$_2$, at least about 6.0 mM CaCl$_2$, at least about 6.5 mM CaCl$_2$, at least about 7.0 mM CaCl$_2$, at least about 7.5 mM CaCl$_2$, at least about 8.0 mM CaCl$_2$, at least about 8.5 mM CaCl$_2$, at least above 9.0 mM CaCl$_2$, at least about 9.5 mM CaCl$_2$, at least above 10.0 mM CaCl$_2$, at least about 10.5 mM CaCl$_2$, at least above 11.0 mM CaCl$_2$, at least about 11.5 mM CaCl$_2$, at least above 12.0 mM CaCl$_2$, at least about 12.5 mM CaCl$_2$, at least about 13.0 mM CaCl$_2$, at least about 13.5 mM CaCl$_2$, at least about 14.0 mM CaCl$_2$, at least about 14.5 mM CaCl$_2$, at least about 15.0 mM CaCl$_2$, at least about 15.5 mM CaCl$_2$, at least about 16.0 mM CaCl$_2$, at least about 16.5 mM CaCl$_2$, at least about 17.0 mM CaCl$_2$, at least about 17.5 mM CaCl$_2$, at least about 18.0 mM CaCl$_2$, at least about 18.5 mM CaCl$_2$, at least about 19.0 mM CaCl$_2$, at least about 19.5 mM CaCl$_2$, at least about 20.0 mM CaCl$_2$, at least about 25 mM CaCl$_2$, at least about 30 mM CaCl$_2$, at least about 35 mM CaCl$_2$, at least about 40 mM CaCl$_2$, at least about 45 mM CaCl$_2$, or at least about 50 mM CaCl$_2$. It is understood that recitation of the above discrete values includes a range between each recited value.

As another example, a modified simulated body fluid can include about 0.5 mM CaCl$_2$, about 1.0 mM CaCl$_2$, about 1.5 mM CaCl$_2$, about 2.0 mM CaCl$_2$; about 2.5 mM CaCl$_2$, about 3.0 mM CaCl$_2$, about 3.5 mM CaCl$_2$, about 4.0 mM CaCl$_2$, about 4.5 mM CaCl$_2$, about 5.0 mM CaCl$_2$, about 5.5 mM CaCl$_2$, about 6.0 mM CaCl$_2$, about 6.5 mM CaCl$_2$, about 7.0 mM CaCl$_2$, about 7.5 mM CaCl$_2$; about 8.0 mM CaCl$_2$, about 8.5 mM CaCl$_2$, about 9.0 mM CaCl$_2$, about 9.5 mM CaCl$_2$, about 10.0 mM CaCl$_2$, about 10.5 mM CaCl$_2$, about 11.0 mM CaCl$_2$; about 11.5 mM CaCl$_2$, about 12.0 mM CaCl$_2$, about 12.5 mM CaCl$_2$, about 13.0 mM CaCl$_2$, about 13.5 mM CaCl$_2$, about 14.0 mM CaCl$_2$, about 14.5 mM CaCl$_2$; about 15.0 mM CaCl$_2$, about 15.5 mM CaCl$_2$, about 16.0 mM CaCl$_2$, about 16.5 mM CaCl$_2$, about 17.0 mM CaCl$_2$, about 17.5 mM CaCl$_2$, about 18.0 mM CaCl$_2$; about 18.5 mM CaCl$_2$, about 19.0 mM CaCl$_2$, about 19.5 mM CaCl$_2$, about 20.0 mM CaCl$_2$, about 25 mM CaCl$_2$, about 30 mM CaCl$_2$, about 35 mM CaCl$_2$, about 40 mM CaCl$_2$, about 45 mM CaCl$_2$, or about 50 mM CaCl$_2$. It is understood that recitation of the above discrete values includes a range between each recited value.

A modified simulated body fluid can include at least about 0.2 mM KH$_2$PO$_4$. For example, a modified simulated body fluid can include at least about 0.2 mM KH$_2$PO$_4$; at least about 0.4 mM KH$_2$PO$_4$; at least about 0.6 mM KH$_2$PO$_4$; at least about 0.8 mM KH$_2$PO$_4$; at least about 1.0 mM KH$_2$PO$_4$; at least about 1.2 mM KH$_2$PO$_4$; at least about 1.4 mM KH$_2$PO$_4$; at least about 1.6 mM KH$_2$PO$_4$; at least about 1.8 mM KH$_2$PO$_4$; at least about 2.0 mM KH$_2$PO$_4$; at least about 2.2 mM KH$_2$PO$_4$; at least about 2.4 mM KH$_2$PO$_4$; at least about 2.6 mM KH$_2$PO$_4$; at least about 2.8 mM KH$_2$PO$_4$; at least about 3.0 mM KH$_2$PO$_4$; at least about 3.2 mM KH$_2$PO$_4$; at least about 3.4 mM KH$_2$PO$_4$; at least about 3.6 mM KH$_2$PO$_4$; at least about 3.8 mM KH$_2$PO$_4$; at least about 4.0 mM KH$_2$PO$_4$; at least about 4.2 mM KH$_2$PO$_4$; at least about 4.4 mM KH$_2$PO$_4$; at least about 4.6 mM KH$_2$PO$_4$; at least about 4.8 mM KH$_2$PO$_4$; at least about 5.0 mM KH$_2$PO$_4$; at least about 5.2 mM KH$_2$PO$_4$; at least about 5.4 mM KH$_2$PO$_4$; at least about 5.6 mM KH$_2$PO$_4$; at least about 5.8 mM KH$_2$PO$_4$; at least about 6.0 mM KH$_2$PO$_4$; at least about 6.2 mM KH$_2$PO$_4$; at least about 6.4 mM KH$_2$PO$_4$; at least about 6.6 mM KH$_2$PO$_4$; at least about 6.8 mM KH$_2$PO$_4$; at least about 7.0 mM KH$_2$PO$_4$; at least about 7.2 mM KH$_2$PO$_4$; at least about 7.4 mM KH$_2$PO$_4$; at least about 7.6 mM KH$_2$PO$_4$; at least about 7.8 mM KH$_2$PO$_4$; at least about 8.0 mM KH$_2$PO$_4$; at least about 8.2 mM KH$_2$PO$_4$; at least about 8.4 mM KH$_2$PO$_4$; at least about 8.6 mM KH$_2$PO$_4$; at least about 8.8 mM KH$_2$PO$_4$; at least about 9.0 mM KH$_2$PO$_4$; at least about 9.2 mM KH$_2$PO$_4$; at least about 9.4 mM KH$_2$PO$_4$; at least about 9.6 mM KH$_2$PO$_4$; at least about 9.8 mM KH$_2$PO$_4$; at least about 10.0 mM KH$_2$PO$_4$; at least about 20 mM KH$_2$PO$_4$; at least about 30 mM KH$_2$PO$_4$; at least about 40 mM KH$_2$PO$_4$; at least about 50 mM KH$_2$PO$_4$; at least about 60 mM KH$_2$PO$_4$; at least about 70 mM KH$_2$PO$_4$; at least about 80 mM KH$_2$PO$_4$; at least about 90 mM KH$_2$PO$_4$; at least about 100 mM KH$_2$PO$_4$; at least about 110 mM KH$_2$PO$_4$; at least about 120 mM KH$_2$PO$_4$; at least about 130 mM KH$_2$PO$_4$; at least about 140 mM KH$_2$PO$_4$; at least about 150 mM KH$_2$PO$_4$; at least about 160 mM KH$_2$PO$_4$; at least about 170 mM KH$_2$PO$_4$; at least about 180 mM KH$_2$PO$_4$; at least about 190 mM KH$_2$PO$_4$; or at least about 200 mM KH$_2$PO$_4$. It is understood that recitation of the above discrete values includes a range between each recited value.

As another example, a modified simulated body fluid can include about 0.2 mM KH$_2$PO$_4$; about 0.4 mM KH$_2$PO$_4$; about 0.6 mM KH$_2$PO$_4$; about 0.8 mM KH$_2$PO$_4$; about 1.0 mM KH$_2$PO$_4$; about 1.2 mM KH$_2$PO$_4$; about 1.4 mM KH$_2$PO$_4$; about 1.6 mM KH$_2$PO$_4$; about 1.8 mM KH$_2$PO$_4$; about 2.0 mM KH$_2$PO$_4$; about 2.2 mM KH$_2$PO$_4$; about 2.4 mM KH$_2$PO$_4$; about 2.6 mM KH$_2$PO$_4$; about 2.8 mM KH$_2$PO$_4$; about 3.0 mM KH$_2$PO$_4$; about 3.2 mM KH$_2$PO$_4$; about 3.4 mM KH$_2$PO$_4$; about 3.6 mM KH$_2$PO$_4$; about 3.8 mM KH$_2$PO$_4$; about 4.0 mM KH$_2$PO$_4$; about 4.2 mM KH$_2$PO$_4$; about 4.4 mM KH$_2$PO$_4$; about 4.6 mM KH$_2$PO$_4$; about 4.8 mM KH$_2$PO$_4$; about 5.0 mM KH$_2$PO$_4$; about 5.2 mM KH$_2$PO$_4$; about 5.4 mM KH$_2$PO$_4$; about 5.6 mM KH$_2$PO$_4$; about 5.8 mM KH$_2$PO$_4$; about 6.0 mM KH$_2$PO$_4$; about 6.2 mM KH$_2$PO$_4$; about 6.4 mM KH$_2$PO$_4$; about 6.8 mM KH$_2$PO$_4$; about 7.0 mM KH$_2$PO$_4$; about 7.2 mM KH$_2$PO$_4$; about 7.4 mM KH$_2$PO$_4$; about 7.6 mM KH$_2$PO$_4$; about 7.8 mM KH$_2$PO$_4$; about 8.0 mM KH$_2$PO$_4$; about 8.2 mM KH$_2$PO$_4$; about 8.4 mM KH$_2$PO$_4$; about 8.6 mM KH$_2$PO$_4$; about 8.8 mM KH$_2$PO$_4$; about 9.0 mM KH$_2$PO$_4$; about 9.2 mM KH$_2$PO$_4$; about 9.4 mM KH$_2$PO$_4$; about 9.6 mM KH$_2$PO$_4$; about 9.8 mM KH$_2$PO$_4$; about 10.0 mM KH$_2$PO$_4$; about 20 mM KH$_2$PO$_4$; about 30 mM KH$_2$PO$_4$; about 40 mM KH$_2$PO$_4$; about 50 mM KH$_2$PO$_4$; about 60 mM KH$_2$PO$_4$; about 70 mM KH$_2$PO$_4$; about 80 mM KH$_2$PO$_4$; about 90 mM KH$_2$PO$_4$; about 100 mM KH$_2$PO$_4$; about 110 mM KH$_2$PO$_4$; about 120 mM KH$_2$PO$_4$; about 130 mM KH$_2$PO$_4$; about 140 mM KH$_2$PO$_4$; about 150 mM KH$_2$PO$_4$; about 160 mM KH$_2$PO$_4$; about 170 mM KH$_2$PO$_4$; about 180 mM KH$_2$PO$_4$; about 190 mM KH$_2$PO$_4$; or about 200 mM KH$_2$PO$_4$. It is understood that recitation of the above discrete values includes a range between each recited value.

In some embodiments, the solution can comprise a surfactant, which can change the morphology of the calcium-containing mineral layer. Any surfactant now known or later discovered may be used here. In some embodiments, the surfactant can be Tween 20™.

Mineral Coating

A scaffold, or portion or component thereof, described herein can include a surface modification or a coating. The mineral coating of a scaffold, as described herein, can be performed by any conventional manner. A mineral coating can be as described in U.S. application Ser. Nos. 13/407,441; 13/879,178; and 13/036,470 and are incorporated by reference.

The Examples describe exemplary methods for producing coated scaffolds using a mineral coating solution. For example, the mineral coating solution can be a modified simulated body fluid (mSBF). By adjusting the mineral composition, and/or concentration of the mSBF, the composition of the mineral precipitated on the scaffolds can be manipulated. See also U.S. Patent Application Publication US 2008/0095817 A1; U.S. Pat. No. 6,767,928 B1, U.S. Pat. No. 6,541,022 B1, PCT Publication WO 2008/070355 A2; PCT Publication WO 2008/082766 A2; Murphy and Mooney, 2001; Murphy and Messersmith, 2000.

As described herein, the mineral coating can be calcium-containing. For example the calcium-containing mineral coating can include hydroxyapatite (HAP), α-tricalcium phosphate (α-TCP), β-tricalcium phosphate (β-TCP), amorphous calcium phosphate, dicalcium phosphate, octacalcium phosphate, calcium phosphate (CaP), or calcium carbonate. The calcium-containing mineral coating can comprise a plurality of layers, e.g., separate layers having distinct dissolution profiles. Under physiological conditions, solubility of calcium phosphate species can adhere to the following trend: amorphous calcium phosphate>dicalcium phosphate>octacalcium phosphate>β-TCP>HAP. A dicalcium phosphate mineral can have a dissolution rate that is more than fifty times higher than that of HAP. Therefore, creation of a matrix with distinct calcium phosphate layers allows for a broad range of dissolution patterns.

For example, a mineral coating can be according to ISO 2337 'Implants for surgery-In vitro evaluation for apatite-forming ability of implant materials'. As another example, mineral coating can be an adapted protocol according to ISO 2337 'Implants for surgery-In vitro evaluation for apatite-forming ability of implant materials'. As another example, the mineral coating can be performed by immersing a scaffold into a modified simulated body fluid at physiological conditions and continuous rotations. Continuous rotations can be replenishing the modified simulated body fluid, replacing the modified simulated body fluid, or removing and adding modified simulated body fluid.

As described herein, the scaffold can be incubated in modified simulated body fluid (mSBF) solutions to induce formation of a calcium phosphate-based mineral layer for mineral nucleation and growth. The mSBF solution can contain ionic constituents of blood plasma, with double the concentrations of calcium and phosphate ions, held at physiologic temperature and pH. The growth of calcium phosphate-based minerals, specifically bone-like minerals, on bioresorbable polymer matrices using mSBF incubation has been demonstrated (Lin et al., 2004; Murphy et al., 2002, 2005).

As described herein, a mineral coating of a scaffold, as described herein, can be performed by incubating a scaffold. For example, the mineral coating, described herein, can be developed by incubating the constituents in modified simulated body fluid (mSBF), for five days or more at a pH of about 6.8 to about 7.4 and at a temperature of about 37° C. The SBF or mSBF can be refreshed daily. Using the chemical composition described in the Examples, the procedure produces a calcium-deficient, carbonate-containing apatite material on alginate and on poly-(α-hydroxy esters). See U.S. Pat. No. 6,767,928, incorporated herein by reference. mSBF can include elevated calcium and phosphate. In general, an increase in pH can favor hydroxyapatite growth, while a decrease in pH can favor octacalcium phosphate mineral growth.

As another example, conditions favorable for hydroxyapatite formation can include a pH between about 5.0 and about 8.0 and a calcium concentration multiplied by a phosphate concentration between about 10-5 and about 10-8 M. Likewise, conditions favorable for octacalcium phosphate formation include a pH between about 6.0 and about 8.0 and a calcium concentration multiplied by a phosphate concentration between about 10-5 and about 10-7.5 M. Furthermore, conditions favorable for dicalcium phosphate dehydrate formation can include a pH between about 6.0 and about 8.0 and a calcium concentration multiplied by a phosphate concentration between about 10-4 and about 10-6 M.

As another example, one could vary the pH of mSBF between about 5.0 and about 6.0 to promote hydroxyapatite formation. Similarly, one could vary the pH of mSBF between about 6.0 and about 6.5 to promote octacalcium phosphate and hydroxyapatite formation. Likewise, one could vary the pH of mSBF between about 6.5 and about 8.0 to promote dicalcium phosphate, octacalcium phosphate, and hydroxyapatite formation.

As another example, the scaffold can be incubated for at least about 1 day; at least about 2 days; at least about 3 days; at least about 4 days; at least about 5 days; at least about 6 days; at least about 7 days; at least about 8 days; at least about 9 days; at least about 10 days; at least about 11 days; at least about 12 days; at least about 13 days; at least about 14 days; at least about 15 days; at least about 16 days; at least about 17 days; at least about 18 days; at least about 19 days; at least about 20 days; at least about 21 days; at least about 22 days; at least about 23 days; at least about 24 days; at least about 25 days; at least about 26 days; at least about 27 days; at least about 28 days; at least about 29 days; or at least about 30 days. It is understood that recitation of the above discrete values includes a range between each recited value.

For example, the scaffold can be incubated for about 1 day; about 2 days; about 3 days; about 4 days; about 5 days; about 6 days; about 7 days; about 8 days; about 9 days; about 10 days; about 11 days; about 12 days; about 13 days; about 14 days; about 15 days; about 16 days; about 17 days; about 18 days; about 19 days; about 20 days; about 21 days; about 22 days; about 23 days; about 24 days; about 25 days; about 26 days; about 27 days; about 28 days; about 29 days; or about 30 days. It is understood that recitation of the above discrete values includes a range between each recited value.

A mineral coating of a scaffold, as described herein, can be performed by incubating a scaffold at a temperature. For example, the scaffold can be incubated at a physiologically relevant temperature. As another example, the scaffold can be incubated at a temperature of about 1° C.; about 2° C.; about 3° C.; about 4° C.; about 5° C.; about 6° C.; about 7° C.; about 8° C.; about 9° C.; about 10° C.; about 11° C.; about 12° C.; about 13° C.; about 14° C.; about 15° C.; about 16° C.; about 17° C.; about 18° C., about 19° C., about 20° C., about 21° C.; about 22° C.; about 23° C.; about 24° C.; about 25° C.; about 26° C.; about 27° C.; about 28° C.; about 29° C.; about 30° C.; about 31° C.; about 32° C.; about 33° C.; about 34° C.; about 35° C.; about 36° C.; about 37° C.; about 38° C.; about 39° C.; about 40° C.; about 41° C.; about 42° C.; about 43° C.; about 44° C.; about 45° C.; about 46° C.; about 47° C.; about 48° C.; about 49° C.; about 50° C.; about 51° C.; about 52° C.; about 53° C.; about 54° C.; about 55° C.; about 56° C.; about 57° C.; about 58° C.; about 59° C.; about 60° C.; about 61° C.; about 62° C.; about 63° C.; about 64° C.; about 65° C.; about 66° C.; about 67° C.; about 68° C.; about 69° C.; about 70° C.; about 71° C.; about 72° C.; about 73° C.; about 74° C.; about 75° C.; about 76° C.; about 77° C.; about 78° C.; about 79° C.; about 80° C.; about 81° C.; about 82° C.; about 83° C.; about 84° C.; about 85° C.; about 86° C.; about 87° C.; about 88° C.; about 89° C.; about 90° C.; about 91° C.; about 92° C.; about 93° C.; about 94° C.; about 95° C.; about 96° C.; about 97° C.; about 98° C.; about 99° C.; or about 100° C. It is understood that recitation of the above discrete values includes a range between each recited value.

A scaffold, or portion or component thereof, can be coated individually or in groups using, for example, a CaP coating technology. A scaffold, or portion or component thereof, can be modified individually or in groups using a technique such as aminolysis for RGD attachment, chemical conjugation, layer by layer deposition, or chemical vapor deposition.

Prior to deposition of the first calcium-containing mineral, the scaffold may be surface-functionalized to allow increased mineral deposition by utilizing chemical pretreatment to achieve surface hydrolysis (e.g., using an NaOH solution). Surface degradation by this technique can cause an increase in the amount of polar oxygen functional groups on the surface of the material.

The functionalized surface can then be incubated in a mineral-containing solution (e.g., modified simulated body fluid). The mineral coating process, as described herein, can mimic natural biomineralization processes.

The mineral coating, as described herein, can be similar in structure and composition to human bone mineral. For example, the mineral coating can include spherical clusters with a plate-like structure or a plate-like structure and a carbonate-substituted, calcium deficient hydroxyapatite phase composition. As another example, the coating can be an osteoconductive mineral coating.

As another example, the mineral coating can include an apatite. Apatite can include calcium phosphate, calcium carbonate, calcium fluoride, calcium hydroxide, or citrate.

As another example, a mineral coating can comprises a plurality of discrete mineral islands on the scaffold, or the mineral coating can be formed on the entire surface of the scaffold. As another example, the mineral coating can comprise a substantially homogeneous mineral coating. In other embodiments, the mineral coatings can be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, or a mixture thereof. For example, an osteoconductive mineral coating can be calcium-deficient carbonate-containing hydroxyapatite.

As another example, the mineral coating can include hydroxyapatite. Calcium deficient hydroxyapatite can have a formula of $Ca_{10-x}(PO_4)_{6-x}(HPO_4)_x(OH)_{2-x}$. Stoichiometric hydroxyapatite can have a chemical formula of $Ca_{10}(PO_4)_6(OH)_2$ or can be also written as $Ca_5(PO_4)_3(OH)$. Hydroxyapatite can be predominantly crystalline, but may be present in amorphous forms.

The mineral coating, as described herein, can include at least about 1% hydroxyapatite. For example, the mineral coating can include at least about 1% hydroxyapatite; at least about 2% hydroxyapatite; at least about 3% hydroxyapatite; at least about 4% hydroxyapatite; at least about 5% hydroxyapatite; at least about 6% hydroxyapatite; at least about 7% hydroxyapatite; at least about 8% hydroxyapatite; at least about 9% hydroxyapatite; at least about 10% hydroxyapatite; at least about 11% hydroxyapatite; at least about 12% hydroxyapatite; at least about 13% hydroxyapatite; at least about 14% hydroxyapatite; at least about 15% hydroxyapatite; at least about 16% hydroxyapatite; at least about 17% hydroxyapatite; at least about 18% hydroxyapatite; at least about 19% hydroxyapatite; at least about 20% hydroxyapatite; at least about 21% hydroxyapatite; at least about 22% hydroxyapatite; at least about 23% hydroxyapatite; at least about 24% hydroxyapatite; at least about 25% hydroxyapatite; at least about 26% hydroxyapatite; at least about 27% hydroxyapatite; at least about 28% hydroxyapatite; at least about 29% hydroxyapatite; at least about 30% hydroxyapatite; at least about 31% hydroxyapatite; at least about 32% hydroxyapatite; at least about 33% hydroxyapatite; at least about 34% hydroxyapatite; at least about 35% hydroxyapatite; at least about 36% hydroxyapatite; at least about 37% hydroxyapatite; at least about 38% hydroxyapatite; at least about 39% hydroxyapatite; at least about 40% hydroxyapatite; at least about 41% hydroxyapatite; at least about 42% hydroxyapatite; at least about 43% hydroxyapatite; at least about 44% hydroxyapatite; at least about 45% hydroxyapatite; at least about 46% hydroxyapatite; at least about 47% hydroxyapatite; at least about 48% hydroxyapatite; at least about 49% hydroxyapatite; at least about 50% hydroxyapatite; at least about 51% hydroxyapatite; at least about 52% hydroxyapatite; at least about 53% hydroxyapatite; at least about 54% hydroxyapatite; at least about 55% hydroxyapatite; at least about 56% hydroxyapatite; at least about 57% hydroxyapatite; at least about 58% hydroxyapatite; at least about 59% hydroxyapatite; at least about 60% hydroxyapatite; at least about 61% hydroxyapatite; at least about 62% hydroxyapatite; at least about 63% hydroxyapatite; at least about 64% hydroxyapatite; at least about 65% hydroxyapatite; at least about 66% hydroxyapatite; at least about 67% hydroxyapatite; at least about 68% hydroxyapatite; at least about 69% hydroxyapatite; at least about 70% hydroxyapatite; at least about 71% hydroxyapatite; at least about 72% hydroxyapatite; at least about 73% hydroxyapatite; at least about 74% hydroxyapatite; at least about 75% hydroxyapatite; at least about 76% hydroxyapatite; at least about 77% hydroxyapatite; at least about 78% hydroxyapatite; at least about 79% hydroxyapatite; at least about 80% hydroxyapatite; at least about 81% hydroxyapatite; at least about 82% hydroxyapatite; at least about 83% hydroxyapatite; at least about 84% hydroxyapatite; at least about 85% hydroxyapatite; at least about 86% hydroxyapatite; at least about 87% hydroxyapatite; at least about 88% hydroxyapatite; at least about 89% hydroxyapatite; at least about 90% hydroxyapatite; at least about 91% hydroxyapatite; at least about 92% hydroxyapatite; at least about 93% hydroxyapatite; at least about 94% hydroxyapatite; at least about 95% hydroxyapatite; at least about 96% hydroxyapatite; at least about 97% hydroxyapatite; at least about 98% hydroxyapatite; at least about 99% hydroxyapatite; or at least about 100% hydroxyapatite. It is understood that recitation of the above discrete values includes a range between each recited value.

As another example, the mineral coating can include about 1% hydroxyapatite; about 2% hydroxyapatite; about 3% hydroxyapatite; about 4% hydroxyapatite; about 5% hydroxyapatite; about 6% hydroxyapatite; about 7% hydroxyapatite; about 8% hydroxyapatite; about 9% hydroxyapatite; about 10% hydroxyapatite; about 11% hydroxyapatite; about 12% hydroxyapatite; about 13% hydroxyapatite; about 14% hydroxyapatite; about 15% hydroxyapatite; about 16% hydroxyapatite; about 17% hydroxyapatite; about 18% hydroxyapatite; about 19% hydroxyapatite; about 20% hydroxyapatite; about 21% hydroxyapatite; about 22% hydroxyapatite; about 23% hydroxyapatite; about 24% hydroxyapatite; about 25% hydroxyapatite; about 26% hydroxyapatite; about 27% hydroxyapatite; about 28% hydroxyapatite; about 29% hydroxyapatite; about 30% hydroxyapatite; about 31% hydroxyapatite; about 32% hydroxyapatite; about 33% hydroxyapatite; about 34% hydroxyapatite; about 35% hydroxyapatite; about 36% hydroxyapatite; about 37% hydroxyapatite; about 38% hydroxyapatite; about 39% hydroxyapatite; about 40% hydroxyapatite; about 41% hydroxyapatite; about 42% hydroxyapatite; about 43% hydroxyapatite; about 44% hydroxyapatite; about 45% hydroxyapatite; about 46% hydroxyapatite; about 47% hydroxyapatite; about 48% hydroxyapatite; about 49% hydroxyapatite; about 50% hydroxyapatite; about 51% hydroxyapatite; about 52% hydroxyapatite; about 53% hydroxyapatite; about 54% hydroxyapatite; about 55% hydroxyapatite; about 56% hydroxyapatite; about 57% hydroxyapatite; about 58% hydroxyapatite; about 59% hydroxyapatite; about 60% hydroxyapatite; about 61% hydroxyapatite; about 62% hydroxyapatite; about 63% hydroxyapatite; about 64% hydroxyapatite; about 65% hydroxyapatite; about 66% hydroxyapatite; about 67% hydroxyapatite; about 68% hydroxyapatite; about 69% hydroxyapatite; about 70% hydroxyapatite; about 71% hydroxyapatite; about 72% hydroxyapatite; about 73% hydroxyapatite; about 74% hydroxyapatite; about 75% hydroxyapatite; about 76% hydroxyapatite; about 77% hydroxyapatite; about 78% hydroxyapatite; about 79% hydroxyapatite; about 80% hydroxyapatite; about 81% hydroxyapatite; about 82% hydroxyapatite; about 83% hydroxyapatite; about 84% hydroxyapatite; about 85% hydroxyapatite; about 86% hydroxyapatite; about 87% hydroxyapatite; about 88% hydroxyapatite; about 89% hydroxyapatite; about 90% hydroxyapatite; about 91% hydroxyapatite; about 92% hydroxyapatite; about 93% hydroxyapatite; about 94% hydroxyapatite; about 95% hydroxyapatite; about 96% hydroxyapatite; about 97% hydroxyapatite; about 98% hydroxyapatite; about 99% hydroxyapatite; or about 100% hydroxyapatite. It is understood that recitation of the above discrete values includes a range between each recited value.

The mineral coating, as described herein, can include octacalcium phosphate. Octacalcium phosphate has a chemical formula of $Ca_8H_2(PO_4)_6 \cdot 5H_2O$ or can also be written as $Ca_4HO_{12}P_3$. Octacalcium phosphate has been shown to be a precursor of hydroxyapatite. Hydrolysis of Octacalcium phosphate can create hydroxyapatite. Octacalcium phosphate can be predominantly crystalline, but may be present in amorphous forms.

The mineral coating, as described herein, can include at least about 1% octacalcium phosphate. For example, the mineral coating can include at least about 1% octacalcium phosphate; at least about 2% octacalcium phosphate; at least about 3% octacalcium phosphate; at least about 4% octacalcium phosphate; at least about 5% octacalcium phosphate; at least about 6% octacalcium phosphate; at least about 7% octacalcium phosphate; at least about 8% octacalcium phosphate; at least about 9% octacalcium phosphate; at least about 10% octacalcium phosphate; at least about 11% octacalcium phosphate; at least about 12% octacalcium phosphate; at least about 13% octacalcium phosphate; at least about 14% octacalcium phosphate; at least about 15% octacalcium phosphate; at least about 16% octacalcium phosphate; at least about 17% octacalcium phosphate; at least about 18% octacalcium phosphate; at least about 19% octacalcium phosphate; at least about 20% octacalcium phosphate; at least about 21% octacalcium phosphate; at least about 22% octacalcium phosphate; at least about 23% octacalcium phosphate; at least about 24% octacalcium phosphate; at least about 25% octacalcium phosphate; at least about 26% octacalcium phosphate; at least about 27% octacalcium phosphate; at least about 28% octacalcium phosphate; at least about 29% octacalcium phosphate; at least about 30% octacalcium phosphate; at least about 31% octacalcium phosphate; at least about 32% octacalcium phosphate; at least about 33% octacalcium phosphate; at least about 34% octacalcium phosphate; at least about 35% octacalcium phosphate; at least about 36% octacalcium phosphate; at least about 37% octacalcium phosphate; at least about 38% octacalcium phosphate; at least about 39% octacalcium phosphate; at least about 40% octacalcium phosphate; at least about 41% octacalcium phosphate; at least about 42% octacalcium phosphate; at least about 43% octacalcium phosphate; at least about 44% octacalcium phosphate; at least about 45% octacalcium phosphate; at least about 46% octacalcium phosphate; at least about 47% octacalcium phosphate; at least about 48% octacalcium phosphate; at least about 49% octacalcium phosphate; at least about 50% octacalcium phosphate; at least about 51% octacalcium phosphate; at least about 52% octacalcium phosphate; at least about 53% octacalcium phosphate; at least about 54% octacalcium phosphate; at least about 55% octacalcium phosphate; at least about 56% octacalcium phosphate; at least about 57% octacalcium phosphate; at least about 58% octacalcium phosphate; at least about 59% octacalcium phosphate; at least about 60% octacalcium phosphate; at least about 61% octacalcium phosphate; at least about 62% octacalcium phosphate; at least about 63% octacalcium phosphate; at least about 64% octacalcium phosphate; at least about 65% octacalcium phosphate; at least about 66% octacalcium phosphate; at least about 67% octacalcium phosphate; at least about 68% octacalcium phosphate; at least about 69% octacalcium phosphate; at least about 70% octacalcium phosphate; at least about 71% octacalcium phosphate; at least about 72% octacalcium phosphate; at least about 73% octacalcium phosphate; at least about 74% octacalcium phosphate; at least about 75% octacalcium phosphate; at least about 76% octacalcium phosphate; at least about 77% octacalcium phosphate; at least about 78% octacalcium phosphate; at least about 79% octacalcium phosphate; at least about 80% octacalcium phosphate; at least about 81% octacalcium phosphate; at least about 82% octacalcium phosphate; at least about 83% octacalcium phosphate; at least about 84% octacalcium phosphate; at least about 85% octacalcium phosphate; at least about 86% octacalcium phosphate; at least about 87% octacalcium phosphate; at least about 88% octacalcium phosphate; at least about 89% octacalcium phosphate; at least about 90% octacalcium phosphate; at least about 91% octacalcium phosphate; at least about 92% octacalcium phosphate; at least about 93% octacalcium phosphate; at least about 94% octacalcium phosphate; at least about 95% octacalcium phosphate; at least about 96% octacalcium phosphate; at least about 97% octacalcium phosphate; at least about 98% octacalcium phosphate; at least about 99% octacalcium phosphate; or at least about 100% octacalcium phosphate. It is understood that recitation of the above discrete values includes a range between each recited value.

As another example, the mineral coating can include about 1% octacalcium phosphate; about 2% octacalcium phosphate; about 3% octacalcium phosphate; about 4% octacalcium phosphate; about 5% octacalcium phosphate; about 6% octacalcium phosphate; about 7% octacalcium phosphate; about 8% octacalcium phosphate; about 9% octacalcium phosphate; about 10% octacalcium phosphate; about 11% octacalcium phosphate; about 12% octacalcium phosphate; about 13% octacalcium phosphate; about 14% octacalcium phosphate; about 15% octacalcium phosphate; about 16% octacalcium phosphate; about 17% octacalcium phosphate; about 18% octacalcium phosphate; about 19% octacalcium phosphate; about 20% octacalcium phosphate; about 21% octacalcium phosphate; about 22% octacalcium phosphate; about 23% octacalcium phosphate; about 24% octacalcium phosphate; about 25% octacalcium phosphate; about 26% octacalcium phosphate; about 27% octacalcium phosphate; about 28% octacalcium phosphate; about 29% octacalcium phosphate; about 30% octacalcium phosphate; about 31% octacalcium phosphate; about 32% octacalcium phosphate; about 33% octacalcium phosphate; about 34% octacalcium phosphate; about 35% octacalcium phosphate; about 36% octacalcium phosphate; about 37% octacalcium phosphate; about 38% octacalcium phosphate; about 39% octacalcium phosphate; about 40% octacalcium phosphate; about 41% octacalcium phosphate; about 42% octacalcium phosphate; about 43% octacalcium phosphate; about 44% octacalcium phosphate; about 45% octacalcium phosphate; about 46% octacalcium phosphate; about 47% octacalcium phosphate; about 48% octacalcium phosphate; about 49% octacalcium phosphate; about 50% octacalcium phosphate; about 51% octacalcium phosphate; about 52% octacalcium phosphate; about 53% octacalcium phosphate; about 54% octacalcium phosphate; about 55% octacalcium phosphate; about 56% octacalcium phosphate; about 57% octacalcium phosphate; about 58% octacalcium phosphate; about 59% octacalcium phosphate; about 60% octacalcium phosphate; about 61% octacalcium phosphate; about 62% octacalcium phosphate; about 63% octacalcium phosphate; about 64% octacalcium phosphate; about 65% octacalcium phosphate; about 66% octacalcium phosphate; about 67% octacalcium phosphate; about 68% octacalcium phosphate; about 69% octacalcium phosphate; about 70% octacalcium phosphate; about 71% octacalcium phosphate; about 72% octacalcium phosphate; about 73% octacalcium phosphate; about 74% octacalcium phosphate; about 75% octacalcium phosphate; about 76% octacalcium phosphate; about 77% octacalcium phosphate; about 78% octacalcium phosphate; about 79% octacalcium phosphate; about 80% octacalcium phosphate; about 81% octacalcium phosphate; about 82% octacalcium phosphate; about 83% octacalcium phosphate; about 84% octacalcium phosphate; about 85% octacalcium phosphate; about 86% octacalcium phosphate; about 87% octacalcium phosphate; about 88% octacalcium phosphate; about 89% octacalcium phosphate; about 90% octacalcium phosphate; about 91% octacalcium phosphate; about 92% octacalcium phosphate; about 93% octacalcium phosphate; about 94% octacalcium phosphate; about 95% octacalcium phosphate; about 96% octacalcium phosphate; about 97% octacalcium phosphate; about 98% octacalcium phosphate; about 99% octacalcium phosphate; or about 100% octacalcium phosphate. It is understood that recitation of the above discrete values includes a range between each recited value.

The mineral coating, as described herein, can include at least about 1% porosity. For example, the mineral coating, as described herein, can include a porosity of at least about 1% porosity; at least about 2% porosity; at least about 3% porosity; at least about 4% porosity; at least about 5% porosity; at least about 6% porosity; at least about 7% porosity; at least about 8% porosity; at least about 9% porosity; at least about 10% porosity; at least about 11% porosity; at least about 12% porosity; at least about 13% porosity; at least about 14% porosity; at least about 15% porosity; at least about 16% porosity; at least about 17% porosity; at least about 18% porosity; at least about 19% porosity; at least about 20% porosity; at least about 21% porosity; at least about 22% porosity; at least about 23% porosity; at least about 24% porosity; at least about 25% porosity; at least about 26% porosity; at least about 27% porosity; at least about 28% porosity; at least about 29% porosity; at least about 30% porosity; at least about 31% porosity; at least about 32% porosity; at least about 33% porosity; at least about 34% porosity; at least about 35% porosity; at least about 36% porosity; at least about 37% porosity; at least about 38% porosity; at least about 39% porosity; at least about 40% porosity; at least about 41% porosity; at least about 42% porosity; at least about 43% porosity; at least about 44% porosity; at least about 45% porosity; at least about 46% porosity; at least about 47% porosity; at least about 48% porosity; at least about 49% porosity; at least about 50% porosity; at least about 51% porosity; at least about 52% porosity; at least about 53% porosity; at least about 54% porosity; at least about 55% porosity; at least about 56% porosity; at least about 57% porosity; at least about 58% porosity; at least about 59% porosity; at least about 60% porosity; at least about 61% porosity; at least about 62% porosity; at least about 63% porosity; at least about 64% porosity; at least about 65% porosity; at least about 66% porosity; at least about 67% porosity; at least about 68% porosity; at least about 69% porosity; at least about 70% porosity; at least about 71% porosity; at least about 72% porosity; at least about 73% porosity; at least about 74% porosity; at least about 75% porosity; at least about 76% porosity; at least about 77% porosity; at least about 78% porosity; at least about 79% porosity; at least about 80% porosity; at least about 81% porosity; at least about 82% porosity; at least about 83% porosity; at least about 84% porosity; at least about 85% porosity; at least about 86% porosity; at least about 87% porosity; at least about 88% porosity; at least about 89% porosity; at least about 90% porosity; at least about 91% porosity; at least about 92% porosity; at least about 93% porosity; at least about 94% porosity; at least about 95% porosity; at least about 96% porosity; at least about 97% porosity; at least about 98% porosity; at least about 99% porosity; or at least about 100% porosity. It is understood that recitation of the above discrete values includes a range between each recited value.

As another example, the mineral coating can include about 1% porosity; about 2% porosity; about 3% porosity; about 4% porosity; about 5% porosity; about 6% porosity; about 7% porosity; about 8% porosity; about 9% porosity; about 10% porosity; about 11% porosity; about 12% porosity; about 13% porosity; about 14% porosity; about 15% porosity; about 16% porosity; about 17% porosity; about 18% porosity; about 19% porosity; about 20% porosity; about 21% porosity; about 22% porosity; about 23% porosity; about 24% porosity; about 25% porosity; about 26% porosity; about 27% porosity; about 28% porosity; about 29% porosity; about 30% porosity; about 31% porosity; about 32% porosity; about 33% porosity; about 34% porosity; about 35% porosity; about 36% porosity; about 37% porosity; about 38% porosity; about 39% porosity; about 40% porosity; about 41% porosity; about 42% porosity; about 43% porosity; about 44% porosity; about 45% porosity; about 46% porosity; about 47% porosity; about 48% porosity; about 49% porosity; about 50% porosity; about 51% porosity; about 52% porosity; about 53% porosity; about 54% porosity; about 55% porosity; about 56% porosity; about 57% porosity; about 58% porosity; about 59% porosity; about 60% porosity; about 61% porosity; about 62% porosity; about 63% porosity; about 64% porosity; about 65% porosity; about 66% porosity; about 67% porosity; about 68% porosity; about 69% porosity; about 70% porosity; about 71% porosity; about 72% porosity; about 73% porosity; about 74% porosity; about 75% porosity; about 76% porosity; about 77% porosity; about 78% porosity; about 79% porosity; about 80% porosity; about 81% porosity; about 82% porosity; about 83% porosity; about 84% porosity; about 85% porosity; about 86% porosity; about 87% porosity; about 88% porosity; about 89% porosity; about 90% porosity; about 91% porosity; about 92% porosity; about 93% porosity; about 94% porosity; about 95% porosity; about 96% porosity; about 97% porosity; about 98% porosity; about 99% porosity; or about 100% porosity. It is understood that recitation of the above discrete values includes a range between each recited value.

The mineral coating, as described herein, can include a pore diameter between about 1 nm and about 3500 nm. As another example, the mineral coating, as described herein, can include a pore diameter between about 100 and about 350 nm. As another example, the mineral coating, as described herein, can include at least about 1 nm pore diameter; at least about 10 nm pore diameter; at least about 15 nm pore diameter; at least about 20 nm pore diameter; at least about 25 nm pore diameter; at least about 30 nm pore diameter; at least about 35 nm pore diameter; at least about 40 nm pore diameter; at least about 45 nm pore diameter; at least about 50 nm pore diameter; at least about 55 nm pore diameter; at least about 60 nm pore diameter; at least about 65 nm pore diameter; at least about 70 nm pore diameter; at least about 75 nm pore diameter; at least about 80 nm pore diameter; at least about 85 nm pore diameter; at least about 90 nm pore diameter; at least about 95 nm pore diameter; at least about 100 nm pore diameter; at least about 105 nm pore diameter; at least about 110 nm pore diameter; at least about 115 nm pore diameter; at least about 120 nm pore diameter; at least about 125 nm pore diameter; at least about 130 nm pore diameter; at least about 135 nm pore diameter; at least about 140 nm pore diameter; at least about 145 nm pore diameter; at least about 150 nm pore diameter; at least about 155 nm pore diameter; at least about 160 nm pore diameter; at least about 165 nm pore diameter; at least about 170 nm pore diameter; at least about 175 nm pore diameter; at least about 180 nm pore diameter; at least about 185 nm pore diameter; at least about 190 nm pore diameter; at least about 195 nm pore diameter; at least about 200 nm pore diameter; at least about 205 nm pore diameter; at least about 210 nm pore diameter; at least about 215 nm pore diameter; at least about 220 nm pore diameter; at least about 225 nm pore diameter; at least about 230 nm pore diameter; at least about 235 nm pore diameter; at least about 240 nm pore diameter; at least about 245 nm pore diameter; at least about 250 nm pore diameter; at least about 255 nm pore diameter; at least about 260 nm pore diameter; at least about 265 nm pore diameter; at least about 270 nm pore diameter; at least about 275 nm pore diameter; at least about 280 nm pore diameter; at least about 285 nm pore diameter; at least about 290 nm pore diameter; at least about 295 nm pore diameter; at least about 300 nm pore diameter; at least about 305 nm pore diameter; at least about 310 nm pore diameter; at least about 315 nm pore diameter; at least about 320 nm pore diameter; at least about 325 nm pore diameter; at least about 330 nm pore diameter; at least about 335 nm pore diameter; at least about 340 nm pore diameter; at least about 345 nm pore diameter; at least about 350 nm pore diameter; at least about 355 nm pore diameter; at least about 360 nm pore diameter; at least about 365 nm pore diameter; at least about 370 nm pore diameter; at least about 375 nm pore diameter; at least about 400 nm pore diameter; at least about 410 nm pore diameter; at least about 420 nm pore diameter; at least about 430 nm pore diameter; at least about 440 nm pore diameter; at least about 450 nm pore diameter; at least about 460 nm pore diameter; at least about 470 nm pore diameter; at least about 480 nm pore diameter; at least about 490 nm pore diameter; at least about 500 nm pore diameter; at least about 600 nm pore diameter; at least about 700 nm pore diameter; at least about 800 nm pore diameter; at least about 900 nm pore diameter; at least about 1000 nm pore diameter; at least about 1100 nm pore diameter; at least about 1200 nm pore diameter; at least about 1300 nm pore diameter; at least about 1400 nm pore diameter; at least about 1500 nm pore diameter; at least about 1600 nm pore diameter; at least about 1700 nm pore diameter; at least about 1800 nm pore diameter; at least about 1900 nm pore diameter; at least about 2000 nm pore diameter; at least about 2100 nm pore diameter; at least about 2200 nm pore diameter; at least about 2300 nm pore diameter; at least about 2400 nm pore diameter; at least about 2500 nm pore diameter; at least about 2600 nm pore diameter; at least about 2700 nm pore diameter; at least about 2800 nm pore diameter; at least about 2900 nm pore diameter; at least about 3000 nm pore diameter; at least about 3100 nm pore diameter; at least about 3200 nm pore diameter; at least about 3300 nm pore diameter; at least about 3400 nm pore diameter; or at least about 3500 nm pore diameter. It is understood that recitation of the above discrete values includes a range between each recited value.

As another example, the mineral coating, as described herein, can include about 1 nm pore diameter; about 10 nm pore diameter; about 20 nm pore diameter; about 30 nm pore diameter; about 40 nm pore diameter; about 50 nm pore diameter; about 55 nm pore diameter; about 60 nm pore diameter; about 65 nm pore diameter; about 70 nm pore diameter; about 75 nm pore diameter; about 80 nm pore diameter; about 85 nm pore diameter; about 90 nm pore diameter; about 95 nm pore diameter; about 100 nm pore diameter; about 105 nm pore diameter; about 110 nm pore diameter; about 115 nm pore diameter; about 120 nm pore diameter; about 125 nm pore diameter; about 130 nm pore diameter; about 135 nm pore diameter; about 140 nm pore diameter; about 145 nm pore diameter; about 150 nm pore diameter; about 155 nm pore diameter; about 160 nm pore diameter; about 165 nm pore diameter; about 170 nm pore diameter; about 175 nm pore diameter; about 180 nm pore diameter; about 185 nm pore diameter; about 190 nm pore diameter; about 195 nm pore diameter; about 200 nm pore diameter; about 205 nm pore diameter; about 210 nm pore diameter; about 215 nm pore diameter; about 220 nm pore diameter; about 225 nm pore diameter; about 230 nm pore diameter; about 235 nm pore diameter; about 240 nm pore diameter; about 245 nm pore diameter; about 250 nm pore diameter; about 255 nm pore diameter; about 260 nm pore diameter; about 265 nm pore diameter; about 270 nm pore diameter; about 275 nm pore diameter; about 280 nm pore diameter; about 285 nm pore diameter; about 290 nm pore diameter; about 295 nm pore diameter; about 300 nm pore diameter; about 305 nm pore diameter; about 310 nm pore diameter; about 315 nm pore diameter; about 320 nm pore diameter; about 320 nm pore diameter; about 330 nm pore diameter; about 335 nm pore diameter; about 340 nm pore diameter; about 345 nm pore diameter; about 350 nm pore diameter; about 355 nm pore diameter; about 360 nm pore diameter; about 365 nm pore diameter; about 370 nm pore diameter; about 375 nm pore diameter; about 380 nm pore diameter; about 390 nm pore diameter; about 400 nm pore diameter; about 410 nm pore diameter; about 420 nm pore diameter; about 430 nm pore diameter; about 440 nm pore diameter; about 450 nm pore diameter; about 460 nm pore diameter; about 470 nm pore diameter; about 480 nm pore diameter; about 490 nm pore diameter; about 500 nm pore diameter; about 600 nm pore diameter; about 700 nm pore diameter; about 800 nm pore diameter; about 900 nm pore diameter; about 1000 nm pore diameter; about 1100 nm pore diameter; about 1200 nm pore diameter; about 1300 nm pore diameter; about 1400 nm pore diameter; about 1500 nm pore diameter; about 1600 nm pore diameter; about 1700 nm pore diameter; about 1800 nm pore diameter; about 1900 nm pore diameter; about 2000 nm pore diameter; about 2100 nm pore diameter; about 2200 nm pore diameter; about 2300 nm pore diameter; about 2400 nm pore diameter; about 2500 nm pore diameter; about 2600 nm pore diameter; about 2700 nm pore diameter; about 2800 nm pore diameter; about 2900 nm pore diameter; about 3000 nm pore diameter; about 3100 nm pore diameter; about 3200 nm pore diameter; about 3300 nm pore diameter; about 3400 nm pore diameter; or about 3500 nm pore diameter. It is understood that recitation of the above discrete values includes a range between each recited value.

The mineral coating, as described herein, can include a ratio of at least about 0.1 Ca/P. For example, the mineral coating can include a ratio of at least about 0.1 Ca/P; at least about 0.2 Ca/P; at least about 0.3 Ca/P; at least about 0.4 Ca/P; at least about 0.5 Ca/P; at least about 0.6 Ca/P; at least about 0.7 Ca/P; at least about 0.8 Ca/P; at least about 0.9 Ca/P; at least about 1.0 Ca/P; at least about 1.1 Ca/P; at least about 1.2 Ca/P; at least about 1.3 Ca/P; at least about 1.4 Ca/P; at least about 1.5 Ca/P; at least about 1.6 Ca/P; at least about 1.7 Ca/P; at least about 1.8 Ca/P; at least about 1.9 Ca/P; at least about 2.0 Ca/P; at least about 2.1 Ca/P; at least about 2.2 Ca/P; at least about 2.3 Ca/P; at least about 2.4 Ca/P; at least about 2.5 Ca/P; at least about 2.6 Ca/P; at least about 2.7 Ca/P; at least about 2.8 Ca/P; at least about 2.9 Ca/P; at least about 3.0 Ca/P; at least about 3.1 Ca/P; at least about 3.2 Ca/P; at least about 3.3 Ca/P; at least about 3.4 Ca/P; at least about 3.5 Ca/P; at least about 3.6 Ca/P; at least about 3.7 Ca/P; at least about 3.8 Ca/P; at least about 3.9 Ca/P; at least about 4 Ca/P; at least about 5 Ca/P; at least about 6 Ca/P; at least about 7 Ca/P; at least about 8 Ca/P; at least about 9 Ca/P; at least about 10 Ca/P; at least about 11 Ca/P; at least about 12 Ca/P; at least about 13 Ca/P; at least about 14 Ca/P; at least about 15 Ca/P; at least about 16 Ca/P; at least about 17 Ca/P; at least about 18 Ca/P; at least about 19 Ca/P; or at least about 20 Ca/P. It is understood that recitation of the above discrete values includes a range between each recited value.

As another example, the mineral coating can include a ratio of about 0.1 Ca/P, about 0.2 Ca/P, about 0.3 Ca/P, about 0.4 Ca/P, about 0.5 Ca/P, about 0.6 Ca/P, about 0.7 Ca/P, about 0.8 Ca/P, about 0.9 Ca/P, about 1.0 Ca/P, about 1.1 Ca/P, about 1.2 Ca/P, about 1.3 Ca/P, about 1.4 Ca/P, about 1.5 Ca/P, about 1.6 Ca/P, about 1.7 Ca/P, about 1.8 Ca/P, about 1.9 Ca/P, about 2.0 Ca/P, about 2.1 Ca/P, about 2.2 Ca/P, about 2.3 Ca/P, about 2.4 Ca/P, about 2.5 Ca/P, about 2.6 Ca/P, about 2.7 Ca/P, about 2.8 Ca/P, about 2.9 Ca/P, about 3.0 Ca/P, about 3.1 Ca/P, about 3.2 Ca/P, about 3.3 Ca/P, about 3.4 Ca/P, about 3.5 Ca/P, about 3.6 Ca/P, about 3.7 Ca/P, about 3.8 Ca/P, about 3.9 Ca/P, about 4 Ca/P, about 5 Ca/P, about 6 Ca/P, about 7 Ca/P, about 8 Ca/P, about 9 Ca/P, about 10 Ca/P, about 11 Ca/P, about 12 Ca/P, about 13 Ca/P, about 14 Ca/P, about 15 Ca/P, about 16 Ca/P, about 17 Ca/P, about 18 Ca/P, about 19 Ca/P, or about 20 Ca/P. It is understood that recitation of the above discrete values includes a range between each recited value.

A mineral coating, as described herein, can be characterized by conventional methods. For example, mineral formation in mSBF can be tracked by analyzing changes in solution calcium concentration using a calcium sensitive electrode (Denver Instrument, Denver, Colo.). After their growth, the mineral matrices can be dissolved and analyzed for calcium and phosphate ion content to quantify mineral formation, and the mineral crystals can be analyzed morphologically and compositionally using a scanning electron microscope (SEM), e.g., with a Noran SiLi detector for elemental analysis.

For example, the crystalline phase can be characterized by X-ray diffraction, where 2θ is in the range of 15-35° or 25.8°, 28.1°, 28.9°, 31.8°, or 32.1°.

As another example, as described herein, the chemical composition or crystalline phase can be characterized by Fourier transform infrared spectroscopy (FTIR), where carbonate peaks can be in the 1400-1500 $cm^{-1}$ region and phosphate peaks can be in the 900-1100 $cm^{-1}$ region or about 570 $cm^{-1}$, 962 $cm^{-1}$, or 1050 $cm^{-1}$.

As another example, as described herein, dissolution of mineral layers can also be characterized by measuring release of calcium and phosphate ions during incubation in tris-buffered saline at physiologically relevant conditions (e.g., 37° C., pH 7.4).

As another example, as described herein, calcium and phosphate concentrations can be measured using previously described colorimetric assays (see Murphy et al., "Bioinspired growth of crystalline carbonate apatite on biodegradable polymer substrata", *J Am Chem Soc* 124:1910-7, 2002). Each of the characterization methods described herein are routine in analysis of inorganic materials, and is consistent with FDA's good guidance practices for design and testing of calcium phosphate coatings (see Devices FDoGaR. Calcium phosphate coating draft guidance for preparation of FDA submissions for orthopedic and dental endosseous implants. 1997).

As another example, as described herein, the mineral coating, can be predominantly crystalline, but can be present in amorphous forms. For example, the mineral coating can have at least about 5% crystallinity. For example, a mineral coating can include at least about 5% crystallinity; at least about 10% crystallinity; at least about 15% crystallinity; at least about 20% crystallinity; at least about 25% crystallinity; at least about 30% crystallinity; at least about 35% crystallinity; at least about 40% crystallinity; at least about 45% crystallinity; at least about 46% crystallinity; at least about 47% crystallinity; at least about 48% crystallinity; at least about 49% crystallinity; at least about 50% crystallinity; at least about 51% crystallinity; at least about 52% crystallinity; at least about 53% crystallinity; at least about 54% crystallinity; at least about 55% crystallinity; at least about 56% crystallinity; at least about 57% crystallinity; at least about 58% crystallinity; at least about 59% crystallinity; at least about 60% crystallinity; at least about 61% crystallinity; at least about 62% crystallinity; at least about 63% crystallinity; at least about 64% crystallinity; at least about 65% crystallinity; at least about 66% crystallinity; at least about 67% crystallinity; at least about 68% crystallinity; at least about 69% crystallinity; at least about 70% crystallinity; at least about 71% crystallinity; at least about 72% crystallinity; at least about 73% crystallinity; at least about 74% crystallinity; at least about 75% crystallinity; at least about 76% crystallinity; at least about 77% crystallinity; at least about 78% crystallinity; at least about 79% crystallinity; at least about 80% crystallinity; at least about 81% crystallinity; at least about 82% crystallinity; at least about 83% crystallinity; at least about 84% crystallinity; at least about 85% crystallinity; at least about 86% crystallinity; at least about 87% crystallinity; at least about 88% crystallinity; at least about 89% crystallinity; at least about 90% crystallinity; at least about 91% crystallinity; at least about 92% crystallinity; at least about 93% crystallinity; at least about 94% crystallinity; at least about 95% crystallinity; at least about 96% crystallinity; at least about 97% crystallinity; at least about 98% crystallinity; at least about 99% crystallinity; or at least about 100% crystallinity. It is understood that recitation of the above discrete values includes a range between each recited value.

As another example, a mineral coating can include about 5% crystallinity; 10% crystallinity; about 15% crystallinity; about 20% crystallinity; about 25% crystallinity; about 30% crystallinity; about 35% crystallinity; about 40% crystallinity; about 45% crystallinity; about 46% crystallinity; about 47% crystallinity; about 48% crystallinity; about 49% crystallinity; about 50% crystallinity; about 51% crystallinity; about 52% crystallinity; about 53% crystallinity; about 54% crystallinity; about 55% crystallinity; about 56% crystallinity; about 57% crystallinity; about 58% crystallinity; about 59% crystallinity; about 60% crystallinity; about 61% crystallinity; about 62% crystallinity; about 63% crystallinity; about 64% crystallinity; about 65% crystallinity; about 66% crystallinity; about 67% crystallinity; about 68% crystallinity; about 69% crystallinity; about 70% crystallinity; about 71% crystallinity; about 72% crystallinity; about 73% crystallinity; about 74% crystallinity; about 75% crystallinity; about 76% crystallinity; about 77% crystallinity; about 78% crystallinity; about 79% crystallinity; about 80% crystallinity; about 81% crystallinity; about 82% crystallinity; about 83% crystallinity; about 84% crystallinity; about 85% crystallinity; about 86% crystallinity; about 87% crystallinity; about 88% crystallinity; about 89% crystallinity; about 90% crystallinity; about 91% crystallinity; about 92% crystallinity; about 93% crystallinity; about 94% crystallinity; about 95% crystallinity; about 96% crystallinity; about 97% crystallinity; about 98% crystallinity; about 99% crystallinity; or about 100% crystallinity. It is understood that recitation of the above discrete values includes a range between each recited value.

As described herein, osteoconductivity and osteoinductivity can be conferred to scaffolds (e.g., orthopedic implant materials) using calcium phosphate coatings. Based on the well-defined osteoconductivity and potential osteoinductivity of calcium-phosphate-based mineral coatings, calcium phosphate mineral growth can be advantageously utilized to coat scaffolds.

Auxiliary Components

The mineral coating, as described herein, can include auxiliary components. For example, the auxiliary components can be incorporated onto the scaffold, the surface of the coating, or within the coating of the scaffold.

For example, an auxiliary component can provide desirable characteristics to the mineral coating, such as improved osteoconductivity, osteoinductivity, osteopromotion, osteogenesis, strength, antibacterial, antimicrobial properties, biostatic, or anti-infection properties.

As described herein, an auxiliary component can be an organic or collagen matrix, such as demineralized bone matrix (DBM). As described herein, DBM can be of any form known in the art. For example DBM can be a demineralized bone powder, demineralized bone extract, demineralized bone gelatin, granules, fragments, pellets, slices, shavings, putty, paste, mix, or strips.

As described herein, DBM can be incorporated into or onto the coating or scaffold by any method known in the art. As another example, DBM can be loaded or integrated into a porous material, such as a porous scaffold. As another example, DBM can be loaded into a medical device, such as a porous, coated, bioresorbable implant formed via 3-D printing. As another example, DBM can be combined with a mineral-coated device. As another example, DBM can be incorporated with the mineral coating, scaffold, or matrix material by mixing, coating, or loading.

As described herein DBM can be integrated with the scaffold or mineral coated scaffold by any method known in the art. The incorporation of DBM into a mineral coating can be as described in Ozturk et al. 2006 Int Orth 30, 147-152 or US Pat Pub No. 2008/0233203.

As described herein, preparing DBM to be integrated with a scaffold can comprise mixing DBM with an aqueous solution. For example, the aqueous solution can be the mineral coating solution as described herein. As another example, the aqueous solution can be a weak acid or guanidine hydrochloride. The mixture can be constantly agitated for a set amount of time to produce an aqueous demineralized bone extract. The extract can then be filtered to remove any remaining solids, the acid neutralized or removed, and the extract used to coat the porous scaffold.

As described herein, the amount of DBM in a solution can be from about 1 g to about 99 g DBM or from about 2 g to about 10 g DBM per 100 g of aqueous solution. The amount of DBM can comprise at least about 1 g DBM per 100 g aqueous solution. For example, the amount of DBM in a solution can comprise at least about 1 g DBM per 100 g aqueous solution; at least about 2 g DBM per 100 g aqueous solution; at least about 3 g DBM per 100 g aqueous solution; at least about 4 g DBM per 100 g aqueous solution; at least about 5 g DBM per 100 g aqueous solution; at least about 6 g DBM per 100 g aqueous solution; at least about 7 g DBM per 100 g aqueous solution; at least about 8 g DBM per 100 g aqueous solution; at least about 9 g DBM per 100 g aqueous solution; at least about 10 g DBM per 100 g aqueous solution; at least about 11 g DBM per 100 g aqueous solution; at least about 12 g DBM per 100 g aqueous solution; at least about 13 g DBM per 100 g aqueous solution; at least about 14 g DBM per 100 g aqueous solution; at least about 15 g DBM per 100 g aqueous solution; at least about 16 g DBM per 100 g aqueous solution; at least about 17 g DBM per 100 g aqueous solution; at least about 18 g DBM per 100 g aqueous solution; at least about 19 g DBM per 100 g aqueous solution; at least about 20 g DBM per 100 g aqueous solution; at least about 21 g DBM per 100 g aqueous solution; at least about 22 g DBM per 100 g aqueous solution; at least about 23 g DBM per 100 g aqueous solution; at least about 24 g DBM per 100 g aqueous solution; at least about 25 g DBM per 100 g aqueous solution; at least about 26 g DBM per 100 g aqueous solution; at least about 27 g DBM per 100 g aqueous solution; at least about 28 g DBM per 100 g aqueous solution; at least about 29 g DBM per 100 g aqueous solution; at least about 30 g DBM per 100 g aqueous solution; at least about 31 g DBM per 100 g aqueous solution; at least about 32 g DBM per 100 g aqueous solution; at least about 33 g DBM per 100 g aqueous solution; at least about 34 g DBM per 100 g aqueous solution; at least about 35 g DBM per 100 g aqueous solution; at least about 36 g DBM per 100 g aqueous solution; at least about 37 g DBM per 100 g aqueous solution; at least about 38 g DBM per 100 g aqueous solution; at least about 39 g DBM per 100 g aqueous solution; at least about 40 g DBM per 100 g aqueous solution; at least about 41 g DBM per 100 g aqueous solution; at least about 42 g DBM per 100 g aqueous solution; at least about 43 g DBM per 100 g aqueous solution; at least about 44 g DBM per 100 g aqueous solution; at least about 45 g DBM per 100 g aqueous solution; at least about 46 g DBM per 100 g aqueous solution; at least about 47 g DBM per 100 g aqueous solution; at least about 48 g DBM per 100 g aqueous solution; at least about 49 g DBM per 100 g aqueous solution; at least about 50 g DBM per 100 g aqueous solution; at least about 51 g DBM per 100 g aqueous solution; at least about 52 g DBM per 100 g aqueous solution; at least about 53 g DBM per 100 g aqueous solution; at least about 54 g DBM per 100 g aqueous solution; at least about 55 g DBM per 100 g aqueous solution; at least about 56 g DBM per 100 g aqueous solution; at least about 57 g DBM per 100 g aqueous solution; at least about 58 g DBM per 100 g aqueous solution; at least about 59 g DBM per 100 g aqueous solution; at least about 60 g DBM per 100 g aqueous solution; at least about 61 g DBM per 100 g aqueous solution; at least about 62 g DBM per 100 g aqueous solution; at least about 63 g DBM per 100 g aqueous solution; at least about 64 g DBM per 100 g aqueous solution; at least about 65 g DBM per 100 g aqueous solution; at least about 66 g DBM per 100 g aqueous solution; at least about 67 g DBM per 100 g aqueous solution; at least about 68 g DBM per 100 g aqueous solution; at least about 69 g DBM per 100 g aqueous solution; at least about 70 g DBM per 100 g aqueous solution; at least about 71 g DBM per 100 g aqueous solution; at least about 72 g DBM per 100 g aqueous solution; at least about 73 g DBM per 100 g aqueous solution; at least about 74 g DBM per 100 g aqueous solution; at least about 75 g DBM per 100 g aqueous solution; at least about 76 g DBM per 100 g aqueous solution; at least about 77 g DBM per 100 g aqueous solution; at least about 78 g DBM per 100 g aqueous solution; at least about 79 g DBM per 100 g aqueous solution; at least about 80 g DBM per 100 g aqueous solution; at least about 81 g DBM per 100 g aqueous solution; at least about 82 g DBM per 100 g aqueous solution; at least about 83 g DBM per 100 g aqueous solution; at least about 84 g DBM per 100 g aqueous solution; at least about 85 g DBM per 100 g aqueous solution; at least about 86 g DBM per 100 g aqueous solution; at least about 87 g DBM per 100 g aqueous solution; at least about 88 g DBM per 100 g aqueous solution; at least about 89 g DBM per 100 g aqueous solution; at least about 90 g DBM per 100 g aqueous solution; at least about 91 g DBM per 100 g aqueous solution; at least about 92 g DBM per 100 g aqueous solution; at least about 93 g DBM per 100 g aqueous solution; at least about 94 g DBM per 100 g aqueous solution; at least about 95 g DBM per 100 g aqueous solution; at least about 96 g DBM per 100 g aqueous solution; at least about 97 g DBM per 100 g aqueous solution; at least about 98 g DBM per 100 g aqueous solution; or at least about 99 g DBM per 100 g aqueous solution per 100 g of aqueous solution. It is understood that recitation of the above discrete values includes a range between each recited value.

As another example, the amount of DBM can comprise about 1 g DBM per 100 g aqueous solution. The amount of DBM can comprise about 1 g DBM per 100 g aqueous solution; about 2 g DBM per 100 g aqueous solution; about 3 g DBM per 100 g aqueous solution; about 4 g DBM per 100 g aqueous solution; about 5 g DBM per 100 g aqueous solution; about 6 g DBM per 100 g aqueous solution; about 7 g DBM per 100 g aqueous solution; about 8 g DBM per 100 g aqueous solution; about 9 g DBM per 100 g aqueous solution; about 10 g DBM per 100 g aqueous solution; about 11 g DBM per 100 g aqueous solution; about 12 g DBM per 100 g aqueous solution; about 13 g DBM per 100 g aqueous solution; about 14 g DBM per 100 g aqueous solution; about 15 g DBM per 100 g aqueous solution; about 16 g DBM per 100 g aqueous solution; about 17 g DBM per 100 g aqueous solution; about 18 g DBM per 100 g aqueous solution; about 19 g DBM per 100 g aqueous solution; about 20 g DBM per 100 g aqueous solution; about 21 g DBM per 100 g aqueous solution; about 22 g DBM per 100 g aqueous solution; about 23 g DBM per 100 g aqueous solution; about 24 g DBM per 100 g aqueous solution; about 25 g DBM per 100 g aqueous solution; about 26 g DBM per 100 g aqueous solution; about 27 g DBM per 100 g aqueous solution; about 28 g DBM per 100 g aqueous solution; about 29 g DBM per 100 g aqueous solution; about 30 g DBM per 100 g aqueous solution; about 31 g DBM per 100 g aqueous solution; about 32 g DBM per 100 g aqueous solution; about 33 g DBM per 100 g aqueous solution; about 34 g DBM per 100 g aqueous solution; about 35 g DBM per 100 g aqueous solution; about 36 g DBM per 100 g aqueous solution; about 37 g DBM per 100 g aqueous solution; about 38 g DBM per 100 g aqueous solution; about 39 g DBM per 100 g aqueous solution; about 40 g DBM per 100 g aqueous solution; about 41 g DBM per 100 g aqueous solution; about 42 g DBM per 100 g aqueous solution; about 43 g DBM per 100 g aqueous solution; about 44 g DBM per 100 g aqueous solution; about 45 g DBM per 100 g aqueous solution; about 46 g DBM per 100 g aqueous solution; about 47 g DBM per 100 g aqueous solution; about 48 g DBM per 100 g aqueous solution; about 49 g DBM per 100 g aqueous solution; about 50 g DBM per 100 g aqueous solution; about 51 g DBM per 100 g aqueous solution; about 52 g DBM per 100 g aqueous solution; about 53 g DBM per 100 g aqueous solution; about 54 g DBM per 100 g aqueous solution; about 55 g DBM per 100 g aqueous solution; about 56 g DBM per 100 g aqueous solution; about 57 g DBM per 100 g aqueous solution; about 58 g DBM per 100 g aqueous solution; about 59 g DBM per 100 g aqueous solution; about 60 g DBM per 100 g aqueous solution; about 61 g DBM per 100 g aqueous solution; about 62 g DBM per 100 g aqueous solution; about 63 g DBM per 100 g aqueous solution; about 64 g DBM per 100 g aqueous solution; about 65 g DBM per 100 g aqueous solution; about 66 g DBM per 100 g aqueous solution; about 67 g DBM per 100 g aqueous solution; about 68 g DBM per 100 g aqueous solution; about 69 g DBM per 100 g aqueous solution; about 70 g DBM per 100 g aqueous solution; about 71 g DBM per 100 g aqueous solution; about 72 g DBM per 100 g aqueous solution; about 73 g DBM per 100 g aqueous solution; about 74 g DBM per 100 g aqueous solution; about 75 g DBM per 100 g aqueous solution; about 76 g DBM per 100 g aqueous solution; about 77 g DBM per 100 g aqueous solution; about 78 g DBM per 100 g aqueous solution; about 79 g DBM per 100 g aqueous solution; about 80 g DBM per 100 g aqueous solution; about 81 g DBM per 100 g aqueous solution; about 82 g DBM per 100 g aqueous solution; about 83 g DBM per 100 g aqueous solution; about 84 g DBM per 100 g aqueous solution; about 85 g DBM per 100 g aqueous solution; about 86 g DBM per 100 g aqueous solution; about 87 g DBM per 100 g aqueous solution; about 88 g DBM per 100 g aqueous solution; about 89 g DBM per 100 g aqueous solution; about 90 g DBM per 100 g aqueous solution; about 91 g DBM per 100 g aqueous solution; about 92 g DBM per 100 g aqueous solution; about 93 g DBM per 100 g aqueous solution; about 94 g DBM per 100 g aqueous solution; about 95 g DBM per 100 g aqueous solution; about 96 g DBM per 100 g aqueous solution; about 97 g DBM per 100 g aqueous solution; about 98 g DBM per 100 g aqueous solution; or about 99 g DBM per 100 g aqueous solution. It is understood that recitation of the above discrete values includes a range between each recited value.

The aqueous solution can comprise the mineral coating solution as described herein. The aqueous solution can comprise any biologically compatible aqueous solution, particularly those in which mineral coating components, growth factors, or proteins may be stable in. Examples of such solutions can be, but not limited to the mineral coating solution as described above, Tris buffer, Tris buffered saline, phosphate buffer, or phosphate buffered saline. For example, the solution can be a weak acid solution where the weak acid can be, but not limited to, citric acid, lactic acid, malic acid, ascorbic acid or combinations thereof. Any weak acid known in the art can be used. The concentration of the weak acid solution can be from about 2 M to about 3 M. In a second illustrative embodiment, the solution can be a guanidine hydrochloride solution where the concentration of the guanidine hydrochloride solution can be from about 3 M to about 6 M.

The amount of time that the DBM and aqueous solution can be mixed can be from about 8 hours to about 96 hours. For example, the DBM and aqueous solution can be mixed together from about 24 hours to about 96 hours. The DBM and aqueous solution can be mixed together with constant agitation during that time. Constant agitation can be obtained by, but not limited to, stirring, shaking, ultrasound or any combination thereof as well as any other methods of agitating a mixture.

The mixing can be carried out at a temperature that can be conducive to coating a scaffold and extracting growth factors and/or proteins from the DBM, but where growth factors and/or proteins can be stable. The temperature can be less than 50° C. As another example, the temperature can be room temperature.

After mixing for the appropriate amount of time, the resulting demineralized bone extract can be separated from any insoluble DBM remaining in the solution. This separation can occur by any number of processes such as, but not limited to, decanting, filtering, or centrifuging. For example, the solution can be filtered to remove any soluble DBM remaining. The size of the sieve or filter will depend on the size of the DBM particles remaining, which can further depend on the initial form of DBM. For example, the filter can be from about 50 microns to about 300 microns. As another example, the filter can be a sieve, paper, sintered glass, woven or non-woven fabric, or any other means of filtering that is known in the art.

The demineralized bone extract can be diluted, neutralized or the weak acid or guanidine hydrochloride removed. Methods can include, but are not limited to, titration, dialysis, liquid-liquid extraction, hollow fiber filtration, ultrafiltration, crossflow filtration or precipitation. For example, the aqueous solution can be neutralized to a pH of from about 6.5 to about 7.5 by titration with an appropriate counterion. Such methods are well known in the art. As another example, the weak acid or guanidine hydrochloride can be removed by dialysis, hollow fiber filtration, ultrafiltration or crossflow filtration against a biologically compatible buffer, such as, but not limited to, Tris, TBS, phosphate, PBS or water, where the pH of the buffer can be from about 6.5 to about 7.5. The molecular weight cutoff of the dialysis membrane will depend on the size of the proteins and/or growth factors desired in the solution. The dialysis, hollow fiber filtration, ultrafiltration or crossflow filtration membrane can have, for example, a molecular weight cut off less than or equal to 12 Kd or from about 10 Kd to about 12 Kd. It is well known in the art how to select the molecular weight cut off of dialysis tubing to retain the desired molecules within the sample.

The demineralized bone extract can include the mineral coating solution or be mixed with the mineral coating solution as described herein. For example, the bone extract can be introduced during the scaffold incubation step in the mineral coating procedure as described in Example 4.

As described herein, a mineral coated scaffold can be coated simultaneously with the demineralized bone material or the mineral coated scaffold can be coated with the demineralizing bone material.

The demineralized bone extract can be applied to the scaffold such that the demineralized bone extract infiltrates the pores and passageways of the scaffold. For example, the demineralized bone extract can be applied to the scaffold under vacuum. As another example, the demineralized bone extract can be applied to the scaffold by dipping the structure into the extract and allowing it to infiltrate the pores and passageways by capillary action. After the demineralized bone extract has been applied to the scaffold, it can be dried onto the scaffold. The demineralized bone extract can be dried onto the structure by lyophilization, vacuum, heating, or a combination thereof. In one or more embodiments, the heating can be at a temperature less than 50° C.

As described herein, the method of the present invention can further comprise making a demineralized bone gelatin. The demineralized bone gelatin can be coated over the demineralized bone extract or mineral coating, or it can be mixed with the extract before coating to form a single coating or it can be mixed with the mineral coating to form a single coating. The demineralized bone gelatin can be formed by mixing DBM with an aqueous saline solution such as, but not limited to PBS, TBS, or a sodium chloride solution, to form a suspension. The suspension can be treated to increased temperature and pressure such as, but not limited to, autoclaved. In one illustrative embodiment, the solution can be heated to a temperature of from about 85° C. to about 130° C. at a pressure of at least about 15 psig. The DBM can be dissolved to produce a demineralized bone gelatin. Methods for forming a demineralized bone gelatin are known in the art. The DBM can be the solids removed during the filtering step while forming the demineralized bone extract or it can be fresh DBM. Alternatively, it will be appreciated that since the demineralized bone gelatin comprises mainly collagen, collagen of any purity can be substituted for the DBM.

The demineralized bone gelatin can be coated over the dried demineralized bone extract coating on the scaffold such that the gelatin coats the pores and passageways. Alternatively, the demineralized bone gelatin can be mixed with the demineralized bone extract prior to the extract being coated onto the scaffold to form a single coating. The scaffold can be pre-coated with the mineral coating or the mineral coating solution can be incorporated into the DBM coating. The coating comprising the demineralized bone extract and gelatin can then be applied to the scaffold such that the pores and passageways are coated. It will be appreciated that the demineralized bone gelatin can be less viscous at higher temperatures, making it easier to apply to the scaffold. The demineralized bone gelatin can be applied to the scaffold in a less viscous form such as a solution. The demineralized bone gelatin can be allowed to gel before any other steps are performed. The demineralized bone gelatin coating can be maintained at a temperature low enough as to not to inactivate any growth factors and/or proteins of the demineralized bone extract coating.

Once applied, the demineralized bone gelatin, either alone or mixed with the demineralized bone extract or mineral coating, can be dried onto the scaffold. The scaffold can be pre-coated with the mineral coating. The demineralized bone gelatin can be dried onto the structure by lyophilization, vacuum, heating, or a combination thereof. In one or more embodiments, the heating can be at a temperature not greater than 50° C.

As described herein, DBM can be integrated into the mineral coating or into a scaffold. For example, DBM can be integrated into the mineral coating or scaffold by % weight (w/w) or by % volume (v/v). A mineral coating or scaffold can comprise at least about 1% (w/w) DBM. For example, a mineral coating or scaffold can comprise at least about 1% (w/w) DBM; at least about 2% (w/w) DBM; at least about 3% (w/w) DBM; at least about 4% (w/w) DBM; at least about 5% (w/w) DBM; at least about 6% (w/w) DBM; at least about 7% (w/w) DBM; at least about 8% (w/w) DBM; at least about 9% (w/w) DBM; at least about 10% (w/w) DBM; at least about 11% (w/w) DBM; at least about 12% (w/w) DBM; at least about 13% (w/w) DBM; at least about 14% (w/w) DBM; at least about 15% (w/w) DBM; at least about 16% (w/w) DBM; at least about 17% (w/w) DBM; at least about 18% (w/w) DBM; at least about 19% (w/w) DBM; at least about 20% (w/w) DBM; at least about 21% (w/w) DBM; at least about 22% (w/w) DBM; at least about 23% (w/w) DBM; at least about 24% (w/w) DBM; at least about 25% (w/w) DBM; at least about 26% (w/w) DBM; at least about 27% (w/w) DBM; at least about 28% (w/w) DBM; at least about 29% (w/w) DBM; at least about 30% (w/w) DBM; at least about 31% (w/w) DBM; at least about 32% (w/w) DBM; at least about 33% (w/w) DBM; at least about 34% (w/w) DBM; at least about 35% (w/w) DBM; at least about 36% (w/w) DBM; at least about 37% (w/w) DBM; at least about 38% (w/w) DBM; at least about 39% (w/w) DBM; at least about 40% (w/w) DBM; at least about 41% (w/w) DBM; at least about 42% (w/w) DBM; at least about 43% (w/w) DBM; at least about 44% (w/w) DBM; at least about 45% (w/w) DBM; at least about 46% (w/w) DBM; at least about 47% (w/w) DBM; at least about 48% (w/w) DBM; at least about 49% (w/w) DBM; at least about 50% (w/w) DBM; at least about 51% (w/w) DBM; at least about 52% (w/w) DBM; at least about 53% (w/w) DBM; at least about 54% (w/w) DBM; at least about 55% (w/w) DBM; at least about 56% (w/w) DBM; at least about 57% (w/w) DBM; at least about 58% (w/w) DBM; at least about 59% (w/w) DBM; at least about 60% (w/w) DBM; at least about 61% (w/w) DBM; at least about 62% (w/w) DBM; at least about 63% (w/w) DBM; at least about 64% (w/w) DBM; at least about 65% (w/w) DBM; at least about 66% (w/w) DBM; at least about 67% (w/w) DBM; at least about 68% (w/w) DBM; at least about 69% (w/w) DBM; at least about 70% (w/w) DBM; at least about 71% (w/w) DBM; at least about 72% (w/w) DBM; at least about 73% (w/w) DBM; at least about 74% (w/w) DBM; at least about 75% (w/w) DBM; at least about 76% (w/w) DBM; at least about 77% (w/w) DBM; at least about 78% (w/w) DBM; at least about 79% (w/w) DBM; at least about 80% (w/w) DBM; at least about 81% (w/w) DBM; at least about 82% (w/w) DBM; at least about 83% (w/w) DBM; at least about 84% (w/w) DBM; at least about 85% (w/w) DBM; at least about 86% (w/w) DBM; at least about 87% (w/w) DBM; at least about 88% (w/w) DBM; at least about 89% (w/w) DBM; at least about 90% (w/w) DBM; at least about 91% (w/w) DBM; at least about 92% (w/w) DBM; at least about 93% (w/w) DBM; at least about 94% (w/w) DBM; at least about 95% (w/w) DBM; at least about 96% (w/w) DBM; at least about 97% (w/w) DBM; at least about 98% (w/w) DBM; or at least about 99% (w/w) DBM. It is understood that recitation of the above discrete values includes a range between each recited value.

As another example, a mineral coating or scaffold can comprise about 1% (w/w) DBM; about 2% (w/w) DBM; about 3% (w/w) DBM; about 4% (w/w) DBM; about 5% (w/w) DBM; about 6% (w/w) DBM; about 7% (w/w) DBM; about 8% (w/w) DBM; about 9% (w/w) DBM; about 10% (w/w) DBM; about 11% (w/w) DBM; about 12% (w/w) DBM; about 13% (w/w) DBM; about 14% (w/w) DBM; about 15% (w/w) DBM; about 16% (w/w) DBM; about 17% (w/w) DBM; about 18% (w/w) DBM; about 19% (w/w) DBM; about 20% (w/w) DBM, about 21% (w/w) DBM; about 22% (w/w) DBM; about 23% (w/w) DBM; about 24% (w/w) DBM; about 25% (w/w) DBM; about 26% (w/w) DBM; about 27% (w/w) DBM; about 28% (w/w) DBM;

about 29% (w/w) DBM; about 30% (w/w) DBM; about 31% (w/w) DBM; about 32% (w/w) DBM; about 33% (w/w) DBM; about 34% (w/w) DBM; about 35% (w/w) DBM; about 36% (w/w) DBM; about 37% (w/w) DBM; about 38% (w/w) DBM; about 39% (w/w) DBM; about 40% (w/w) DBM; about 41% (w/w) DBM; about 42% (w/w) DBM; about 43% (w/w) DBM; about 44% (w/w) DBM; about 45% (w/w) DBM; about 46% (w/w) DBM; about 47% (w/w) DBM; about 48% (w/w) DBM; about 49% (w/w) DBM; about 50% (w/w) DBM; about 51% (w/w) DBM; about 52% (w/w) DBM; about 53% (w/w) DBM; about 54% (w/w) DBM; about 55% (w/w) DBM; about 56% (w/w) DBM; about 57% (w/w) DBM; about 58% (w/w) DBM; about 59% (w/w) DBM; about 60% (w/w) DBM; about 61% (w/w) DBM; about 62% (w/w) DBM; about 63% (w/w) DBM; about 64% (w/w) DBM; about 65% (w/w) DBM; about 66% (w/w) DBM; about 67% (w/w) DBM; about 68% (w/w) DBM; about 69% (w/w) DBM; about 70% (w/w) DBM; about 71% (w/w) DBM; about 72% (w/w) DBM; about 73% (w/w) DBM; about 74% (w/w) DBM; about 75% (w/w) DBM; about 76% (w/w) DBM; about 77% (w/w) DBM; about 78% (w/w) DBM; about 79% (w/w) DBM; about 80% (w/w) DBM; about 81% (w/w) DBM; about 82% (w/w) DBM; about 83% (w/w) DBM; about 84% (w/w) DBM; about 85% (w/w) DBM; about 86% (w/w) DBM; about 87% (w/w) DBM; about 88% (w/w) DBM; about 89% (w/w) DBM; about 90% (w/w) DBM; about 91% (w/w) DBM; about 92% (w/w) DBM; about 93% (w/w) DBM; about 94% (w/w) DBM; about 95% (w/w) DBM; about 96% (w/w) DBM; about 97% (w/w) DBM; about 98% (w/w) DBM; or about 99% (w/w) DBM. It is understood that recitation of the above discrete values includes a range between each recited value.

A mineral coating or scaffold can comprise at least about 1% (v/v) DBM. As another example, a mineral coating or scaffold can comprise at least about 1% (v/v) DBM; at least about 2% (v/v) DBM; at least about 3% (v/v) DBM; at least about 4% (v/v) DBM; at least about 5% (v/v) DBM; at least about 6% (v/v) DBM; at least about 7% (v/v) DBM; at least about 8% (v/v) DBM; at least about 9% (v/v) DBM; at least about 10% (v/v) DBM; at least about 11% (v/v) DBM; at least about 12% (v/v) DBM; at least about 13% (v/v) DBM; at least about 14% (v/v) DBM; at least about 15% (v/v) DBM; at least about 16% (v/v) DBM; at least about 17% (v/v) DBM; at least about 18% (v/v) DBM; at least about 19% (v/v) DBM; at least about 20% (v/v) DBM; at least about 21% (v/v) DBM; at least about 22% (v/v) DBM; at least about 23% (v/v) DBM; at least about 24% (v/v) DBM; at least about 25% (v/v) DBM; at least about 26% (v/v) DBM; at least about 27% (v/v) DBM; at least about 28% (v/v) DBM; at least about 29% (v/v) DBM; at least about 30% (v/v) DBM; at least about 31% (v/v) DBM; at least about 32% (v/v) DBM; at least about 33% (v/v) DBM; at least about 34% (v/v) DBM; at least about 35% (v/v) DBM; at least about 36% (v/v) DBM; at least about 37% (v/v) DBM; at least about 38% (v/v) DBM; at least about 39% (v/v) DBM; at least about 40% (v/v) DBM; at least about 41% (v/v) DBM; at least about 42% (v/v) DBM; at least about 43% (v/v) DBM; at least about 44% (v/v) DBM; at least about 45% (v/v) DBM; at least about 46% (v/v) DBM; at least about 47% (v/v) DBM; at least about 48% (v/v) DBM; at least about 49% (v/v) DBM; at least about 50% (v/v) DBM; at least about 51% (v/v) DBM; at least about 52% (v/v) DBM; at least about 53% (v/v) DBM; at least about 54% (v/v) DBM; at least about 55% (v/v) DBM; at least about 56% (v/v) DBM; at least about 57% (v/v) DBM; at least about 58% (v/v) DBM; at least about 59% (v/v) DBM; at least about 60% (v/v) DBM; at least about 61% (v/v) DBM; at least about 62% (v/v) DBM; at least about 63% (v/v) DBM; at least about 64% (v/v) DBM; at least about 65% (v/v) DBM; at least about 66% (v/v) DBM; at least about 67% (v/v) DBM; at least about 68% (v/v) DBM; at least about 69% (v/v) DBM; at least about 70% (v/v) DBM; at least about 71% (v/v) DBM; at least about 72% (v/v) DBM; at least about 73% (v/v) DBM; at least about 74% (v/v) DBM; at least about 75% (v/v) DBM; at least about 76% (v/v) DBM; at least about 77% (v/v) DBM; at least about 78% (v/v) DBM; at least about 79% (v/v) DBM; at least about 80% (v/v) DBM; at least about 81% (v/v) DBM; at least about 82% (v/v) DBM; at least about 83% (v/v) DBM; at least about 84% (v/v) DBM; at least about 85% (v/v) DBM; at least about 86% (v/v) DBM; at least about 87% (v/v) DBM; at least about 88% (v/v) DBM; at least about 89% (v/v) DBM; at least about 90% (v/v) DBM; at least about 91% (v/v) DBM; at least about 92% (v/v) DBM; at least about 93% (v/v) DBM; at least about 94% (v/v) DBM; at least about 95% (v/v) DBM; at least about 96% (v/v) DBM; at least about 97% (v/v) DBM; at least about 98% (v/v) DBM; or at least about 99% (v/v) DBM. It is understood that recitation of the above discrete values includes a range between each recited value.

As another example, a mineral coating or scaffold can comprise about 1% (v/v) DBM; about 2% (v/v) DBM; about 3% (v/v) DBM; about 4% (v/v) DBM; about 5% (v/v) DBM; about 6% (v/v) DBM; about 7% (v/v) DBM; about 8% (v/v) DBM; about 9% (v/v) DBM; about 10% (v/v) DBM; about 11% (v/v) DBM; about 12% (v/v) DBM; about 13% (v/v) DBM; about 14% (v/v) DBM; about 15% (v/v) DBM; about 16% (v/v) DBM; about 17% (v/v) DBM; about 18% (v/v) DBM; about 19% (v/v) DBM; about 20% (v/v) DBM; about 21% (v/v) DBM; about 22% (v/v) DBM; about 23% (v/v) DBM; about 24% (v/v) DBM; about 25% (v/v) DBM; about 26% (v/v) DBM; about 27% (v/v) DBM; about 28% (v/v) DBM; about 29% (v/v) DBM; about 30% (v/v) DBM; about 31% (v/v) DBM; about 32% (v/v) DBM; about 33% (v/v) DBM; about 34% (v/v) DBM; about 35% (v/v) DBM; about 36% (v/v) DBM; about 37% (v/v) DBM; about 38% (v/v) DBM; about 39% (v/v) DBM; about 40% (v/v) DBM; about 41% (v/v) DBM; about 42% (v/v) DBM; about 43% (v/v) DBM; about 44% (v/v) DBM; about 45% (v/v) DBM; about 46% (v/v) DBM; about 47% (v/v) DBM; about 48% (v/v) DBM; about 49% (v/v) DBM; about 50% (v/v) DBM; about 51% (v/v) DBM; about 52% (v/v) DBM; about 53% (v/v) DBM; about 54% (v/v) DBM; about 55% (v/v) DBM; about 56% (v/v) DBM; about 57% (v/v) DBM; about 58% (v/v) DBM; about 59% (v/v) DBM; about 60% (v/v) DBM; about 61% (v/v) DBM; about 62% (v/v) DBM; about 63% (v/v) DBM; about 64% (v/v) DBM; about 65% (v/v) DBM; about 66% (v/v) DBM; about 67% (v/v) DBM; about 68% (v/v) DBM; about 69% (v/v) DBM; about 70% (v/v) DBM; about 71% (v/v) DBM; about 72% (v/v) DBM; about 73% (v/v) DBM; about 74% (v/v) DBM; about 75% (v/v) DBM; about 76% (v/v) DBM; about 77% (v/v) DBM; about 78% (v/v) DBM; about 79% (v/v) DBM; about 80% (v/v) DBM; about 81% (v/v) DBM; about 82% (v/v) DBM; about 83% (v/v) DBM; about 84% (v/v) DBM; about 85% (v/v) DBM; about 86% (v/v) DBM; about 87% (v/v) DBM; about 88% (v/v) DBM; about 89% (v/v) DBM; about 90% (v/v) DBM; about 91% (v/v) DBM; about 92% (v/v) DBM; about 93% (v/v) DBM; about 94% (v/v) DBM; about 95% (v/v) DBM; about 96% (v/v) DBM; about 97% (v/v) DBM; about 98% (v/v) DBM; or about 99% (v/v) DBM. It is understood that recitation of the above discrete values includes a range between each recited value.

As described herein, an auxiliary component can be an antimicrobial agent. For example, an antimicrobial agent can be silver particles. As another example, silver particles can be silver microparticles or silver nanoparticles. Silver particles integrated with the scaffold are presently thought to provide biostatic, anti-infection properties to the scaffold.

As described herein, silver particles can be integrated onto the mineral coating or scaffold. For example, the silver particles can be integrated into the scaffold or coating before, during, or after DBM integration.

As described herein, silver particles can be incorporated onto the surface of a mineral coated scaffold. For example, the silver particles can be incorporated into or onto the mineral coating by any method known in the art. As another example, the incorporation of silver particles can be as described in Lee et al. 2013 Mat. Views 25, 1173-1179; WO 2014/110284; U.S. Pat. No. 8,673,018; US 2013/0142885; Ciobanu (2014); Jadalannagari (2014); US 2009/0198344.

As described herein, mineral coated scaffolds can be incubated in citric acid solution and silver nitrate solution to produce silver nanoparticles or microparticles on the mineral coating.

As described herein, the mineral coated scaffold can be incubated in citric acid solution. For example, the citric acid solution can be from about 0.1 mM to 100 mM citric acid solution. As another example, the concentration of citric acid solution can be at least about 0.1 mM citric acid. As another example, the concentration of citric acid solution can be at least about 0.1 mM citric acid; at least about 0.2 mM citric acid; at least about 0.3 mM citric acid; at least about 0.4 mM citric acid; at least about 0.5 mM citric acid; at least about 0.6 mM citric acid; at least about 0.7 mM citric acid; at least about 0.8 mM citric acid; at least about 0.9 mM citric acid; at least about 1 mM citric acid; at least about 1.5 mM citric acid; at least about 2 mM citric acid; at least about 2.5 mM citric acid; at least about 3.0 mM citric acid; at least about 3.5 mM citric acid; at least about 4.0 mM citric acid; at least about 4.5 mM citric acid; at least about 5.0 mM citric acid; at least about 5.5 mM citric acid; at least about 6.0 mM citric acid; at least about 6.5 mM citric acid; at least about 7.0 mM citric acid; at least about 7.5 mM citric acid; at least about 8.0 mM citric acid; at least about 8.5 mM citric acid; at least about 9.0 mM citric acid; at least about 9.5 mM citric acid; at least about 10 mM citric acid; at least about 15 mM citric acid; at least about 20 mM citric acid; at least about 25 mM citric acid; at least about 30 mM citric acid; at least about 35 mM citric acid; at least about 40 mM citric acid; at least about 45 mM citric acid; at least about 50 mM citric acid; at least about 55 mM citric acid; at least about 60 mM citric acid; at least about 65 mM citric acid; at least about 70 mM citric acid; at least about 75 mM citric acid; at least about 80 mM citric acid; at least about 85 mM citric acid; at least about 90 mM citric acid; at least about 95 mM citric acid; at least about; or 100 mM citric acid. It is understood that recitation of the above discrete values includes a range between each recited value.

As described herein, the concentration of citric acid solution can be about 0.1 mM citric acid; at least about 0.2 mM citric acid; about 0.3 mM citric acid; about 0.4 mM citric acid; about 0.5 mM citric acid; about 0.6 mM citric acid; about 0.7 mM citric acid; about 0.8 mM citric acid; about 0.9 mM citric acid; about 1 mM citric acid; about 1.5 mM citric acid; about 2 mM citric acid; about 2.5 mM citric acid; about 3.0 mM citric acid; about 3.5 mM citric acid; about 4.0 mM citric acid; about 4.5 mM citric acid; about 5.0 mM citric acid; about 5.5 mM citric acid; about 6.0 mM citric acid; about 6.5 mM citric acid; about 7.0 mM citric acid; about 7.5 mM citric acid; about 8.0 mM citric acid; about 8.5 mM citric acid; about 9.0 mM citric acid; about 9.5 mM citric acid; about 10 mM citric acid; about 15 mM citric acid; about 20 mM citric acid; about 25 mM citric acid; about 30 mM citric acid; about 35 mM citric acid; about 40 mM citric acid; about 45 mM citric acid; about 50 mM citric acid; about 55 mM citric acid; about 60 mM citric acid; about 65 mM citric acid; about 70 mM citric acid; about 75 mM citric acid; about 80 mM citric acid; about 85 mM citric acid; about 90 mM citric acid; about 95 mM citric acid; about; or 100 mM citric acid. It is understood that recitation of the above discrete values includes a range between each recited value.

As described herein, the mineral coated scaffold can be incubated in citric acid solution for about 0.1 hours to about 40 hours. For example, the mineral coated scaffold can be incubated for about 0.5 hours to about 4 hours. It is understood that recitation of the above ranges includes discrete values within each recited range.

As described herein, the mineral coated scaffold can be incubated in citric acid solution for at least about 0.1 hours. For example, the mineral coated scaffold can be incubated in citric acid solution for at least about 0.1 hours; at least about 0.2 hours; at least about 0.3 hours; at least about 0.4 hours; at least about 0.5 hours; at least about 0.6 hours; at least about 0.7 hours; at least about 0.8 hours; at least about 0.9 hours; at least about 1 hours; at least about 1.1 hours; at least about 1.2 hours; at least about 1.3 hours; at least about 1.4 hours; at least about 1.5 hours; at least about 1.6 hours; at least about 1.7 hours; at least about 1.8 hours; at least about 1.9 hours; at least about 2 hours; at least about 2.1 hours; at least about 2.2 hours; at least about 2.3 hours; at least about 2.4 hours; at least about 2.5 hours; at least about 2.6 hours; at least about 2.7 hours; at least about 2.8 hours; at least about 2.9 hours; at least about 3.0 hours; at least about 3.1 hours; at least about 3.2 hours; at least about 3.3 hours; at least about 3.4 hours; at least about 3.5 hours; at least about 3.6 hours; at least about 3.7 hours; at least about 3.8 hours; at least about 3.9 hours; at least about 4.0 hours; at least about 4.5 hours; at least about 5 hours; at least about 5.5 hours; at least about 6.0 hours; at least about 6.5 hours; at least about 7.0 hours; at least about 7.5 hours; at least about 8.0 hours; at least about 8.5 hours; at least about 9.0 hours; at least about 9.5 hours; at least about 10 hours; at least about 11 hours; at least about 12 hours; at least about 13 hours; at least about 14 hours; at least about 15 hours; at least about 16 hours; at least about 17 hours; at least about 18 hours; at least about 19 hours; at least about 20 hours; at least about 21 hours; at least about 22 hours; at least about 23 hours; at least about 24 hours; at least about 25 hours; at least about 26 hours; at least about 27 hours; at least about 28 hours; at least about 29 hours; at least about 30 hours; at least about 31 hours; at least about 32 hours; at least about 33 hours; at least about 34 hours; at least about 35 hours; at least about 36 hours; at least about 37 hours; at least about 38 hours; at least about 39 hours; or at least about 40 hours. It is understood that recitation of the above discrete values includes a range between each recited value.

As another example, the mineral coated scaffold can be incubated in citric acid solution for about 0.1 hours; about 0.2 hours; about 0.3 hours; about 0.4 hours; about 0.5 hours; about 0.6 hours; about 0.7 hours; about 0.8 hours; about 0.9 hours; about 1 hours; about 1.1 hours; about 1.2 hours; about 1.3 hours; about 1.4 hours; about 1.5 hours; about 1.6 hours; about 1.7 hours; about 1.8 hours; about 1.9 hours; about 2.0 hours; about 2.1 hours; about 2.2 hours; about 2.3 hours; about 2.4 hours; about 2.5 hours; about 2.6 hours; about 2.7 hours; about 2.8 hours; about 2.9 hours; about 3.0 hours; about 3.1 hours; about 3.2 hours; about 3.3 hours; about 3.4 hours; about 3.5 hours; about 3.6 hours; about 3.7 hours; about 3.8 hours; about 3.9 hours; about 4.0 hours; about 4.5 hours; about 5 hours; about 5.5 hours; about 6.0 hours; about 6.5 hours; about 7.0 hours; about 7.5 hours; about 8.0 hours; about 8.5 hours; about 9.0 hours; about 9.5 hours; about 10 hours; about 11 hours; about 12 hours; about 13 hours; about 14 hours; about 15 hours; about 16 hours; about 17 hours; about 18 hours; about 19 hours; about 20 hours; about 21 hours; about 22 hours; about 23 hours; about 24 hours; about 25 hours; about 26 hours; about 27 hours; about 28 hours; about 29 hours; about 30 hours; about 31 hours; about 32 hours; about 33 hours; about 34 hours; about 35 hours; about 36 hours; about 37 hours; about 38 hours; about 39 hours; or about 40 hours. It is understood that recitation of the above discrete values includes a range between each recited value.

The citric acid-treated mineral-coated scaffolds can then be transferred to a silver nitrate solution to grow silver particles. Silver particles can cover the entire coated scaffold. The size of silver particles can be increased with longer silver nitrate incubation time and higher silver nitrate concentrations, whereas citric acid incubation time and concentration have not been shown to influence the silver particle size.

As described herein, silver particles can be synthesized on both citric acid-treated and non-citric-acid-treated mineral-coated scaffolds, because the size and morphology of the silver particles between these two groups can be the same. Silver carbonate and silver phosphate particles can be created locally on a mineral coated scaffold by the reaction of silver ions with carbonate or phosphate ions dissolved from CaP in a mineral coating.

As described herein, the time course release of silver which was prepared from different incubating conditions can be measured. The silver release from mineral coatings can continue for time periods ranging from 3 days to over 30 days, and the total quantity of released silver species can range from 0.7 μg to 75.4 μg per $cm^2$ of sample surface. The silver release can occur with nearly linear release kinetics in groups treated with citric acid, while the groups not treated with citric acid can show an initial burst release during the first two days. These release kinetics can be dictated by the different dissolution rates of CaP coatings in presence of adsorbed citric acid molecules. Burst release can pose a practical problem in the application of drug delivery systems, because it can occur in an unpredictable manner and may cause negative side effects due to overdose of the released drug. Citric acid treatment can help avoid burst release of silver species, and thereby prevent complications that may be related to silver overdose. The 4-hour incubation in citric acid solution can lead to more rapid release kinetics compared to 0.5 and 1 hour incubations. The silver release kinetics was not shown to be influenced by the citric acid concentration. This trend suggests that the amount of released silver can be dictated by the adsorbed citric acid and thus dissolution of mineral coatings. Increase of incubation time (e.g., 0.5 to 4 hr) in silver nitrate solution can result in a larger amount of silver released.

Similarly, higher concentrations of silver nitrate solution during growth of silver particles can lead to larger quantities of silver released over longer release periods. Taken together, these results can indicate that the dosage or timeframe of silver release could be readily controlled by varying the conditions during growth of silver salt particles on the mineral coated scaffold.

The antibacterial activity of released silver can be evaluated against a bacterial culture. For example, antibacterial activity of released silver can be evaluated against Staphylococcus and gram-negative Escherichia coli. Media from silver-releasing CaP coatings can be added to bacterial suspensions in their exponential growth phase, and bacterial growth can be monitored by measuring optical density at 600 nm.

Silver released into the media can have antibacterial activity that is similar against *S. aureus* or *E. coli*. Silver released at a later time point can remain antimicrobially active. Because previous studies reported that citric acid can be effective to treat chronic wound infection by preventing colony formation of microorganism, the citric acid can also be beneficial to the antibacterial properties of the silver nanoparticle-incorporated mineral-coated scaffold.

As described herein, silver particles can cover the surface of the mineral coating or scaffold with at least about 1% coverage. For example, the silver particles can cover the surface of the mineral coating or scaffold with at least about 1% coverage; at least about 2% coverage; at least about 3% coverage; at least about 4% coverage; at least about 5% coverage; at least about 6% coverage; at least about 7% coverage; at least about 8% coverage; at least about 9% coverage; at least about 10% coverage; at least about 11% coverage; at least about 12% coverage; at least about 13% coverage; at least about 14% coverage; at least about 15% coverage; at least about 16% coverage; at least about 17% coverage; at least about 18% coverage; at least about 19% coverage; at least about 20% coverage; at least about 21% coverage; at least about 22% coverage; at least about 23% coverage; at least about 24% coverage; at least about 25% coverage; at least about 26% coverage; at least about 27% coverage; at least about 28% coverage; at least about 29% coverage; at least about 30% coverage; at least about 31% coverage; at least about 32% coverage; at least about 33% coverage; at least about 34% coverage; at least about 35% coverage; at least about 36% coverage; at least about 37% coverage; at least about 38% coverage; at least about 39% coverage; at least about 40% coverage; at least about 41% coverage; at least about 42% coverage; at least about 43% coverage; at least about 44% coverage; at least about 45% coverage; at least about 46% coverage; at least about 47% coverage; at least about 48% coverage; at least about 49% coverage; at least about 50% coverage; at least about 51% coverage; at least about 52% coverage; at least about 53% coverage; at least about 54% coverage; at least about 55% coverage; at least about 56% coverage; at least about 57% coverage; at least about 58% coverage; at least about 59% coverage; at least about 60% coverage; at least about 61% coverage; at least about 62% coverage; at least about 63% coverage; at least about 64% coverage; at least about 65% coverage; at least about 66% coverage; at least about 67% coverage; at least about 68% coverage; at least about 69% coverage; at least about 70% coverage; at least about 71% coverage; at least about 72% coverage; at least about 73% coverage; at least about 74% coverage; at least about 75% coverage; at least about 76% coverage; at least about 77% coverage; at least about 78% coverage; at least about 79% coverage; at least about 80% coverage; at least about 81% coverage; at least about 82% coverage; at least about 83% coverage; at least about 84% coverage; at least about 85% coverage; at least about 86% coverage; at least about 87% coverage; at least about 88% coverage; at least about 89% coverage; at least about 90% coverage; at least about 91% coverage; at least about 92% coverage; at least about 93% coverage; at least about 94% coverage; at least about 95% coverage; at least about 96% coverage; at least about 97% coverage; at least about 98% coverage; or at least about 99% coverage. It is understood that recitation of the above discrete values includes a range between each recited value.

As described herein, the silver particles can cover the surface of the mineral coating or scaffold with at least about 1% coverage; about 2% coverage; about 3% coverage; about 4% coverage; about 5% coverage; about 6% coverage; about 7% coverage; about 8% coverage; about 9% coverage; about 10% coverage; about 11% coverage; about 12% coverage; about 13% coverage; about 14% coverage; about 15% coverage; about 16% coverage; about 17% coverage; about 18% coverage; about 19% coverage; about 20% coverage; about 21% coverage; about 22% coverage; about 23% coverage; about 24% coverage; about 25% coverage; about 26% coverage; about 27% coverage; about 28% coverage; about 29% coverage; about 30% coverage; about 31% coverage; about 32% coverage; about 33% coverage; about 34% coverage; about 35% coverage; about 36% coverage; about 37% coverage; about 38% coverage; about 39% coverage; about 40% coverage; about 41% coverage; about 42% coverage; about 43% coverage; about 44% coverage; about 45% coverage; about 46% coverage; about 47% coverage; about 48% coverage; about 49% coverage; about 50% coverage; about 51% coverage; about 52% coverage; about 53% coverage; about 54% coverage; about 55% coverage; about 56% coverage; about 57% coverage; about 58% coverage; about 59% coverage; about 60% coverage; about 61% coverage; about 62% coverage; about 63% coverage; about 64% coverage; about 65% coverage; about 66% coverage; about 67% coverage; about 68% coverage; about 69% coverage; about 70% coverage; about 71% coverage; about 72% coverage; about 73% coverage; about 74% coverage; about 75% coverage; about 76% coverage; about 77% coverage; about 78% coverage; about 79% coverage; about 80% coverage; about 81% coverage; about 82% coverage; about 83% coverage; about 84% coverage; about 85% coverage; about 86% coverage; about 87% coverage; about 88% coverage; about 89% coverage; about 90% coverage; about 91% coverage; about 92% coverage; about 93% coverage; about 94% coverage; about 95% coverage; about 96% coverage; about 97% coverage; about 98% coverage; or about 99% coverage. It is understood that recitation of the above discrete values includes a range between each recited value.

Although the embodiments described herein describe single layers of coatings, more than one coating or application of the mineral coating, DBM, or silver particles may be applied.

Buffers

The buffer, as described herein, can be used in the modified simulated body fluid. The buffer, as described herein, can be any conventional buffer. A buffer can be as described in U.S. application Ser. Nos. 13/407,441; 13/879,178; and 13/036,470 and are incorporated by reference.

For example, the buffer can be a saline buffer. As another example, the buffer can be Tris. Tris can be tris-buffered saline (TBS). Tris can be Tris HCl. As another example, the buffer can be PBS. PBS can be DPBS. As another example a buffer can be a mixture including citric acid, monopotassium phosphate, boric acid, or diethyl barbituric acid. As another example a buffer can be TAPS, Bicine, Tricine, TAPSO, HEES, TES, MOPS, PIPES, Cacodylate, SSC, MES, or succinic acid.

The buffer, as described herein, can be at any conventional concentration. For example, the concentration of buffer in the simulated body fluid can be at least about 1 mM buffer. As another example, the concentration of buffer in the simulated body fluid can be at least about 2 mM buffer; at least about 3 mM buffer; at least about 4 mM buffer; at least about 5 mM buffer; at least about 6 mM buffer; at least about 7 mM buffer; at least about 8 mM buffer; at least about 9 mM buffer; at least about 10 mM buffer; at least about 11 mM buffer; at least about 12 mM buffer; at least about 13 mM buffer; at least about 14 mM buffer; at least about 15 mM buffer; at least about 16 mM buffer; at least about 17 mM buffer; at least about 18 mM buffer; at least about 19 mM buffer; at least about 20 mM buffer; at least about 21 mM buffer; at least about 22 mM buffer; at least about 23 mM buffer; at least about 24 mM buffer; at least about 25 mM buffer; at least about 26 mM buffer; at least about 27 mM buffer; at least about 28 mM buffer; at least about 29 mM buffer; at least about 30 mM buffer; at least about 31 mM buffer; at least about 32 mM buffer; at least about 33 mM buffer; at least about 34 mM buffer; at least about 35 mM buffer; at least about 36 mM buffer; at least about 37 mM buffer; at least about 38 mM buffer; at least about 39 mM buffer; at least about 40 mM buffer; at least about 50 mM buffer; at least about 60 mM buffer; at least about 70 mM buffer; at least about 80 mM buffer; at least about 90 mM buffer; at least about 100 mM buffer; at least about 110 mM buffer; at least about 120 mM buffer; at least about 130 mM buffer; at least about 140 mM buffer; at least about 150 mM buffer; at least about 160 mM buffer; at least about 170 mM buffer; at least about 180 mM buffer; at least about 190 mM buffer; or at least about 200 mM buffer. It is understood that recitation of the above discrete values includes a range between each recited value.

As another example, the concentration of buffer in the simulated body fluid can be about 1 mM buffer; about 2 mM buffer; about 3 mM buffer; about 4 mM buffer; about 5 mM buffer; about 6 mM buffer; about 7 mM buffer; about 8 mM buffer; about 9 mM buffer; about 10 mM buffer; about 11 mM buffer; about 12 mM buffer; about 13 mM buffer; about 14 mM buffer; about 15 mM buffer; about 16 mM buffer; about 17 mM buffer; about 18 mM buffer; about 19 mM buffer; about 20 mM buffer; about 21 mM buffer; about 22 mM buffer; about 23 mM buffer; about 24 mM buffer; about 25 mM buffer; about 26 mM buffer; about 27 mM buffer; about 28 mM buffer; about 29 mM buffer; about 30 mM buffer; about 31 mM buffer; about 32 mM buffer; about 33 mM buffer; about 34 mM buffer; about 35 mM buffer; about 36 mM buffer; about 37 mM buffer; about 38 mM buffer; about 39 mM buffer; about 40 mM buffer; about 50 mM buffer; about 60 mM buffer; about 70 mM buffer; about 80 mM buffer; about 90 mM buffer; about 100 mM buffer; about 110 mM buffer; about 120 mM buffer; about 130 mM buffer; about 140 mM buffer; about 150 mM buffer; about 160 mM buffer; about 170 mM buffer; about 180 mM buffer; about 190 mM buffer; or about 200 mM buffer. It is understood that recitation of the above discrete values includes a range between each recited value.

A buffer can be held at any pH conventional in the art. For example, a buffer can have a pH in the range of 2 to 11. As another example, a buffer can have a pH value of at least about 2. As another example, a buffer can have a pH value of at least about 2; a pH value of at least about 2.5; a pH value of at least about 3; a pH value of at least about 3.5; a pH value of at least about 4; a pH value of at least about 4.5; a pH value of at least about 5; a pH value of at least about 5.5; a pH value of at least about 6; a pH value of at least about 6.1; a pH value of at least about 6.2; a pH value of at least about 6.3; a pH value of at least about 6.4; a pH value of at least about 6.5; a pH value of at least about 6.6; a pH value of at least about 6.7; a pH value of at least about 6.8; a pH value of at least about 6.9; a pH value of at least about 7; a pH value of at least about 7.1; a pH value of at least about 7.2; a pH value of at least about 7.3; a pH value of at least about 7.4; a pH value of at least about 7.5; a pH value of at least about 7.6; a pH value of at least about 7.7; a pH value of at least about 7.8; a pH value of at least about 7.9; a pH value of at least about 8; a pH value of at least about 8.5; a pH value of at least about 9; a pH value of at least about 9.5; a pH value of at least about 10; a pH value of at least about 11. It is understood that recitation of the above discrete values includes a range between each recited value.

As another example, a buffer can have a pH value of about 2; a pH value of about 2.5; a pH value of about 3; a pH value of about 3.5; a pH value of about 4; a pH value of about 4.5; a pH value of about 5; a pH value of about 5.5; a pH value of about 6; a pH value of about 6.1; a pH value of about 6.2; a pH value of about 6.3; a pH value of about 6.4; a pH value of about 6.5; a pH value of about 6.6; a pH value of about 6.7; a pH value of about 6.8; a pH value of about 6.9; a pH value of about 7; a pH value of about 7.1; a pH value of about 7.2; a pH value of about 7.3; a pH value of about 7.4; a pH value of about 7.5; a pH value of about 7.6; a pH value of about 7.7; a pH value of about 7.8; a pH value of about 7.9; a pH value of about 8; a pH value of about 8.5; a pH value of about 9; a pH value of about 9.5; a pH value of about 10; a pH value of about 11. It is understood that recitation of the above discrete values includes a range between each recited value.

As another example, a buffer can have a pH value that is physiologically relevant. A buffer can have a pH value of about 6 to about 8.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a scaffold, a modified simulated body fluid solution, a primer solution, a polymer, a solvent, or any other agent as described above. Such packaging of the components separately can, if desired, be presented in a pack or dispenser device which can contain one or more unit dosage forms containing the composition. The pack can, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1

Mineral Coating

The following example describes the mineralization of a polycaprolactone (PCL) scaffold.

A PCL scaffold was hydrolyzed in a 1.0 M NaOH solution for 60 minutes to produce a hydrolyzed, carboxylic acid-rich surface. After hydrolysis of the PCL scaffold, a bone mineral coating was formed by immersion of a PCL scaffold in modified simulated body fluid (mSBF) and incubated.

The mSBF in this example was an inorganic solution having a similar composition to human plasma but with double the concentration of calcium and phosphate to enhance mineral growth, without organic components, at physiological conditions, and continuous rotations. The mSBF solution was prepared according to the following. The following reagents were added to ddH$_2$O in the order shown: 141 mM NaCl, 4.0 mM KCl, 1.0 mM MgCl$_2$, 0.5 mM MgSO$_4$, 4.2 mM NaHCO$_3$, 20 mM Tris, 5 mM CaCl$_2$, and 2.0 mM KH$_2$PO$_4$. The solution was slowly heated to 37° C. and was adjusted to a final pH of 6.8 using HCl and/or NaOH buffer solutions.

Figure 1B:
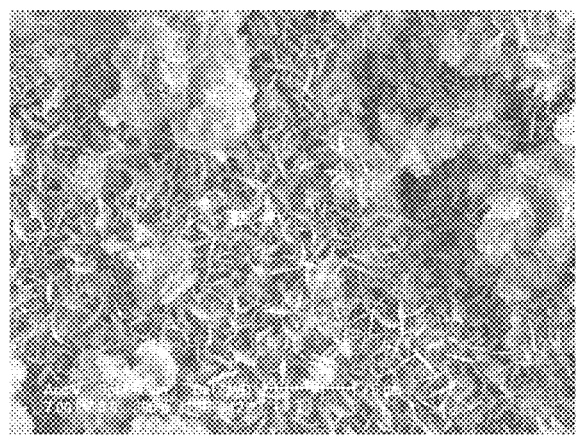

The incubation period was varied from 5 to 14 days. The mSBF solution was renewed every two days in order to maintain consistent ionic strength throughout the coating process. The apatite (a group of calcium phosphates including bone mineral and the main inorganic constituent of bones and teeth similar to hydroxyapatite) was nucleated and grown on the surface of the PCL scaffold to form an integral part of the coated PCL scaffold (see e.g., FIG. 1A-B). The mechanism for mineral nucleation and growth on PCL is thought to be based on the interaction of carboxylate ions and hydroxyl groups on the hydrolyzed PCL surface with calcium- and phosphate-rich nuclei in mSBF solution. This mineral growth process is thought to mimic natural biomineralization processes and results in a mineral coating that is similar in structure (plate-like nanostructure) and composition (carbonate-substituted, calcium-deficient hydroxyapatite phase) to human bone mineral. Ca-deficient HA was measured by Ca/P ratio. Chemicals for mSBF preparation were powder reagent grade chemicals. Water used was in accordance with ISO3696:1987, grade 2.

After mineral coating, the scaffold was rinsed for 15 minutes in ddH$_2$O to remove residual salts and was freeze dried overnight in a lyophilizer at a temperature of −40° C., under vacuum.

Example 2

Mineral Coating Specifications

The following example describes the coating specifications.

The assessment of mineral formation was performed by determining the change in mass after coating compared with the initial mass (before coating).

Conditions were found to achieve a desired bone mineral coating on implants (see e.g., TABLE 1).

TABLE 1

Parameters for bone mineral coating on implants
Coating Specification (Coating alone)

| Property | Description | Analytical Method |
|---|---|---|
| Chemical composition and concentration (%) | 97% Hydroxyapatite 3% Octacalcium phosphate | XRD |
| Ca/P ratio after heat treatment at 1000° C., According to ISO 13779-2 | $1.67 \leq Ca/P \leq 1.76$ | XRD |
| Crystalline phase | Hydroxyapatite and octacalcium phosphate | XRD (2θ in the range of 15-35°, specifically at 25.8°, 28.1°, 28.9°, 31.8°, and 32.1°) and FTIR (peaks in the 1400-1500 $cm^{-1}$ region (for carbonate peaks) and 900-1100 $cm^{-1}$ region (for phosphate peaks) |
| % Crystallinity | 96.5% | XRD |
| Porosity (%) | 20-28%* | SEM/Image J |
| Pore size (nm) | 100-350 nm* | SEM/Image J |
| Heavy metal trace element (ppm) as ref. in ISO 13779-3 | Arsenic (As) < 2.1 ppm Cadmium (Cd) < 0.1 ppm Lead (Pb) < 0.1 ppm Mercury (Hg) < 4.7 ppm | EDX for element identification, ICP for element concentrations |

TRS- SP0019-01 Bone Mineral Coating,
*Porosity and pore size studies of C-BVF

Example 3

Mineral Coating Dissolution

The following example describes coating dissolution rate in various medium conditions. It was shown that the phosphate buffer provided decreased coating dissolution compared to Tris.

Figure 2A:
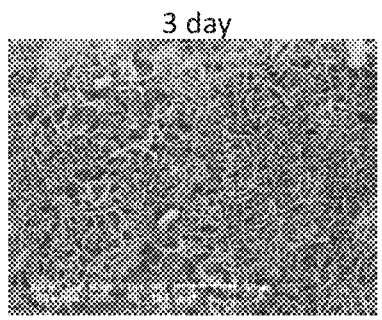
FIG. 2A-FIG. 2F are a series of micrographs depicting the coating surfaces on a PCL scaffold after incubation with DPBS.
Figure 2B:
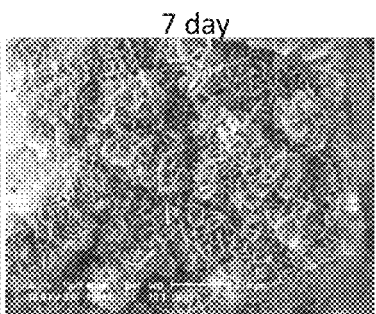
Figure 2C:
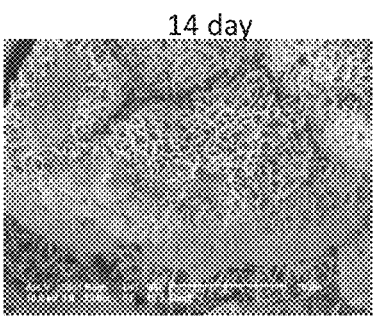
Figure 2D:
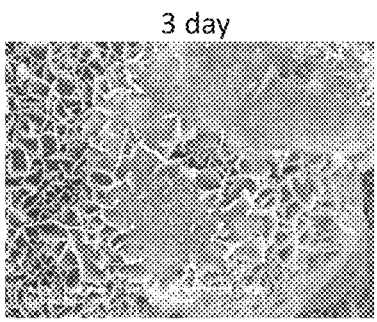
Figure 2E:
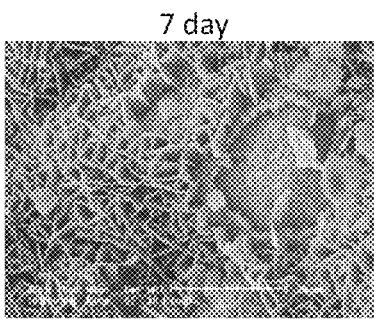
Figure 2:
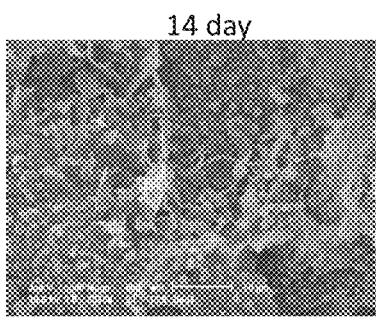
Figure 3A:
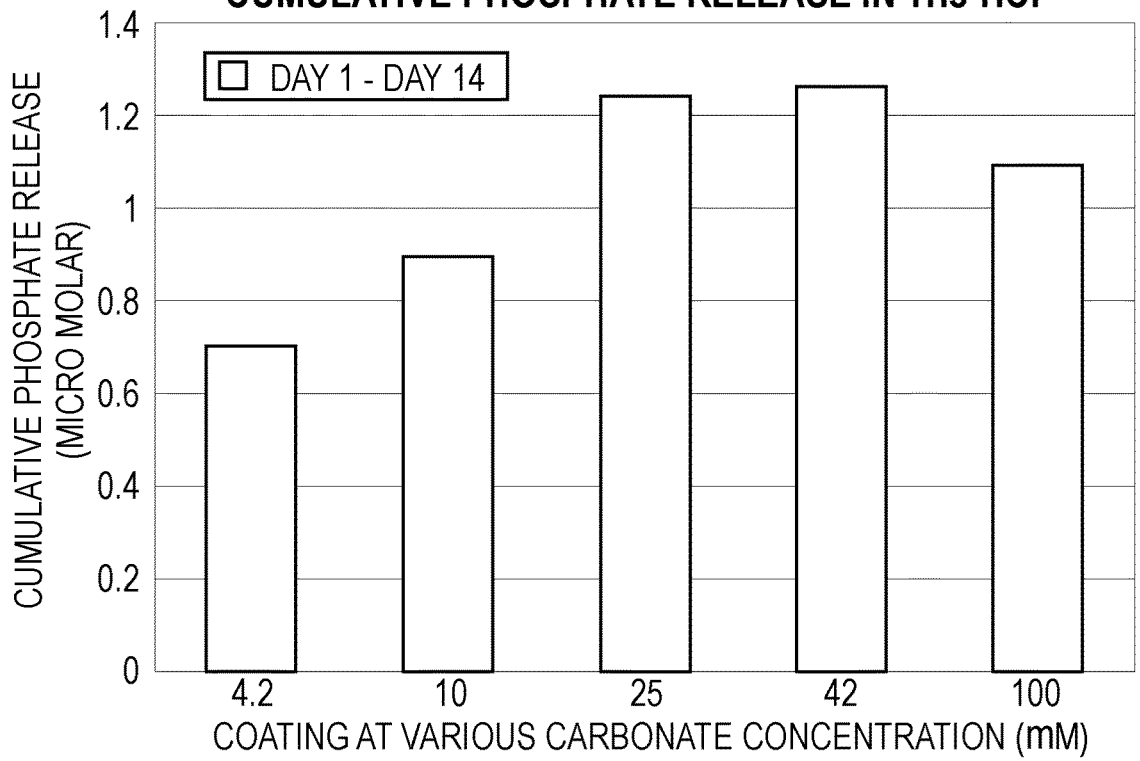
FIG. 3A-FIG. 3B are a series of bar graphs depicting the amount of cumulative release of phosphate or calcium.
Figure 3B:
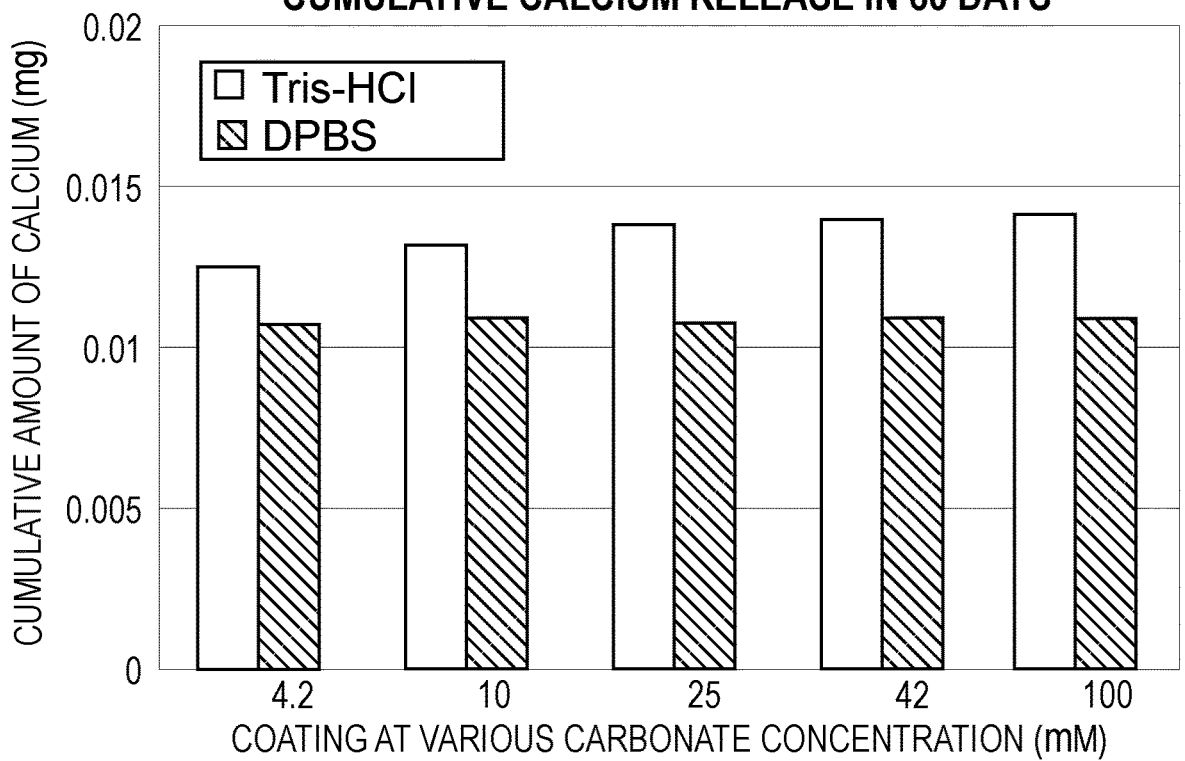

Under simulated physiological conditions, coating dissolution occurred when the environment was undersaturated with calcium and phosphate ions. This was the case for Tris-HCl. But, for the saline buffer, DPBS had phosphate ions in the solution that were believed to be either blocking the dissolution of phosphate ions from the coating or competing against each other for re-precipitation, resulting in the slower rate of dissolution. A series of SEM micrographs (see e.g., FIG. 2) taken at different time points and the amount of calcium (see e.g., FIG. 3) in the release medium support the above hypothesis.

Example 4

Mineral Coating PCL Devices

The following example describes the details, proper instructions and safety precautions for coating polycaprolactone (PCL) medical devices via modified simulated body fluid (mSBF) incubation, wherein the coating procedure applies to any size PCL medical device.

The modified simulated body fluid (mSBF) in this Example is a solution with a similar composition of human plasma but double the concentration of calcium and phosphate. The mSBF solution described in this Example is used for incubating materials and nucleating an apatite-like mineral.

Materials.

Reagents and their respective desired concentration in final solution are as follows. Hydrolysis Reagents: NaOH (1.0 M). Coating Reagents: NaCl (141.0 mM); KCl (4.0 mM); $MgSO_4$ (0.5 mM); $MgCl_2$ (1.0 mM); $NaHCO_3$ (4.2 mM), Tris(hydroxymethyl) aminomethane (20.2 mM) $CaCl_2$ (5.0 mM); $KH_2PO_4$ (2.0 mM). Deionized ultra filtered (DIUF) water. Buffers: 2N HCl; 2N NaOH. Hot plate/stirrer; Magnetic stir bar; Spatula; Weighing paper or weigh boat; Analytical mass balance; pH meter; Glass beakers capable of holding desired volume of mSBF; and 37° C. and 5% $CO_2$ Incubator. Rotating system: Labquake shaker system (for any container size up to 175 mL); Large coating system (for coating large device, see e.g., TABLE 2).

TABLE 2

Coating matrix using large coating system.

| | Description | Example | |
|---|---|---|---|
| Sample size (dimensions in mm) | X ≥ 30 mm × 30 mm × 50 mm; Mass ≥ 3500 mg | Pig sleeve (80 × 45 × 25 mm) | Degradation disc w. handle (35 dia × 5 mm) |
| Type of container | Custom made device for large coating system | Large coating system | Large coating system |
| No. of sample/container | 10-100, due to the large volume of mSBF used we need to maximize the no. of sample per coating duration | 10 | 85 |

TABLE 2-continued

Coating matrix using large coating system.

| | Description | Example | |
|---|---|---|---|
| Volume of mSBF (gallon) | Working volume of 1.5-5 gallons | 3.0 gallons | 2.75 gallons |
| Frequency of changing mSBF (day) | 3 days | 3 days | 3 days |
| Coating duration (day) | 8-14 days, depending on the size and no. of sample | 10 days | 8 days |
| pH adjusting | Daily | Daily | Daily |

Hydrolysis Preparation.

Hydrolysis preparation includes determining the desired volume of 1M NaOH. See TABLE 3 for desired volume based on device size and weight.

TABLE 3

Hydrolysis matrix.

| | | | | |
|---|---|---|---|---|
| Sample size (dimensions in mm) and/or mass (mg) | 10 mm × 10 mm × 10 mm ≤ X; mass ≤ 250 mg | 10 mm × 10 mm × 10 mm < X < 25 mm × 25 mm × 5 mm; mass ≤ 2000 mg | 10 mm × 10 mm × 10 mm < X < 25 mm × 25 mm × 10 mm; mass ≤ 3500 mg | X ≥ 25 mm × 25 mm × 25 mm |
| Type of container | 50 mL conical tube | 50 mL conical tube | 175 mL conical tube | Depends on the size of sample |
| No. of sample/ container | 10-30, total sample volume occupied ≤ ⅓ total volume of container | 2-20, total sample volume occupied ≤ ⅓ total volume of container | 5-45, total sample volume occupied ≤ ⅓ total volume of container | Depends on the size of sample and selected container |
| Volume of 1M NaOH (mL) | 50 mL | 50 mL | 150 mL | Depends on the size of sample and selected container |
| Example | Test cube (6 × 6 × 6 mm), Monkey pin (10 × 5 × 3 mm), Rabbit plate (10 × 5 × 5 mm) | Porous cylinder (7 dia × 16 mm), Human module (20 × 20 × 12 mm), Monkey mandible (30 × 14 × 10 mm) | Porous cylinder (7 dia × 16 mm), Porous block (25 × 25 × 6), Monkey mandible (30 × 14 × 10 mm) | Pig module (35 × 30 × 10 mm), Pig sleeve (80 × 45 × 25 mm), Human sleeve (90 × 20 × 15 mm) |

Determination of the mass of solid state NaOH is required to prepare a 1M NaOH solution. Sample Calculation:

Desired volume of 1M NaOH: 400 mL
Required mass of solid state NaOH:

$$m_{NaOH} = [NaOH], \frac{mol}{L} * Vol_{NaOH}, mL * MW_{NaOH}$$

$$m_{NaOH} = \frac{1 \, mol}{L} * 0.4 \, L * \frac{40 \, g}{mol} = 16 \, g \, NaOH$$

Place hot plate/stirrer and analytical balance on rigid and leveled surface.

Coating Preparation.

Determine the desired volume of mSBF. See TABLE 2 and TABLE 4 for desired volume based on device size and weight. Note that for larger PCL devices, the mSBF may need to be prepared in several batches; if so, determine the desired volume of the batch. Determine the mass of each reagent needed to reach the desired concentration of each reagent (as listed above) in the batch volume.

TABLE 4

Coating matrix.

| | | | |
|---|---|---|---|
| Sample size (dimensions in mm) and/or mass (mg) | 10 mm × 10 mm × 10 mm ≤ X; mass ≤ 250 mg | 10 mm × 10 mm × 10 mm < X < 25 mm × 25 mm × 90 mm; mass ≤ 7500 mg | 10 mm × 10 mm × 10 mm < X < 35 mm × 35 mm × 50 mm; mass ≤ 10,000 mg |
| Type of container | 15 mL conical tube | 50 mL conical tube | 175 mL conical tube |
| No. of sample/ container | 1-10, total sample volume occupied < ½ total volume of container | 1-15, total sample volume occupied < ½ total volume of container | 1-5, total sample volume occupied < ½ total volume of container |

TABLE 4-continued

| Coating matrix. | | | |
|---|---|---|---|
| Volume of mSBF (mL) | 15 mL | 50 mL | 175 mL |
| Frequency of changing mSBF (days) | 2 days | 2 days | 2 days |
| Coating duration (days) | 8 days | 8 days | 8 days |
| pH adjusting | None | None | None |
| Example | Test cube (6 × 6 × 6 mm), Monkey pin (10 × 5 × 3 mm), Rabbit plate (10 × 5 × 5 mm) | Porous cylinder (7 dia × 16 mm), Human module (20 × 20 × 12 mm), Monkey mandible (30 × 14 × 10 mm), Human sleeve (90 × 20 × 15 mm) | Pig module (35 × 30 × 10 mm), Disc (35 dia × 5 mm) |

Sample Calculation:
Desired volume of mSBF: 500 mL mSBF
Required mass of reagent #1 (e.g. NaCl, 141 mM)

$$m_{NaCl} = [NaCl], \frac{mmol}{ml} * Vol_{mSBF}, ml * MW_{NaCl}$$

$$m_{NaCl} = \frac{141 \times 10^{-3} \, mmol}{ml} * 500 \, ml * \frac{58.4 \, mg}{mmol} = 4120 \, mg$$

Place hot plate/stirrer and analytical balance on rigid and leveled surface. Check that the incubator is maintaining a 37° C. temperature and a 5% $CO_2$ level. Check that the pH meter has been recently calibrated. If it has not been calibrated within the past 2 weeks, calibrate it according to the manufacturer's instructions.

Hydrolysis.

Measure the desired volume of DIUF water in an appropriately sized beaker. Place beaker on the hot plate/stirrer. Add magnetic stir bar to the DIUF water. Set the stirrer between settings 5 and 10, depending on the volume of DIUF water. Using a spatula and weighing paper or weigh boat, weigh the required amount of NaOH on an analytical mass balance. Add the reagent to the beaker with the DIUF water. Stir continuously until completely dissolved. Add 1M NaOH to PCL devices. Hydrolyze the PCL devices in the 1M NaOH for 1 hour, rotating the container in a circular motion during hydrolysis. Make sure that the 1M NaOH covers the entire surface of the PCL device during hydrolysis. After hydrolysis is complete, remove 1M NaOH from the container with the PCL devices. Rinse the PCL devices in DIUF water for 15 minutes. PCL devices ready for coating.

Coating.

Measure the desired volume of DIUF water in an appropriately sized beaker. Place beaker on the hot plate/stirrer. Add magnetic stir bar to the DIUF water. Set the stirrer between settings 5 and 10, depending on the volume of DIUF water. Preheat the DIUF water by setting the hot plate to ~40° C. (or setting 2-4). [Note: slowly heat the water from room temperature as reagents are added, and if 37° C. is reached, lower the heat setting to maintain the temperature of the water.] Using a spatula and weighing paper or weigh boat, weigh the required amount of reagent #1 (NaCl) on an analytical mass balance. Add the reagent to the beaker with the preheated DIUF water. While the solution is prepared, stir continuously. Wipe the spatula with ethanol or methanol after each use. Repeat for all of the reagents in order (as listed in Reagents). Add the reagents one at a time, ensuring that each reagent is fully dissolved before the next one is added. The temperature of the DIUF water should be between 24-26° C. while reagents are being added, with the DIUF water slowly heated to a temperature between 28-32° C. by the time all reagents are added. Note: It is normal for the mSBF solution to become basic (pH ~9) after addition of tris(hydroxymethyl) aminomethane and to become cloudy after the addition of $CaCl_2$.

Measure the pH of the solution using the pH meter. Buffer the solution to pH=6.8±0.1 using 2N HCl and 2N NaOH. Start buffering with 2N HCl as the resulting solution is basic (pH 8-9). When the pH falls to ~7.5, the solution will start to become clear. If HCl is added in excess and the pH falls below 6.8±0.1, use NaOH to adjust the pH to 6.8±0.1. While buffering the mSBF solution, continuously stir the solution and maintain the temperature at 37° C. Slowly heat the solution to 37° C. (if the solution has not yet reached 37° C. at the end of the buffering process). Keep checking the pH and the temperature for stability. Repeat until the desired volume is reached. mSBF should be stored in the 37° C. incubator until use. Adjust the pH of the final bulk volume to 6.8±0.1. Add mSBF solution to PCL devices for coating. Incubate the PCL devices in the 37° C. incubator, rotating the container in a circular motion during incubation. Make sure that the mSBF covers the entire surface of the PCL device during incubation. See TABLE 2 and TABLE 4 for coating duration, frequency of changing the mSBF solution, and pH adjustment (if necessary).

After incubation is complete, remove mSBF from the container with the PCL devices. Rinse the PCL devices in DIUF water for 15 minutes. Remove the DIUF water from the container with the PCL devices. Freeze the PCL devices in a −20° C. freezer. Lyophilize the frozen PCL devices. PCL devices ready for sterilization.

Special Precautions.

Wear latex gloves while handling all chemicals, solutions, and/or instruments.

If the mSBF solution turns cloudy during incubation before 2 (or 3 days for large coating system set up), change the solution as soon as possible.

Care and Maintenance of Equipment.

Daily: Calibrate the analytical mass balance to ensure accuracy of weighed reagents. Weekly: Check the status of the $CO_2$ levels in the incubator. Replace $CO_2$ tank(s) as needed according to manufacturer's instructions. Every two weeks: Calibrate the pH meter according to the manufacturer's instructions.

Example 5

Surface Pre-Treatments of Titanium Sample Prior Coating

The following example describes the details, proper instructions, and safety precautions for pretreating titanium samples.

Using 5 M NaOH. (a) Each step below need to be performed in a certified chemical hood and (b) volume of pre-treatment solution depends on size and shape of titanium samples, multiple samples may be pre-treated in the same container.

Very slowly add NaOH pellets (Fisher Scientific Lot #115786) to stirring deionized ultra-filtered (DIUF) water (Fisher Lot #140300) in a glass beaker to make 5 M NaOH solution. Keep beaker on stirrer in hood with stirrer on 'low'. Be mindful of fumes and rising temperatures—further slow down if excessive heating occurs. Let the solution stands for several minutes to cool down. Place Ti sample in clean glass beaker, pour NaOH solution in, cover the beaker with parafilm. Place beaker in sonicator for 1 hr. Keep monitoring sample during sonicator process, take note for the volume of bubbles rising. Take Ti sample out, place it in another beaker with DIUF and leave on shaker for 15 min. Blot dry with paper towel, sample is now ready for coating process.

Using Piranha solution (conc. $H_2SO_4$+30% $H_2O_2$). Each step below is performed in a certified chemical hood. Volume of pre-treatment solution depends on size and shape of titanium samples, multiple samples may be pre-treated in the same container. Add $H_2SO_4$ (Sigma Aldrich Lot #SHBB3339V) to a clean glass beaker in the hood. Very slowly add 30% $H_2O_2$ (Fisher Scientific Lot #102727) to $H_2SO_4$. The reaction can be explosive and is highly exothermic, proceed very slowly and with caution. Place Ti sample in clean glass beaker, carefully pour piranha solution in. Monitor sample for 5-20 minutes; observe for volume of bubbles rising. Immediately stop the reaction if there is any brownish color of sample/solution appear and take sample out.

Take Ti sample out quickly with forceps, rinse with copious amount of DIUF, then place in DIUF on shaker for 15 min. Blot dry with paper towel, sample is now ready for coating process.

Coating Process.

After pre-treatment, each sample was coated for 4-6 days in coating solution (1× mSBF) at 37° C. with solution refreshed daily.

Example 6

Coating Enhances Osseointegration of Metal Surfaces

The unique nanoscale architecture of the coating may be applied to virtually any underlying implant surface (e.g., plasma sprayed titanium), reaching all pores of complex scaffolds and improving upon the degree of osseointegration into micro-structured implants.

Figure 4A:
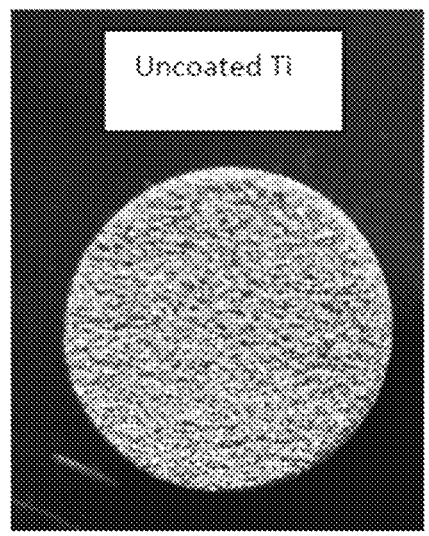
FIG. 4A-FIG. 4B are a series of micrographs depicting the surfaces on a titanium (Ti) scaffold.
Figure 4B:
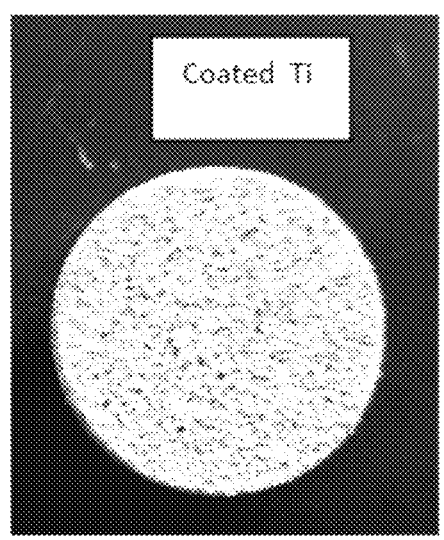
Figure 5A:
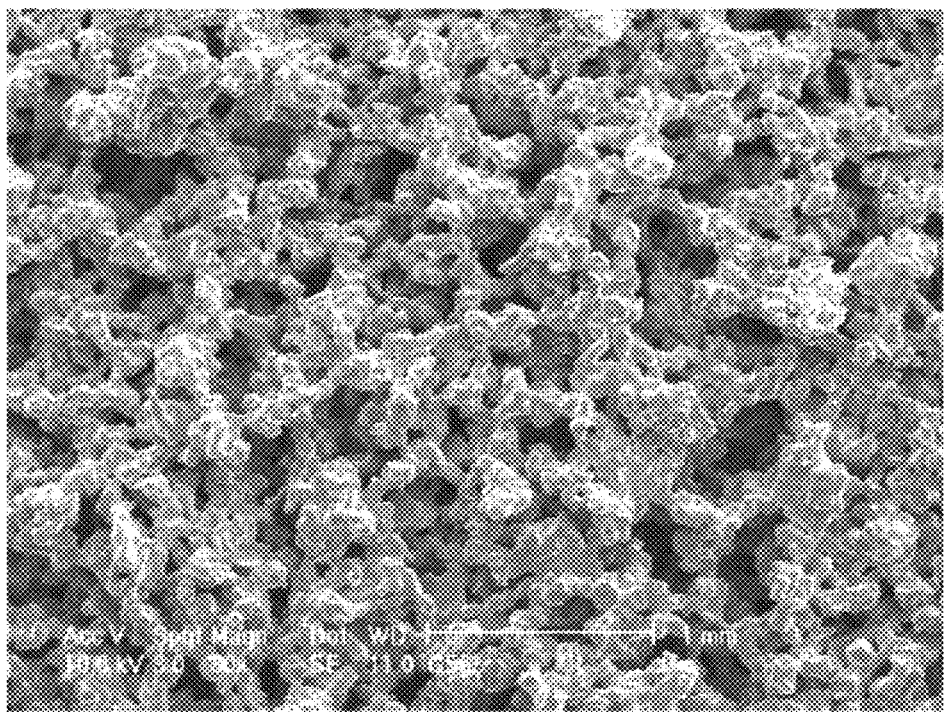
FIG. 5A-FIG. 5D are a series of micrographs depicting the uncoated surfaces on a Ti scaffold.
Figure 5B:
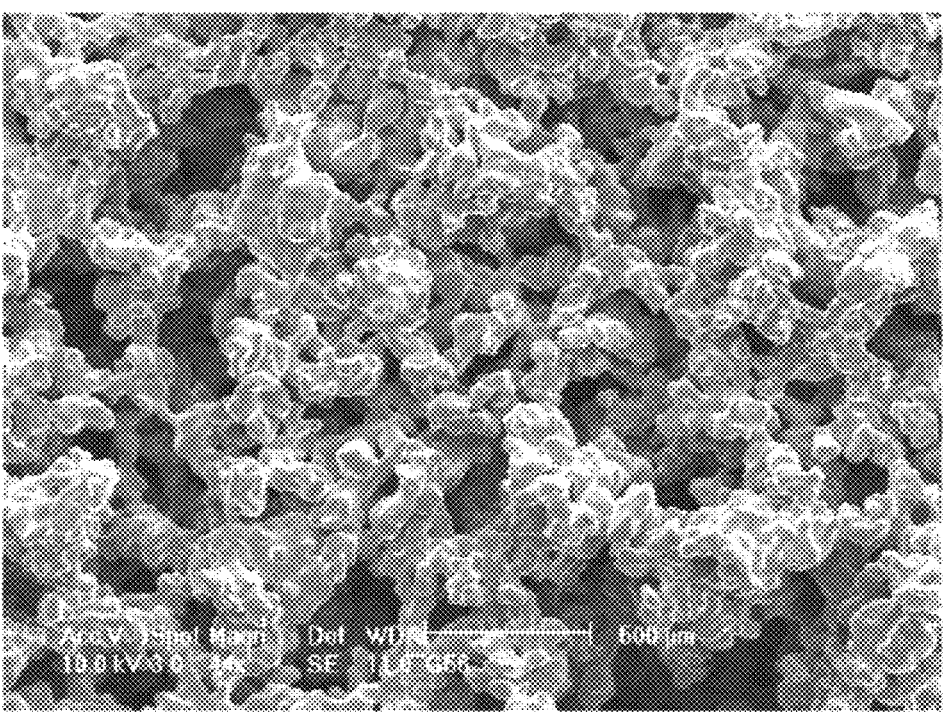
Figure 5C:
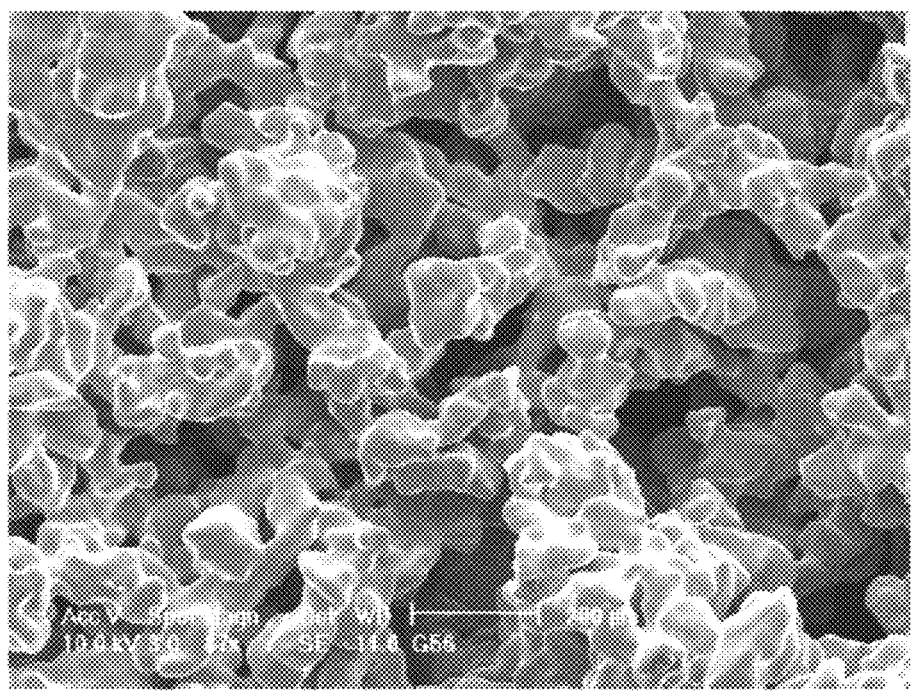
Figure 5D:
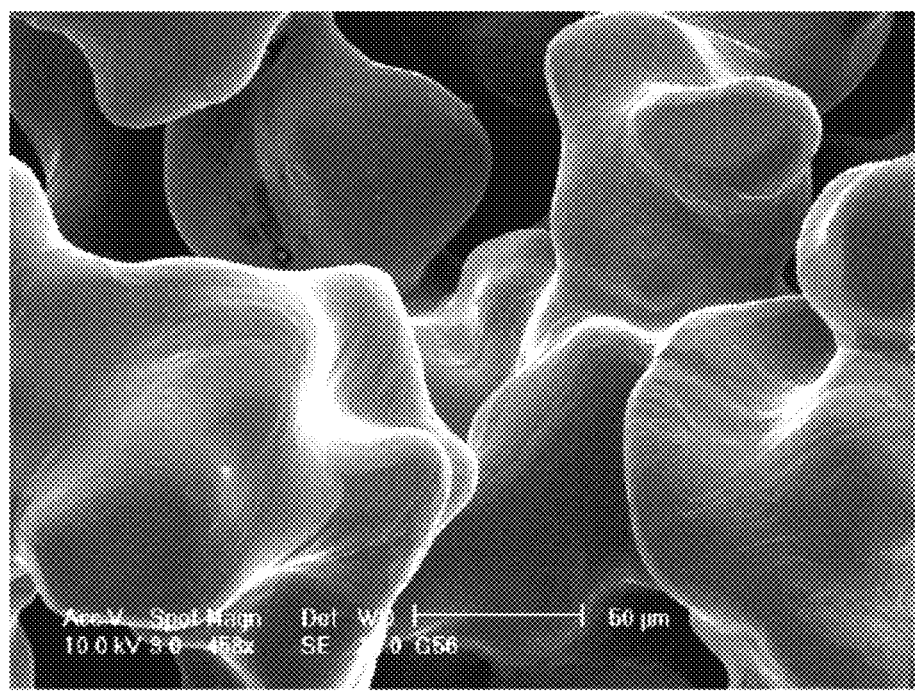
Figure 6A:
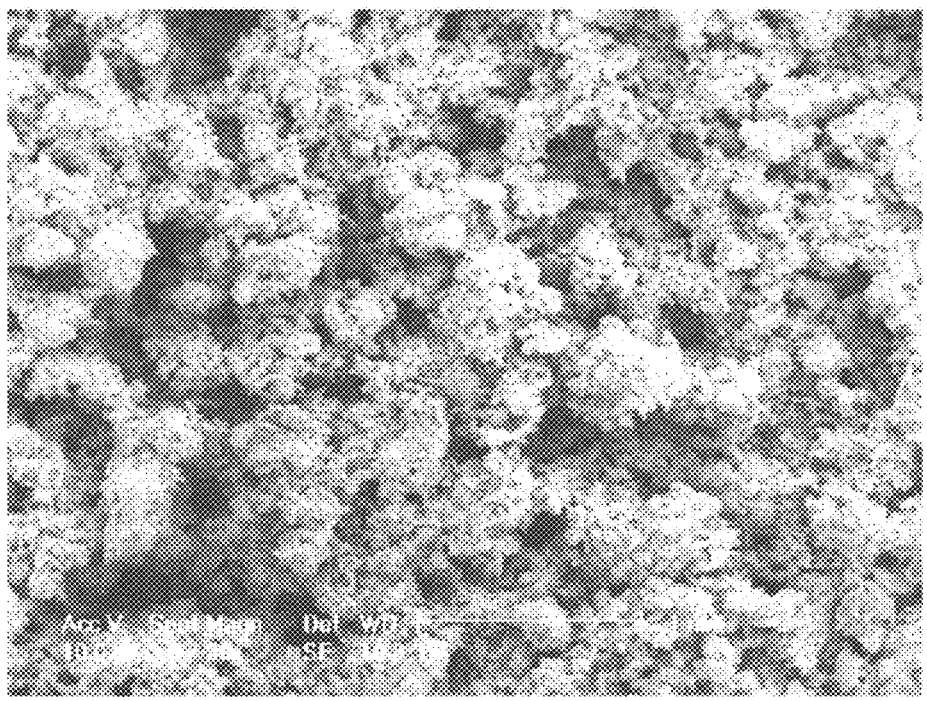
FIG. 6A-FIG. 6D are a series of micrographs depicting the coated surfaces on a Ti scaffold.
Figure 6B:
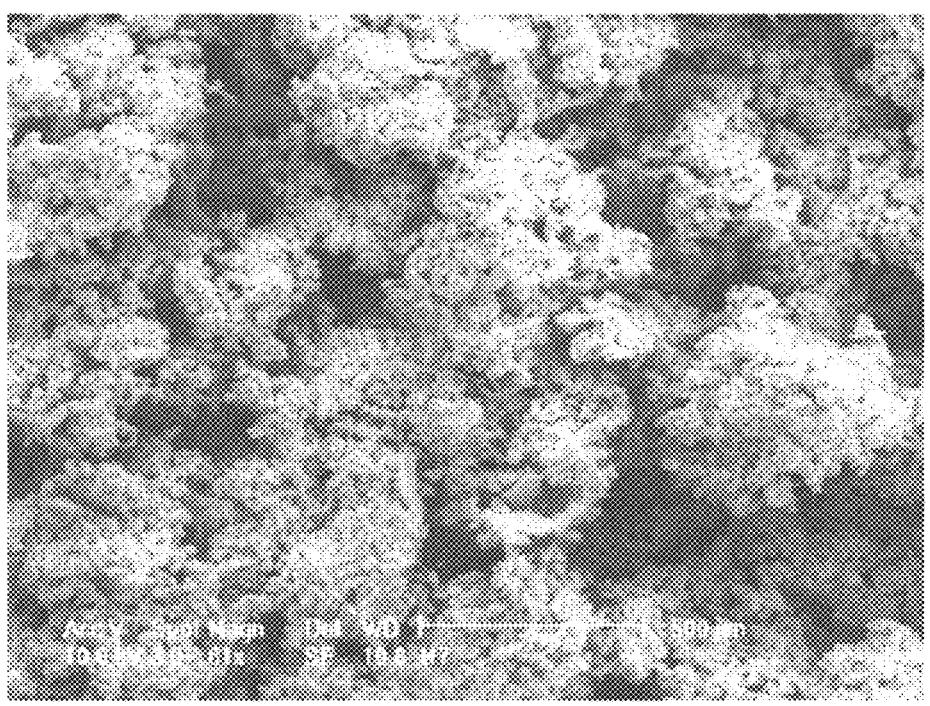
Figure 6C:
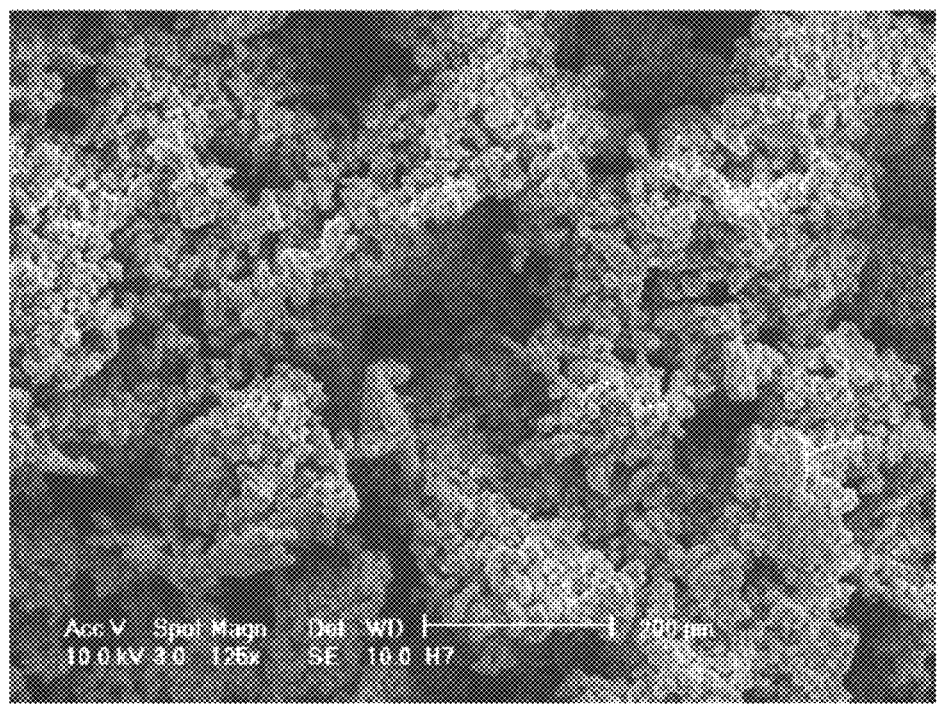
Figure 6D:
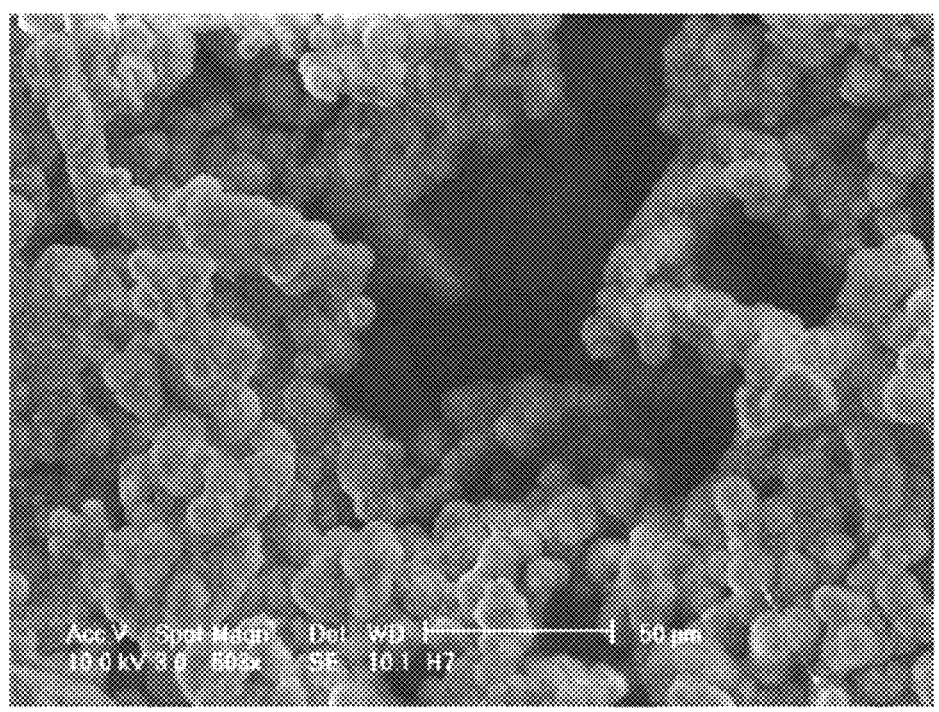
Figure 7A:
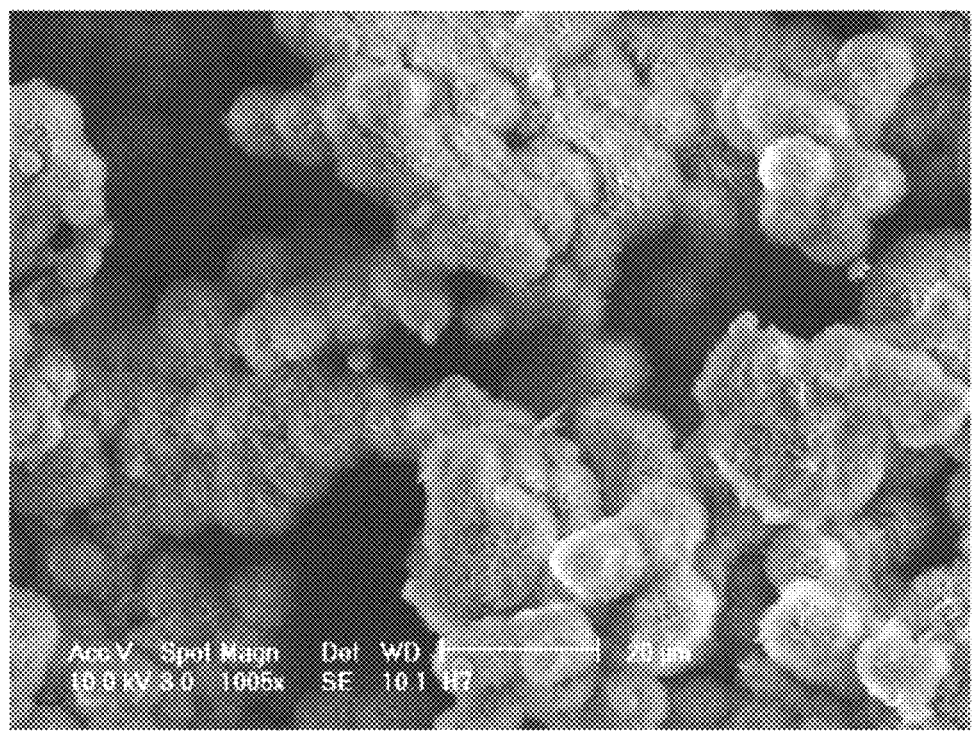
FIG. 7A shows SEM micrographs of the coated Ti (scale bar=20 μm).
Figure 7B:
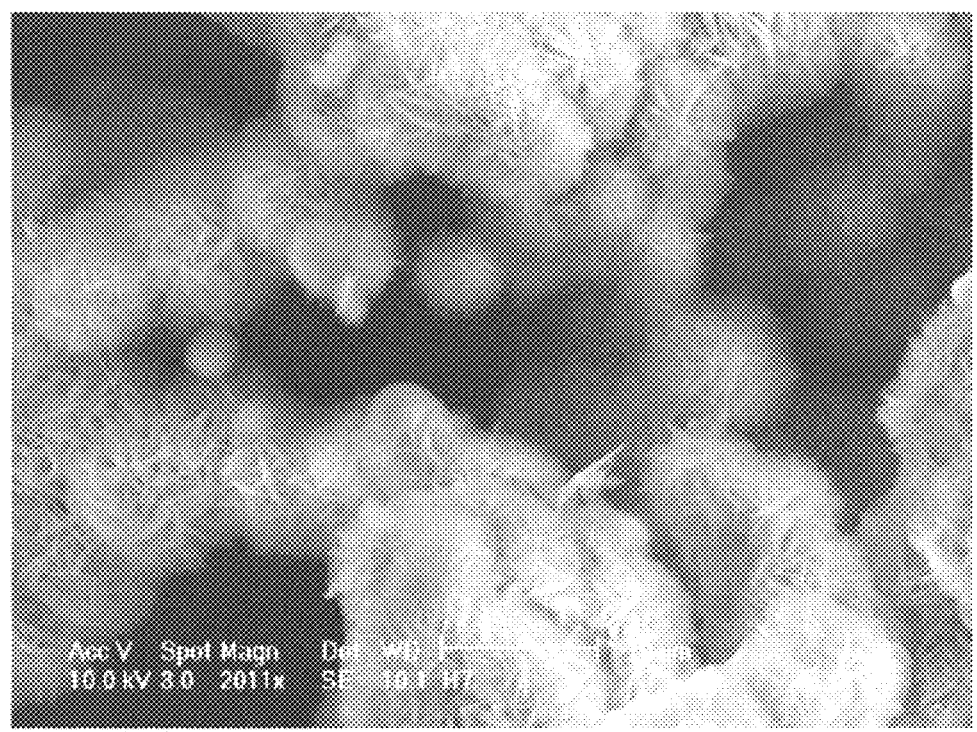
FIG. 7B shows SEM micrographs of the coated Ti (scale bar=10 μm).

FIG. 4A and FIG. 4B show uncoated roughened titanium and coated roughened titanium. Characteristics of the roughened titanium are a 'lava rock' surface structure with a larger pore size between 200-525 µm and a smaller pore size in the range 25-65 µm. The average pore volume=60% and the average surface roughness=132 µm.

Figures 8, 9:
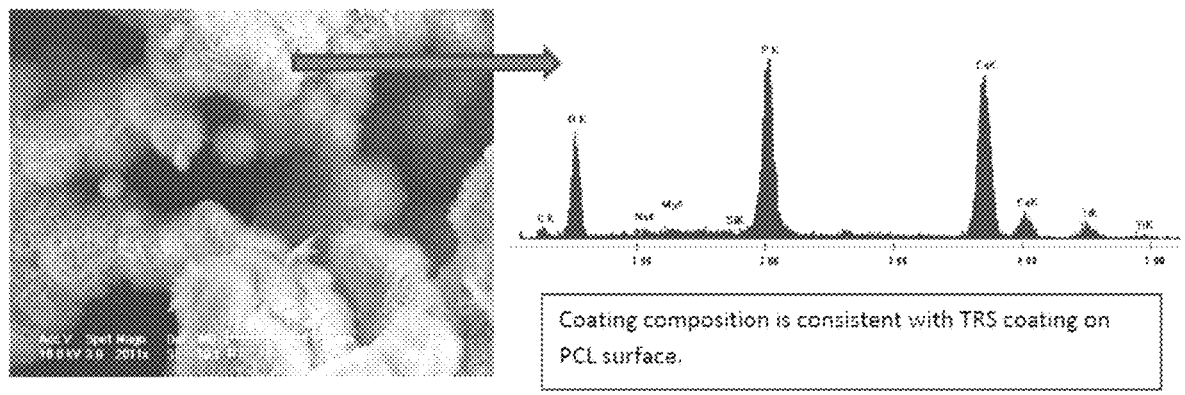
FIG. 8 shows the coating composition on Ti is consistent with the coating on a PCL surface.
FIG. 9 shows the coating thickness on Ti is in the range of 5-15 μm.

It was shown that the coating morphology and composition on titanium is consistent with the same coating on PCL (see e.g., FIG. 8).

Example 7

Demineralized Bone Matrix (DBM) and Silver Nanoparticles Integrated into Mineral Coated Scaffold The following example describes the incorporation of demineralized bone matrix (DBM) to the mineral coating of the scaffold and silver nanoparticles integrated onto the mineral coating of scaffold.

DBM integrated with the mineral coating is presently thought to improve the characteristics of the mineral-coated scaffold, such as the osteoinductive properties. DBM can be integrated into or onto the mineral coating of the scaffold. DBM, such as demineralized bone extract or gel can be incorporated with the aqueous mineral coating solution in Example 4 to form a mixture of DBM and mineral coating solution to coat a scaffold in a single coating step.

DBM can be coated onto a scaffold pre-coated with the mineral coating. The scaffold can be coated with DBM before, during, or after mineral coating using the methods described herein.

Silver nanoparticles integrated with a scaffold or the mineral coating are presently thought to provide biostatic, anti-infection properties to the mineral-coated scaffold. Silver nanoparticles can be integrated onto the mineral coating as described below. The nanoparticles can also be integrated into the scaffold or coating before, during, or after DBM coating using the methods described herein.

The following describes the incorporation of silver nanoparticles onto a CaP coated scaffold. CaP coated scaffolds are incubated in silver nitrate solution in deionized water (pH 7.0, 5 mL) to synthesize silver particles on the surface or coating. In a set of experiments, CaP coatings are pre-treated by incubating in citric acid solution in deionized water (pH 7.0, 5 mL) prior to silver nitrate incubation.

The concentrations of both solutions are varied (e.g., 1, 5, and 10 mM). Incubation times are also varied (e.g., 0.5, 1, and 4 hr). After citric acid pre-treatment, the resultant CaP coatings can be characterized using FT-IR, and crystallinity index can be calculated from Shemesh's method. The calcium released from citric acid-treated CaP coating in PBS at 37° C. can be quantified by colorimetric assay using Arsenazo III (MP Biochemicals, USA). The release medium can be collected at different times to quantify calcium ions. Fresh PBS can be added for further incubation. The silver particles on CaP coatings can be imaged using FE-SEM and elemental analysis using EDS. The silver particles scraped from CaP coatings can be characterized using XRD.

The silver nanoparticle-integrated mineral-coated scaffold can be further incorporated with DBM as described above. Alternatively, the mineral coating can be incorporated with DBM before the addition of silver nanoparticles.

The DBM is integrated with a scaffold by mixing DBM with an aqueous solution. The aqueous solution can be the mineral coating solution. The aqueous solution can be a weak acid or guanidine hydrochloride. The mixture is constantly agitated for a set amount of time to produce an aqueous demineralized bone extract. The extract can then be filtered to remove any remaining solids, the acid neutralized or removed, and the extract used to coat the porous scaffold.

The DBM and aqueous solution or coating solution is mixed from about 8 to 96 hours. The DBM and aqueous solution is mixed together with constant agitation during that time. After mixing for the appropriate amount of time, the resulting demineralized bone extract can be separated from any insoluble DBM remaining in the solution. The aqueous solution or coating solution comprising the DBM is neutralized to a pH of from about 6.5 to about 7.5 by titration with an appropriate counterion. The scaffold is then incubated according Example 4.

Example 8

Experimental Conditions I, II, and III

Figure 10:
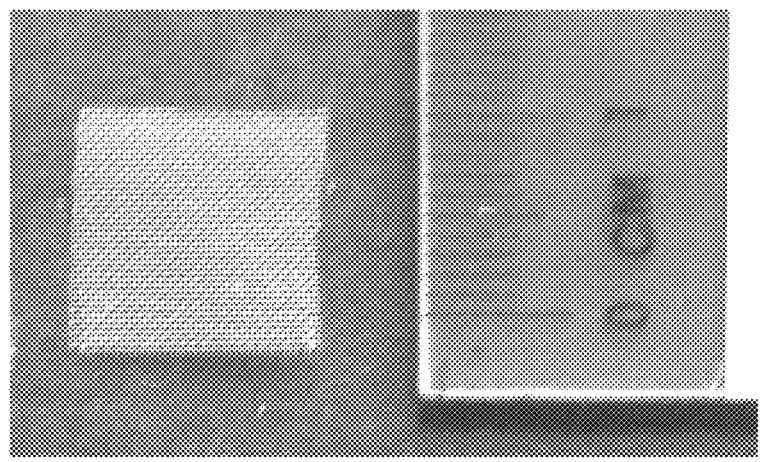
FIG. 10 is an image of a 1 cm×1 cm piece of PEEK mesh.
Figure 11A:
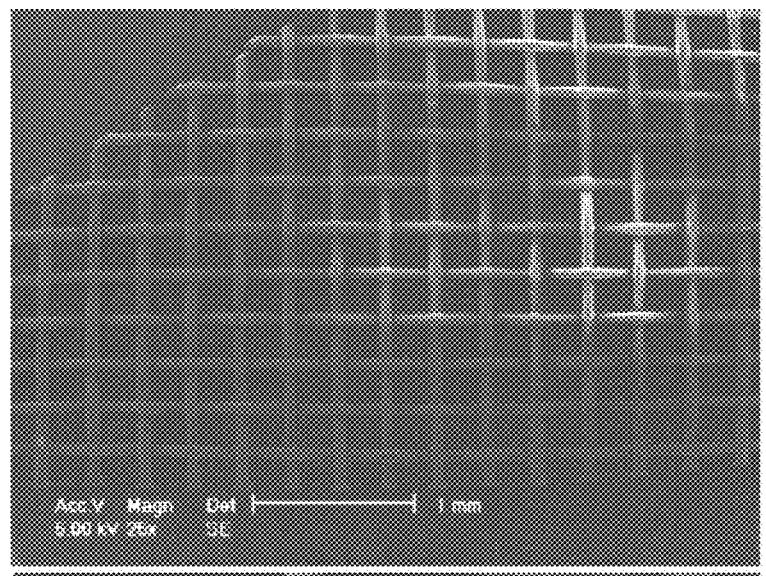
FIG. 11A-FIG. 11B is a series of SEM images depicting PEEK mesh with no coating.
Figure 11B:
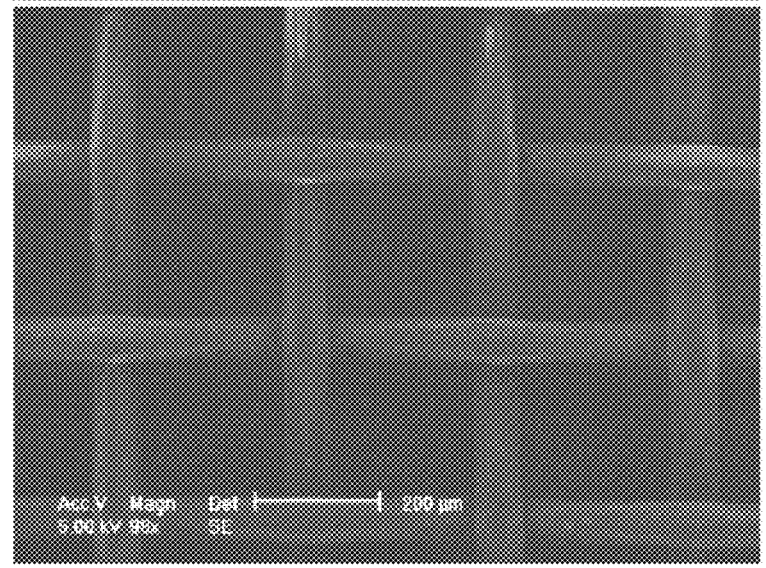

This example describes an overview of the experiments described in the following examples. PEEK mesh was used as the sample for experimental conditions, I, II, and III (see e.g., Examples 13, 14, and 15). PEEK mesh was chosen because it is one of the most challenging materials and geometries to coat (see e.g., FIG. 10, FIG. 11A). Thus, the procedures used in the following examples using PEEK mesh can be translated to any material, especially materials that are known to be difficult to coat, for example, materials having smooth surfaces.

TABLE 1

Experimental conditions: I, II, and III (see e.g., Examples 13, 14, and 15, respectively).

| Experiment | Priming/Dip Coating condition | Hydrolysis condition | Coating condition |
|---|---|---|---|
| I | None | 1M NaOH, 1 hour | 4 Days, mSBF change daily |
| II | None | 3M NaOH, 1 hour | 4 Days, mSBF change daily |
| III | PCL 2.5 wt % in chloroform, vacuum dry for 10 minutes | 0.5M NaOH, 30 minutes | 2 Days, mSBF change daily |

Example 9

Dip Coating Process

The following example describes the dip coating process (a.k.a. polymer priming, pre-treating) for experimental condition III (see e.g., TABLE 1, Example 15) via solvent casting. The dip coating process applies a thin layer of PCL.

Solution Preparation.

Suitable solvents used for PCL solvent casting included chloroform and acetic acid. Due to small pores of PEEK mesh, PCL concentration at or below 3% (w/v) was used to maintain a low viscosity solution.

Added 2 ml of the desired solvent to a 20 ml glass vial.

Weighed desired mass (20 mg/desired % concentration) of milled PCL and add to vial and the vial was closed.

The vial was swirled vigorously or placed on rotator until all of the polymer was completely dissolved in solvent.

PEEK mesh was cut into 1 cm squares (see e.g., FIG. 10), these should each be able to fit upright into a single well of a 48 well plate.

Picked up the very corner of a single PEEK mesh square using tweezers, trying to cover as little of the material as possible while maintaining a secure grip.

The entire square was submerged into the prepared solution and it was observe to confirm that there were no bubbles adhered to the PEEK, if there were, it was shaken gently while submerged to dislodge the bubbles.

The PEEK was removed from the liquid but held still in the vial. If a large bead of solution was present on the mesh, it was gently touched to the inside of the vial wall to break the surface tension and release this extra solution.

The PEEK square was placed upright in a well of a 48-well plate.

When all samples were dipped or the well plate was full, the plate was placed (uncovered) in a vacuum drying chamber and the pump was turned on for about 10 minutes to evaporate the solvent.

Once pressure is equalized, the plate was removed from the chamber and covered. Some coated PEEK samples partially adhered to the well bottoms and required some force to remove when ready.

Example 10

PCL/Chloroform- or PCL/Acetic Acid-DIP Coated Peek

The following example describes the formation of a PCL dip coat on PEEK mesh using PCL in a chloroform solvent or an acetic acid solvent (see e.g., FIG. 10, FIG. 11, FIG. 12, FIG. 13)

The dip coat was performed according to Example 9 using 2.5 wt % PCL in chloroform (see e.g., FIG. 12A-FIG. 12B) or 2.5 wt % PCL in acetic acid (see e.g., FIG. 13A-FIG. 13B). PCL in either chloroform (see e.g., FIG. 12A-FIG. 12B) or acetic acid (see e.g., FIG. 13A-FIG. 13B) solvent was observed to coat the PEEK uniformly. A very thin layer of PCL was observed on the surface and had no effect on the overall pores or porosity.

Example 11

Hydrolysis Process

The following example describes the hydrolysis process for three experimental conditions, I, II, and III (see e.g., Examples 13, 14, and 15).

Hydrolysis of Samples.

1. Determine the desired volume and concentration of NaOH based on the size and weight of samples.

2. Determine the mass of solid state NaOH required to prepare NaOH solution.

Sample Calculation.

Desired volume of 1 M NaOH: 400 mL

Required mass of solid state NaOH:

$$m_{NaOH} = [NaOH], \frac{\text{mol}}{\text{L}} * Vol_{NaOH}, \text{mL} * MW_{NaOH}$$

$$m_{NaOH} = \frac{1\,\text{mol}}{\text{L}} * 0.4\,\text{L} * \frac{40\,\text{g}}{\text{mol}} = 16\,\text{g NaOH}$$

3. Place hot plate/stirrer and analytical balance on rigid and leveled surface.

4. Measure the desired volume of DIUF water in an appropriately sized beaker. Place beaker on the hot plate/stirrer.

5. Add magnetic stir bar to the DIUF water. Set the stirrer for appropriate stir the DIUF water.

6. Using a spatula and weighing paper or weigh boat, weigh the required amount of NaOH on an analytical mass balance. Add the reagent to the beaker with the DIUF water. Stir continuously until completely dissolved.

7. Add NaOH solution to samples. Hydrolyze 15 minutes-1 hour, rotating the container in a circular motion during hydrolysis. Make sure that NaOH solution covers the entire surface of the samples during hydrolysis.

8. After hydrolysis is complete, remove samples. Rinse samples with DIUF water for 15 minutes. The sample is now ready for coating.

Example 12

Mineral Coating Process

The following example describes the mineral coating process for three experimental conditions, I, II, and III (see e.g., Examples 13, 14, and 15).

Coating Process.

1. Determine the desired volume of modified simulated body fluid (mSBF), based on device/sample size and weight.
2. Determine the mass of each reagent needed to reach the desired concentration of each reagent as listed below.

Coating Reagents.
NaCl (141.0 mM)
KCl (4.0 mM)
$MgSO_4$ (0.5 mM)
$MgCl_2$ (1.0 mM)
$NaHCO_3$ (4.2 mM)
Tris(hydroxymethyl)aminomethane (20.2 mM)
$CaCl_2$ (5.0 mM)
$KH_2PO_4$ (2.0 mM)

Sample Calculation.
Desired volume of mSBF: 500 mL mSBF
Required mass of reagent #1 (e.g. NaCl, 141 mM)

3. Place hot plate/stirrer and analytical balance on rigid and leveled surface.
4. Measure the desired volume of DIUF water in an appropriately sized beaker. Place beaker on the hot plate/stirrer.
5. Add magnetic stir bar to the DIUF water. Set the stirrer to appropriate stir the DIUF water.
6. Preheat the DIUF water by setting the hot plate to ~40° C. (or setting 2-4).
7. Using a spatula and weighing paper or weigh boat, weigh the required amount of reagent #1 (NaCl) on an analytical mass balance. Add the reagent to the beaker with the preheated DIUF water. While the solution is prepared, stir continuously.
8. Wipe the spatula with kimwipe after each use.
9. Repeat #7-8 for all of the reagents in order (as listed in "Coating Reagents" section). Add the reagents one at a time, ensuring that each reagent is fully dissolved before the next one is added. The temperature of the DIUF water should be between 24-30° C. while reagents are being added. It is normal for the mSBF solution to become basic (pH ~9) after addition of tris(hydroxymethyl)aminomethane and to become cloudy after the addition of $CaCl_2$.
10. Measure the pH of the solution using the pH meter.
11. Buffer the solution to pH=6.8±0.1 using 2 N HCl and 2N NaOH. Start buffering with 2 N HCl as the resulting solution is basic (pH 8-9). When the pH falls to ~7.5, the solution will start to become clear. If HCl is added in excess and the pH falls below 6.8±0.1, use NaOH to adjust the pH to 6.8±0.1. While buffering the mSBF solution, continuously stir the solution and maintain the temperature at 37° C.
12. Add mSBF solution to hydrolyzed samples according to Example 11. Incubate the solution in a rotating the container in a circular motion during incubation. Make sure that the mSBF covers the entire surface of the samples during incubation.
13. mSBF was refreshed every 24 or 48 hours for up to 4 days.
14. After incubation is complete, remove coated samples from the mSBF. Rinse the samples in DIUF water for 15 minutes.
15. Freeze the coated samples in a −20° C. freezer.
16. Lyophilize the frozen, coated samples.

Example 13

Condition I—Hydrolysis (1 M NaOH) and Four Day Coating

The following example describes the hydrolysis process for experimental condition I.

The mineral coating of a PEEK mesh scaffold was performed using no dip coating, the hydrolysis method as described in Example 11, with 1 M NaOH for 1 hour, and the mineral coating method as described in Example 12, coated for 4 days.

Condition I (hydrolysis (1 M NaOH) and coating process (4 days of coating)) had the least amount of coating when compared to condition II and condition III.

It was observed that the coating formed sporadically under this condition (see e.g., FIG. 12A-FIG. 12D).

Example 14

Condition II—Hydrolysis (3M NaOH) and Four Day Coating

The following example describes the hydrolysis process for experimental condition II.

The mineral coating of a PEEK mesh scaffold was performed using no dip coating, the hydrolysis method as described in Example 11, with 3 M NaOH for 1 hour, and the mineral coating method as described in Example 12, coated for 4 days.

Similar to conventional metal coating techniques, the pre-treatment in condition II is harsh and potentially could damage the underlying substrate. As observed in the P2 damaged samples (harsh conditions), the mesh channels distorted during the attempt to roughen the PEEK surface.

It was observed that more coating formed under this condition than with condition I, but this condition caused more damage to the PEEK mesh (see e.g., FIG. 13A-FIG. 13D).

Example 15

Condition III—Dip Coat, Hydrolysis, and Coating

The following example describes polymer priming of PEEK mesh with hydrolysis and a 2 day mineral coating.

The methods described below primed the PEEK substrate with a PCL solution (dip coat with PCL). The PCL coated PEEK mesh was then coated with a mineral layer using mSBF. In other words, a very thin layer of PCL was applied on the surface of PEEK to create affinity coating on that PCL layer. The PCL layer was observed to be thin and had no effect to the overall pores and porosity of the PEEK material. It was observed that the mesh was sufficiently coated after PCL primed and 2 days in the mSBF mineral coating solution.

Condition III is another way to coat PEEK, metal, or any substrate that is not readily able to be coated by conventional coating processes without harsh pre-treatment conditions. The following example uses resources, methods, and materials that are compatible with the FDA.

The polymer priming process, in condition III, is milder and faster compared to previously used and conventional pre-treatment conditions. Condition III has also been shown to be faster to mineral coat (2 days instead of 4 days). It is presently thought that this technique could potentially be a solution to coat any challenging substrates (e.g., PEEK, metals, smooth substrates). In addition, it is possible to customize the polymer primer to be degraded at specific time (e.g., PLGA could be used which has faster degradation time (and approved by FDA) instead of PCL.

It was observed that condition III had the best coating in terms of morphology and uniformity of coating when compared to condition I or condition II (see e.g., FIG. 14A-FIG. 14D). It was further observed that the condition III mineral coating forms faster, more uniform, and does not interfere with the macrochannel of the mesh (see e.g., FIG. 14A-FIG. 14D). Condition I (1 M NaOH hydrolysis and four day coating process) had the least amount of coating. Condition II (3M hydrolysis and four day coating) had a little bit more coating (but not as good as III).

This example demonstrated that PEEK can be coated by "priming" with a resorbable thin film that temporarily supports the mineral coating process. The combination of solvent casting and drying techniques created a thin film of bioresorbable polymer with a unique surface morphology to encapsulate PEEK.

The invention claimed is:

1. A method for producing a mineral coated polycaprolactone (PCL) scaffold comprising:
   providing a solvent comprising a chloroform or acetic acid, and a PCL scaffold, the PCL scaffold being in an amount from about 2 to about 3% w/v based on the % of the solvent;
   dipping a polyetheretherketone (PEEK) mesh in the solvent;
   drying the PCL scaffold and the PEEK mesh;
   hydrolyzing the PCL scaffold and the PEEK mesh with from about 0.5 M to about 3 M NaOH to form a primer coated PCL scaffold;
   contacting the primer coated PCL scaffold with a modified simulated body fluid, the modified simulated body fluid comprising 20 mM Tris, at least 5 mM $CaCl_2$ and at least 2 mM $KH_2PO_4$;
   incubating the primer coated PCL scaffold and the modified simulated body fluid for a period of time from about 2 to about 4 days under conditions sufficient to form a mineral coated PCL scaffold, wherein the modified simulated body fluid is adjusted to a pH of about 6.5 to about 7.2, and the modified simulated body fluid is changed daily and the primer coating of the PCL scaffold comprises a continuous or discontinuous coating and the primer coating promotes mineral coating of the PCL scaffold, wherein the mineral coating comprises a carbonate-substituted, calcium-deficient hydroxyapatite component, and the mineral coating has a plate-like nanostructure and a porosity between about 20% and about 28%;
   incubating the primer coated PCL scaffold with a citric acid solution; and
   incorporating silver particles with the mineral coated PCL scaffold by incubating the mineral coated PCL scaffold in a solution containing the silver particles such that the silver particles are configured to be linearly released from the mineral coated PCL scaffold.

2. A method for producing a mineral coated polycaprolactone (PCL) scaffold comprising:
   providing a solvent comprising chloroform and a PCL scaffold, the PCL scaffold being in an amount being in an amount of about 2.5% w/v based on the % of the solvent;
   dipping a polyetheretherketone (PEEK) mesh in the solvent;
   drying the (PCL) scaffold and the PEEK mesh for about 10 minutes;
   hydrolyzing the (PCL) scaffold and the PEEK mesh with 0.5 M NaOH for about 30 minutes;
   incubating the (PCL) scaffold and the PEEK mesh for a period of time under conditions sufficient to form a primer coated (PCL) scaffold over the PEEK mesh;
   contacting the primer coated (PCL) scaffold over the PEEK mesh with a modified simulated body fluid, the modified simulated body fluid comprising 20 mM Tris, at least 5 mM $CaCl_2$ and at least 2 mM $KH_2PO_4$;
   incubating the primer coated (PCL) scaffold over the PEEK mesh and the modified simulated body fluid for 2 days under conditions sufficient to form a mineral coated primer coated (PCL) scaffold, by adjusting the modified simulated body fluid to a pH of about 6.5 to about 7.2, wherein the modified simulated body fluid is changed daily;
   wherein the mineral coating comprises a plate-like nanostructure and a carbonate-substituted, calcium deficient hydroxyapatite component and the mineral coating has a porosity between about 20% and about 28%;
   incubating the primer coated (PCL) scaffold over the PEEK mesh with a citric acid solution; and
   incorporating silver nanoparticles with the (PCL) scaffold over the PEEK mesh such that the mineral coated primer coated (PCL) scaffold has antimicrobial, antibacterial, biostatic, or anti-infection properties and the average surface roughness of about 132 μm.

3. The method of claim 1, wherein
   the primer coating comprises a thin film; or
   the primer coating has a thickness of about 1 μm to about 50 μm.

4. The method of claim 1, further comprising combining NaCl, KCl, $MgCl_2$, $MgSO_4$, and $NaHCO_3$, with the $CaCl_2$, Tris, and $KH_2PO_4$ to form the modified simulated body fluid.

5. The method of claim 4, wherein:
   (i) NaCl has a concentration of about 100 mM to about 200 mM; KCl has a concentration of about 1 mM to about 8 mM; $MgCl_2$ has a concentration of about 0.2 mM to about 5 mM; $MgSO_4$ has a concentration of about 0.2 mM to about 5 mM; $NaHCO_3$ has a concentration of about 1 mM to about 100 mM; $CaCl_2$ has a concentration of about 5.5 mM to about 20 mM; and $KH_2PO_4$ has a concentration of about 2.2 mM to about 10 mM; or
   (ii) NaCl has a concentration of about 141 mM; KCl has a concentration of about 4.0 mM; $MgCl_2$ has a concentration of about 1.0 mM; $MgSO_4$ has a concentration of about 0.5 mM; $NaHCO_3$ has a concentration of about 4.2 mM; $CaCl_2$ has a concentration of 5 mM; $KH_2PO_4$ has a concentration of 2.0 mM.

6. The method of claim 1, wherein incubating the primer coating composition and the (PCL) scaffold for a period of time sufficient to form a primer coated scaffold is about 2 days.

7. The method of claim 1, wherein incubating the (PCL) scaffold or incubating the primer coated (PCL) scaffold and the modified simulated body fluid comprises:
  (i) heating the modified simulated body fluid to physiologic temperature or adjusting to a physiologic pH wherein the physiologic temperature is about 37° C. or physiological pH is about 6.8;
  (ii) incubating the (PCL) scaffold in the primer coating composition comprises replacing the primer coating composition, replenishing the primer coating composition, removing the primer coating composition, or adding the primer coating composition; or
  (iii) incubating the (PCL) scaffold in the primer coating composition comprises maintaining a concentration of primer coating composition, wherein maintaining the concentration of primer coating composition comprises replacing, replenishing, removing, or adding polymer, solvent, or a combination thereof.

8. The method of claim 1, wherein incubating the primer coated (PCL) scaffold or (PCL) scaffold in the modified simulated body fluid comprises:
  (i) replacing the modified simulated body fluid, replenishing the modified simulated body fluid, removing the modified simulated body fluid, or adding the modified simulated body fluid; or
  (ii) maintaining a concentration of modified simulated body fluid, wherein maintaining the concentration of modified simulated body fluid comprises replacing, replenishing, removing, or adding NaCl, KCl, $MgCl_2$, $MgSO_4$, $NaHCO_3$, $CaCl_2$, or $KH_2PO_4$, or a combination thereof.

9. The method of claim 1, wherein the (PCL) scaffold comprises:
  (i) a pore diameter between about 200 μm and about 525 μm; between about 25 μm to about 65 μm; or more than about 50 μm; or
  (ii) a macrochannel length of more than about 100 μm.

10. The method of claim 1, wherein the mineral coating comprises:
  (i) about 0.1 to about 18 Ca/P or about 1.1 to about 1.76 Ca/P (calcium to phosphate ratio);
  (ii) about 1.67 to about 1.76 Ca/P; about 1.1 to about 1.3 Ca/P; or about 1.37 to about 1.61 Ca/P; or
  (iii) a crystallinity of about 9% to about 100%; about 90% to about 100%; or about 96.5%.

11. The method of claim 2, further comprising combining NaCl, KCl, $MgCl_2$, $MgSO_4$, $NaHCO_3$, with the $CaCl_2$, and $KH_2PO_4$ to form the modified simulated body fluid, wherein
  (i) NaCl has a concentration of about 100 mM to about 200 mM; KCl has a concentration of about 1 mM to about 8 mM; $MgCl_2$ has a concentration of about 0.2 mM to about 5 mM; $MgSO_4$ has a concentration of about 0.2 mM to about 5 mM; $NaHCO_3$ has a concentration of about 1 mM to about 100 mM; $CaCl_2$ has a concentration of about 5.5 mM to about 20 mM; and $KH_2PO_4$ has a concentration of about 2.2 mM to about 10 mM; or
  (ii) NaCl has a concentration of about 141 mM; KCl has a concentration of about 4.0 mM; $MgCl_2$ has a concentration of about 1.0 mM; $MgSO_4$ has a concentration of about 0.5 mM; $NaHCO_3$ has a concentration of about 4.2 mM; $CaCl_2$ has a concentration of 5 mM; and $KH_2PO_4$ has a concentration of 2.0 mM.

12. The method of claim 2, wherein the (PCL) scaffold comprises:
  (i) a pore diameter between about 200 μm and about 525 μm, between about 25 μm and about 65 μm; or more than about 50 μm; or
  (ii) a macrochannel length of more than about 100 μm.

13. The method of claim 1, wherein the modified simulated body fluid is adjusted to a physiologic pH of about 6.8.

* * * * *